(12) United States Patent
Jayasinghe et al.

(10) Patent No.: US 9,222,082 B2
(45) Date of Patent: Dec. 29, 2015

(54) HYBRIDIZATION LINKERS

(75) Inventors: Lakmal Jayasinghe, Oxford (GB); John Milton, Cambridge (GB); Luke McNeill, Oxford (GB); James Anthony Clarke, Oxford (GB); James White, Oxford (GB); Ruth Moysey, Oxford (GB)

(73) Assignee: Oxford Nanopore Technologies Limited, Oxford (GB)

( * ) Notice: Subject to any disclaimer, the term of this patent is extended or adjusted under 35 U.S.C. 154(b) by 914 days.

(21) Appl. No.: 13/147,176

(22) PCT Filed: Jan. 29, 2010

(86) PCT No.: PCT/GB2010/000132
§ 371 (c)(1),
(2), (4) Date: Nov. 18, 2011

(87) PCT Pub. No.: WO2010/086602
PCT Pub. Date: Aug. 5, 2010

(65) Prior Publication Data
US 2012/0064599 A1 Mar. 15, 2012

Related U.S. Application Data

(60) Provisional application No. 61/148,726, filed on Jan. 30, 2009.

(51) Int. Cl.
| | | |
|---|---|---|
| *C07K 1/00* | (2006.01) | |
| *C07K 1/10* | (2006.01) | |
| *A61K 38/00* | (2006.01) | |
| *C12Q 1/68* | (2006.01) | |
| *C12N 9/22* | (2006.01) | |
| *C07K 14/31* | (2006.01) | |
| *C12N 9/12* | (2006.01) | |
| *C12N 9/90* | (2006.01) | |

(52) U.S. Cl.
CPC . *C12N 9/22* (2013.01); *C07K 14/31* (2013.01); *C12N 9/1241* (2013.01); *C12N 9/90* (2013.01); *C07K 2319/03* (2013.01)

(58) Field of Classification Search
CPC ........ C12Q 1/68; C12Q 1/6813; C40B 50/00; C07K 1/00; C07K 1/10
USPC ..................... 435/6.1, 6.11; 506/23
See application file for complete search history.

(56) References Cited

U.S. PATENT DOCUMENTS

| 5,561,043 | A * | 10/1996 | Cantor et al. ................ 435/6.16 |
| 5,985,834 | A * | 11/1999 | Engel et al. ..................... 514/3.8 |
| 6,015,714 | A | 1/2000 | Baldarelli et al. |
| 6,251,610 | B1 | 6/2001 | Gupte et al. |
| 6,451,563 | B1 | 9/2002 | Wittig et al. |
| 2002/0028458 | A1 | 3/2002 | Lexow |
| 2003/0044816 | A1 | 3/2003 | Denison et al. |
| 2003/0087232 | A1* | 5/2003 | Christians et al. ................ 435/6 |
| 2003/0108902 | A1 | 6/2003 | Abarzua |
| 2003/0118595 | A1* | 6/2003 | Niemeyer et al. .......... 424/184.1 |
| 2003/0166137 | A1* | 9/2003 | Zuker et al. ................... 435/69.1 |
| 2004/0229315 | A1* | 11/2004 | Lee et al. ...................... 435/69.1 |
| 2005/0053961 | A1 | 3/2005 | Akeson et al. |
| 2005/0221316 | A1* | 10/2005 | Pedersen et al. .................. 435/6 |
| 2005/0260655 | A1 | 11/2005 | Liu et al. |
| 2007/0015182 | A1 | 1/2007 | Abarzua |
| 2007/0122885 | A1* | 5/2007 | Reeves ..................... C12N 1/28 435/76 |
| 2008/0166724 | A1* | 7/2008 | Gerber ................... C07K 14/47 435/6.16 |
| 2008/0206252 | A1* | 8/2008 | Pennica ................. C07K 14/47 424/139.1 |
| 2009/0256116 | A1* | 10/2009 | Shumaker-Parry .. C09K 11/565 252/301.18 |
| 2009/0298075 | A1 | 12/2009 | Travers et al. |
| 2010/0221212 | A1* | 9/2010 | Stagliano ........... G01N 33/6866 424/85.4 |
| 2011/0019186 | A1* | 1/2011 | Himmelhaus ........ G01N 21/648 356/317 |
| 2013/0143802 | A1* | 6/2013 | Chilkoti ............. A61K 38/1709 514/6.2 |
| 2013/0195908 | A1* | 8/2013 | Leonetti ................. C07K 16/18 424/192.1 |

(Continued)

FOREIGN PATENT DOCUMENTS

| GB | 2130219 | 5/1984 |
| GB | 2453377 | 4/2009 |
| JP | 11-137260 | 5/1999 |

(Continued)

OTHER PUBLICATIONS

Kanan et al. Reaction discovery enabled by DNA-templated synthesis and in vitro selection. Nature 431 : 545 (2004).*

(Continued)

*Primary Examiner* — Ethan C Whisenant
(74) *Attorney, Agent, or Firm* — Nelson Mullins Riley & Scarborough LLP; Jane E. Remillard, Esq.; Christopher L. Frank

(57) ABSTRACT

The invention provides method of covalently coupling two or more moieties, the method comprising: (a) providing a first moiety having covalently attached thereto (i) at least one first linker comprising a first hybridizable region and (ii) at least one first group capable of forming a covalent bond; (b) providing a second moiety having covalently attached thereto (i) at least one second linker comprising a second hybridizable region capable of hybridizing to the first hybridizable region and (ii) at least a second group capable of forming a covalent bond with the first group; (c) contacting the first and second moieties under conditions that allow the first and second hybridizable regions to hybridize and link the moieties; and (d) exposing the linked moieties to conditions that allow the formation of a covalent bond between the first and second groups.

14 Claims, 6 Drawing Sheets

(56) References Cited

U.S. PATENT DOCUMENTS

| | | | | |
|---|---|---|---|---|
| 2014/0206842 A1* | 7/2014 | Majeed | ............ | C07K 7/06 530/345 |
| 2015/0175663 A1* | 6/2015 | Yokoi | ............ | A61K 38/00 530/327 |

FOREIGN PATENT DOCUMENTS

| WO | 01/40516 A2 | 6/2001 |
|---|---|---|
| WO | 02/42496 A2 | 5/2002 |
| WO | 03/012146 A1 | 2/2003 |
| WO | 2005/056750 A2 | 6/2005 |
| WO | 2006/028508 A2 | 3/2006 |
| WO | 2007/057668 A1 | 5/2007 |
| WO | 2007/075987 A2 | 7/2007 |
| WO | 2008/045575 A2 | 4/2008 |
| WO | 2008/083554 A1 | 7/2008 |
| WO | 2008/124107 A1 | 10/2008 |
| WO | 2010/004265 A1 | 1/2010 |

OTHER PUBLICATIONS

Avrameas et al., The Cross-Linking of Proteins with Glutaraldehyde and its use for the Preparation of Immunoadsorbants. Immunochemistry 6:53 (1969).*

Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).

Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc., vol. 128:1705-1710 (2006).

Bayley, Hagan et al., "Stochastic sensors inspired by biology," Nature, vol. 413:226-230 (2001).

Braha, Orit et al., "Carriers versus Adapters in Stochastic Sensing," ChemPhysChem, vol. 6:889-892 (2005).

Braha, Orit et al., "Designed protein pores as components for biosensors," Chemistry & Biology, vol. 4:497-505 (1997).

Branton, Daniel et al., "The potential and challenges of nanopore sequencing," Nat. Biotechnol., vol. 26 (10):1146-1153 (2008).

Eid, John et al., "Real-Time DNA Sequencing from Single Polymerase Molecules," Science, vol. 323:133-138 (2009).

Erie, Dorothy et al., "A Dumbell-Shaped, Double-Hairpin Structure of DNA: A Thermodynamic Investigation," Biochemistry, vol. 26:7150-7159 (1987).

Flusberg, Benjamin A. et al., "Direct detection of DNA methylation during single-molecule, real-time sequencing," Nature Methods, vol. 7(6):461-465 (2010).

Gu, Li-Qun et al., "Stochastic sensing of organic analytes by a pore-forming protein containing a molecular adapter," Nature, vol. 398:686-690 (1999).

Guan, Xiyun et al., "Stochastic Sensing of TNT with a Genetically Engineered Pore," ChemBioChem., vol. 6:1875-1881 (2005).

Hein, Christopher D. et al., "Click Chemistry, a Powerful Tool for Pharmaceutical Sciences," Pharm. Res., vol. 25 (10):2216-2230 (2008).

Hornblower, Breton et al., "Single-molecule analysis of DNA-protein complexes using nanopores," Nature Methods, vol. 4(4):315-317 (2007).

Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).

Kocalka, Petr et al., "Rapid and Efficient DNA Strand Cross-Linking by Click Chemistry," ChemBioChem, vol. 9:1280-1285 (2008).

Kolb, Hartmuth C. et al., "Click Chemistry: Diverse Chemical Function from a Few Good Reactions," Angew. Chem. Int. Ed., vol. 40:2004-2021 (2001).

Lovrinovic, Marina et al., "Rapid synthesis of DNA-cysteine conjugates for expressed protein ligation," Biochemical and Biophysical Research Communications, vol. 335:943-948 (2005).

Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).

Muller, Joachim et al., "DNA-directed assembly of artificial multienzyme complexes," Biochemical and Biophysical Research Communications, vol. 377:62-67 (2008).

Niemeyer, Christof M. et al., "DNA-Directed Assembly of Bienzymic Complexes from In Vivo Biotinylated NAD(P)H: FMN Oxidoreductase and Luciferase," ChemBioChem., vol. 3:242-245 (2002).

Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).

Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).

Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).

Sanchez-Quesada, Jorge et al., "Cyclic Peptides as Molecular Adapters for a Pore-Forming Protein," Journal of the American Chemical Society, vol. 122(48):11757-11766 (2000).

Seeman, Nadrian C., "Nucleic Acid Junctions and Lattices," J. theor. Biol., vol. 99:237-247 (1982).

Seo, Tae Seok et al., "Click Chemistry to Construct Fluorescent Oligonucleotides for DNA Sequencing," J. Org. Chem., vol. 68:609-612 (2003).

Shin, Seong-Ho et al., "Kinetics of a Reversible Covalent-Bond-Forming Reaction Observed at the Single-Molecule Level," Angew. Chem. Int. Ed., vol. 41(19):3707-3709 (2002).

Travers, Kevin J. et al., "A flexible and efficient template format for circular consensus sequencing and SNP detection," Nucleic Acids Research, vol. 38(15):e159, doi:10.1093/nar/gkq543 (2010).

Tung, Ching-Hsuan, "Preparation and Applications of Peptide-Oligonucleotide Conjugates," Bioconjugate Chemistry, vol. 11(5):605-618 (2000).

Wang, Qian et al., "Bioconjugation by Copper(I)-Catalyzed Azide-Alkyne [3+2] Cycloaddition," J. Am. Chem. Soc., vol. 125:3192-3193 (2003).

Wemmer, David E. et al., "Preparation and melting of single strand circular DNA loops," Nucleic Acids Research, vol. 13(23):8611-8621 (1985).

* cited by examiner

SEQUENCE LISTING

<160> NUMBER OF SEQ ID NOS: 78

<210> SEQ ID NO 1
<211> LENGTH: 882
<212> TYPE: DNA
<213> ORGANISM: Staphylococcus aureus

<400> SEQUENCE: 1

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
```

```
tggccttcag cctttaaggt acagttgcaa ctacctgata atgaagtagc tcaaatatct    300
gattactatc caagaaattc gattgataca aagagtata  tgagtacttt aacttatgga    360
ttcaacggta atgttactgg tgatgataca ggaaaaattg gcggccttat tggtgcaaat    420
gtttcgattg gtcatacact gaaatatgtt caacctgatt tcaaaacaat tttagagagc    480
ccaactgata aaaagtagg  ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga gtaatatac  gaacgagttc gtgatgatta ccaattgcat    780
tggacttcaa caaattggaa aggtaccaat actaaagata aatggacaga tcgttcttca    840
gaaagatata aaatcgattg ggaaaagaa  gaaatgacaa at                       882

<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

Gln Leu His Trp Thr Ser Thr Asn Trp Lys Gly Asn Thr Lys Asp
                    260                 265                 270

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 3
<211> LENGTH: 882
<212> TYPE: DNA
<213> ORGANISM: Artificial sequence
<220> FEATURE:
<223> OTHER INFORMATION: a-HL L135C/N139Q

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300
gattactatc caagaaattc gattgataca aaagagtata tgagtacttt aacttatgga     360
ttcaacggta atgttactgg tgatgataca ggaaaaattg gcggctgtat tggtgcacaa     420
gtttcgattg gtcatacact gaaatatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca tcaactttt catgaaaact      600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga gtaatatac gaacgagttc gtgatgatta ccaattgcat      780
tggacttcaa caaattggaa aggtaccaat actaaagata aatggacaga tcgttcttca     840
gaaagatata aaatcgattg ggaaaaagaa gaaatgacaa at                        882
```

<210> SEQ ID NO 4
<211> LENGTH: 293
<212> TYPE: PRT
<213> ORGANISM: Artificial sequence
<220> FEATURE:
<223> OTHER INFORMATION: a-HL L135C/N139Q

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

```
Met Ser Thr Leu Thr Tyr Gly Phe Asn Gly Asn Val Thr Gly Asp Asp
        115                 120                 125

Thr Gly Lys Ile Gly Gly Cys Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 5
<211> LENGTH: 1390
<212> TYPE: DNA
<213> ORGANISM: Escherichia. coli

<400> SEQUENCE: 5
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccggaa gagtgtttat tgcaaaccgg ccgatgatta tctgccgcag     180
ccgggtgcgg tgctgattac cggtattacc cgcaggaag cgcgcgcgaa aggtgaaaac      240
gaagcggcgt tgccgcgcg cattcatagc ctgtttaccg tgccgaaaac ctgcattctg      300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcgt gctatgcgct gcgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc accgtaaca aacacaaact gatggcgctg      660
attgatgttc gcagatgaa accgctggtg catgtgagcg gcatgtttgg cgcctggcgc      720
ggcaacacca gctgggtggc cccgctggcc tggcacccgg aaaatcgtaa cgccgtgatt     780
atggttgatc tggccggtga tattagcccg ctgctggaac tggatagcga taccctgcgt     840
gaacgcctgt ataccgccaa aaccgatctg ggcgataatg ccgccgtgcc ggtgaaactg     900
gttcacatta caaatgcccg gtgctggcc caggcgaaca ccctgcgccc ggaagatgcg      960
gatcgtctgg gtattaatcg ccagcattgt ctggataatc tgaaaatcct gcgtgaaaac    1020
```

-continued

```
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca attttccggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc                                                            1390
```

<210> SEQ ID NO 6
<211> LENGTH: 485
<212> TYPE: PRT
<213> ORGANISM: Escherichia. coli

<400> SEQUENCE: 6

```
Met Met Asn Asp Gly Lys Gln Gln Ser Thr Phe Leu Phe His Asp Tyr
  1               5                  10                  15

Glu Thr Phe Gly Thr His Pro Ala Leu Asp Arg Pro Ala Gln Phe Ala
                 20                  25                  30

Ala Ile Arg Thr Asp Ser Glu Phe Asn Val Ile Gly Glu Pro Glu Val
             35                  40                  45

Phe Tyr Cys Lys Pro Ala Asp Asp Tyr Leu Pro Gln Pro Gly Ala Val
 50                  55                  60

Leu Ile Thr Gly Ile Thr Pro Gln Glu Ala Arg Ala Lys Gly Glu Asn
 65                  70                  75                  80

Glu Ala Ala Phe Ala Ala Arg Ile His Ser Leu Phe Thr Val Pro Lys
                 85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
            115                 120                 125

Gln His Asp Asn Ser Arg Trp Asp Leu Leu Asp Val Met Arg Ala Cys
        130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300
```

```
Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
            325                 330                 335

Leu Arg Glu Asn Pro Gln Val Arg Glu Lys Val Val Ala Ile Phe Ala
                340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
        370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
                435                 440                 445

Met Leu Val Gln Gln Tyr Ala Asp Asp Lys Glu Lys Val Ala Leu Leu
        450                 455                 460

Lys Ala Leu Trp Gln Tyr Ala Glu Glu Ile Val Ser Gly Ser Gly His
465                 470                 475                 480

His His His His His
            485

<210> SEQ ID NO 7
<211> LENGTH: 1455
<212> TYPE: DNA
<213> ORGANISM: Artificial sequence
<220> FEATURE:
<223> OTHER INFORMATION: EcoExo I C98S/C306S/C330T/C51A (ONLD0393)

<400> SEQUENCE: 7
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccgga agtgttttat gcgaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac cagcattctg     300
ggctataaca atgtgcgctt cgatgatgaa gttacccgta atatcttta tcgtaacttt     360 tatgatccgt atgcgtggag ctggcagcat gataacagcc gttgggatct gctggatgtg     420
atgcgcgcgt gctatgcgct cgccccggaa ggcattaatt ggccggaaaa cgatgatggc     480
ctgccgagct tcgtctggaa catctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc accgtaaca aacacaaact gatggcgctg     660
attgatgttc gcagatgaa accgctggtg catgtgagcg gcatgtttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga taccctgcgt     840
gaacgcctgt ataccgccaa accgatctg ggcgataatg ccgccgtgcc ggtgaaactg     900
gttcacatta caaaagccc ggtgctggcc caggcgaaca ccctgcgccc ggaagatgcg     960
gatcgtctgg gtattaatcg ccagcatacc ctggataatc tgaaaatcct gcgtgaaaac    1020
```

-continued

```
ccgcaggtgc gtgaaaaagt ggtggcgatc ttcgcggaag cggaaccgtt cacccccgagc   1080 gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                     1455
```

<210> SEQ ID NO 8
<211> LENGTH: 485
<212> TYPE: PRT
<213> ORGANISM: Artificial sequence
<220> FEATURE:
<223> OTHER INFORMATION: EcoExo I C98S/C306S/C330T/C51A (ONLD0393)

<400> SEQUENCE: 8

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
                20                  25                  30

Ala Ile Arg Thr Asp Ser Glu Phe Asn Val Ile Gly Glu Pro Glu Val
            35                  40                  45

Phe Tyr Ala Lys Pro Ala Asp Asp Tyr Leu Pro Gln Pro Gly Ala Val
50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
```

```
                275                 280                 285
Asp Leu Gly Asp Asn Ala Ala Val Pro Val Lys Leu Val His Ile Asn
            290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 9
<211> LENGTH: 1455
<212> TYPE: DNA
<213> ORGANISM: Artificial sequence
<220> FEATURE:
<223> OTHER INFORMATION: EcoExo I C98S/C306S/C330T/C144M (ONLD0403)

<400> SEQUENCE: 9
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt ttgccgcgcg cattcatagc ctgtttaccg tgccgaaaac cagcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcga tgtatgcgct cgcccggaa ggcattaatt ggccggaaaa cgatgatggc     480
ctgccgagct tcgtctggaa acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc accgtaaca aacacaaact gatggcgctg     660
attgatgttc gcagatgaa accgctggtg catgtgagcg gcatgtttgg cgcctggcgc     720
ggcaacacca gctgggtggc cccgctgccc tggcacccgg aaaatcgtaa cgccgtgatt     780
atggttgatc tggccggtga tattagcccg ctgctggaac tggatagcga taccctgcgt     840
```

```
gaacgcctgt ataccgccaa aaccgatctg gcgataatg ccgccgtgcc ggtgaaactg      900
gttcacatta acaaaagccc ggtgctggcc caggcgaaca ccctgcgccc ggaagatgcg      960
gatcgtctgg gtattaatcg ccagcatacc ctggataatc tgaaaatcct gcgtgaaaac     1020
ccgcaggtgc gtgaaaaagt ggtggcgatc ttcgcggaag cggaaccgtt caccccgagc     1080
gataacgtgg atgcgcagct gtataacggc ttctttagcg atgccgatcg cgcggcgatg     1140
aaaatcgttc tggaaaccga accgcgcaat ctgccggcgc tggatattac ctttgttgat     1200
aaacgtattg aaaaactgct gtttaattat cgtgcgcgca attttccggg tacccctgga t     1260 tatgccgaac agcagcgttg gctggaacat cgtcgtcagg ttttcacccc ggaatttctg     1320
cagggttatg cggatgaact gcagatgctg gttcagcagt atgccgatga taaagaaaaa     1380
gtggcgctgc tgaaagcgct gtggcagtat gcggaagaaa tcgtttctgg ctctggtcac     1440
catcatcatc accac                                                     1455
```

<210> SEQ ID NO 10
<211> LENGTH: 485
<212> TYPE: PRT
<213> ORGANISM: Artificial sequence
<220> FEATURE:
<223> OTHER INFORMATION: 10 EcoExo I C98S/C306S/C330T/C144M (ONLD0403)

<400> SEQUENCE: 10

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Met
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255
```

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
            290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
        370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
        450                 455                 460

Lys Ala Leu Trp Gln Tyr Ala Glu Glu Ile Val Ser Gly Ser Gly His
465                 470                 475                 480

His His His His His
            485

<210> SEQ ID NO 11
<211> LENGTH: 1455
<212> TYPE: DNA
<213> ORGANISM: Artificial sequence
<220> FEATURE:
<223> OTHER INFORMATION: 11 EcoExo I C98S/C306S/C330T/C144T (ONLD0404)

<400> SEQUENCE: 11
atgatgaacg atggcaaaca gcagagcacc ttcctgtttc atgattatga aaccttcggt       60
acccatccgg ccctggatcg tccggcgcag tttgcggcca ttcgcaccga tagcgaattc      120
aatgtgattg cgaaccgga agtgttttat tgcaaaccgg ccgatgatta tctgccgcag      180
ccgggtgcgg tgctgattac cggtattacc ccgcaggaag cgcgcgcgaa aggtgaaaac      240
gaagcggcgt tgccgcgcg cattcatagc ctgtttaccg tgccgaaaac cagcattctg      300
ggctataaca atgtgcgctt cgatgatgaa gttacccgta atatctttta tcgtaacttt      360
tatgatccgt atgcgtggag ctggcagcat gataacagcc gttgggatct gctggatgtg      420
atgcgcgcga cctatgcgct cgcccggaa ggcattaatt ggccggaaaa cgatgatggc      480
ctgccgagct tcgtctggga acatctgacc aaagccaacg gcattgaaca tagcaatgcc      540
catgatgcga tggccgatgt ttatgcgacc attgcgatgg cgaaactggt taaaacccgt      600
cagccgcgcc tgtttgatta ctgtgttacc accgtaacaa acacaaaact gatggcgctg      660
attgatgttc gcagatgaa accgctggtg catgtgagcg gcatgtttgg cgcctggcgc      720

```
ggcaacacca gctgggtggc cccgctggcc tggcacccgg aaaatcgtaa cgccgtgatt    780
atggttgatc tggccggtga tattagcccg ctgctggaac tggatagcga tacccctgcgt   840 gaacgcctgt ataccgccaa aaccgatctg ggcgataatg ccgccgtgcc ggtgaaactg    900
gttcacatta caaaagccc ggtgctggcc caggcgaaca ccctgcgccc ggaagatgcg     960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt cacccccgagc 1080 gataacgtgg atgcgcagct gtataacggc ttctttagcg atgccgatcg cgcggcgatg  1140
aaaatcgttc tggaaaccga accgcgcaat ctgccggcgc tggatattac ctttgttgat  1200
aaacgtattg aaaaactgct gtttaattat cgtgcgcgca attttccggg taccctggat  1260
tatgccgaac agcagcgttg gctggaacat cgtcgtcagg ttttcacccc ggaatttctg  1320
cagggttatg cggatgaact gcagatgctg gttcagcagt atgccgatga taagaaaaaa  1380
gtggcgctgc tgaaagcgct gtggcagtat gcggaagaaa tcgtttctgg ctctggtcac  1440
catcatcatc accac                                                    1455
```

<210> SEQ ID NO 12  
<211> LENGTH: 485  
<212> TYPE: PRT  
<213> ORGANISM: Artificial sequence  
<220> FEATURE:  
<223> OTHER INFORMATION: EcoExo I C98S/C306S/C330T/C144T (ONLD0404)

<400> SEQUENCE: 12

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220
```

```
Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
            245                 250                 255

Asn Ala Val Ile Met Val Asp Leu Ala Gly Asp Ile Ser Pro Leu Leu
        260                 265                 270

Glu Leu Asp Ser Asp Thr Leu Arg Glu Arg Leu Tyr Thr Ala Lys Thr
    275                 280                 285

Asp Leu Gly Asp Asn Ala Ala Val Pro Val Lys Leu Val His Ile Asn
290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
            325                 330                 335

Leu Arg Glu Asn Pro Gln Val Arg Glu Lys Val Val Ala Ile Phe Ala
        340                 345                 350

Glu Ala Glu Pro Phe Thr Pro Ser Asp Asn Val Asp Ala Gln Leu Tyr
    355                 360                 365

Asn Gly Phe Phe Ser Asp Ala Asp Arg Ala Ala Met Lys Ile Val Leu
370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
        420                 425                 430

Gln Val Phe Thr Pro Glu Phe Leu Gln Gly Tyr Ala Asp Glu Leu Gln
    435                 440                 445

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
465                 470                 475                 480

His His His His His
                485

<210> SEQ ID NO 13
<211> LENGTH: 1455
<212> TYPE: DNA
<213> ORGANISM: Artificial sequence
<220> FEATURE:
<223> OTHER INFORMATION: EcoExo I C51A/C98S/C144M/C306S/C330T/V42C
      (ONLD0415)

<400> SEQUENCE: 13
atgatgaacg atggcaaaca gcagagcacc ttcctgtttc atgattatga aaccttcggt        60
acccatccgg ccctggatcg tccggcgcag tttgcggcca ttcgcaccga tagcgaattc       120
aattgcattg gcgaaccgga agtgttttat gcgaaaccgg ccgatgatta ctgccgcag       180 ccgggtgcgg tgctgattac cggtattacc ccgcaggaag cgcgcgcgaa aggtgaaaac       240
gaagcggcgt tgccgcgcg cattcatagc ctgtttaccg tgccgaaaac cagcattctg       300
ggctataaca tgtgcgcttc gatgatgaa gttacccgta atatctttta tcgtaacttt       360
tatgatccgt atgcgtggag ctggcagcat gataacagcc gttgggatct gctggatgtg       420
atgcgcgcga tgtatgcgct cgcccgggaa ggcattaatt ggccggaaaa cgatgatggc       480
ctgccgagct ttcgtctgga acatctgacc aaagccaacg gcattgaaca tagcaatgcc       540
```

```
catgatgcga tggccgatgt ttatgcgacc attgcgatgg cgaaactggt taaaacccgt    600
cagccgcgcc tgtttgatta tctgtttacc caccgtaaca acacaaaact gatggcgctg    660
attgatgttc cgcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg gcgataatg ccgccgtgcc ggtgaaactg    900
gttcacatta caaaagcccc ggtgctggcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 14
<211> LENGTH: 485
<212> TYPE: PRT
<213> ORGANISM: Artificial sequence
<220> FEATURE:
<223> OTHER INFORMATION: EcoExo I C51A/C98S/C144M/C306S/C330T/V42C
      (ONLD0415)

<400> SEQUENCE: 14

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Cys Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Met
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190
```

```
Met Ala Lys Leu Val Lys Thr Arg Gln Pro Arg Leu Phe Asp Tyr Leu
        195                 200                 205
Phe Thr His Arg Asn Lys His Lys Leu Met Ala Leu Ile Asp Val Pro
    210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
Asp Leu Gly Asp Asn Ala Ala Val Pro Val Lys Leu Val His Ile Asn
    290                 295                 300
Lys Ser Pro Val Leu Ala Gln Ala Asn Thr Leu Arg Pro Glu Asp Ala
305                 310                 315                 320
Asp Arg Leu Gly Ile Asn Arg Gln His Thr Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
    370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
        435                 440                 445
Met Leu Val Gln Gln Tyr Ala Asp Asp Lys Glu Lys Val Ala Leu Leu
    450                 455                 460
Lys Ala Leu Trp Gln Tyr Ala Glu Glu Ile Val Ser Gly Ser Gly His
465                 470                 475                 480
His His His His
            485

<210> SEQ ID NO 15
<211> LENGTH: 1455
<212> TYPE: DNA
<213> ORGANISM: Artificial sequence
<220> FEATURE:
<223> OTHER INFORMATION: EcoExo I C51A/C98S/C144T/C306S/C330T/V42C
      (ONLD0416)

<400> SEQUENCE: 15
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aattgcattg gcgaaccgga agtgttttat gcgaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac cagcattctg     300
```

-continued

```
ggctataaca atgtgcgctt cgatgatgaa gttacccgta atatctttta tcgtaacttt    360
tatgatccgt atgcgtggag ctggcagcat gataacagcc gttgggatct gctggatgtg    420
atgcgcgcga cctatgcgct cgcccggaa ggcattaatt ggccggaaaa cgatgatggc    480
ctgccgagct tcgtctgga acatctgacc aaagccaacg gcattgaaca tagcaatgcc    540
catgatgcga tggccgatgt ttatgcgacc attgcgatgg cgaaactggt taaacccgt    600
cagccgcgcc tgtttgatta tctgtttacc caccgtaaca acacaaaact gatgcgctg    660
attgatgttc cgcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta caaaagccc ggtgctgcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt cacccccgagc  1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                   1455
```

<210> SEQ ID NO 16
<211> LENGTH: 485
<212> TYPE: PRT
<213> ORGANISM: Artificial sequence
<220> FEATURE:
<223> OTHER INFORMATION: EcoExo I C51A/C98S/C144T/C306S/C330T/V42C
    (ONLD0416)

<400> SEQUENCE: 16

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Cys Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Met
    130                 135                 140

Tyr Ala Leu Arg Pro Glu Gly Ile Asn Trp Pro Glu Asn Asp Asp Gly
```

```
                145                 150                 155                 160
Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
                180                 185                 190

Met Ala Lys Leu Val Lys Thr Arg Gln Pro Arg Leu Phe Asp Tyr Leu
                195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
                260                 265                 270

Glu Leu Asp Ser Asp Thr Leu Arg Glu Arg Leu Tyr Thr Ala Lys Thr
                275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
                340                 345                 350

Glu Ala Glu Pro Phe Thr Pro Ser Asp Asn Val Asp Ala Gln Leu Tyr
                355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
                420                 425                 430

Gln Val Phe Thr Pro Glu Phe Leu Gln Gly Tyr Ala Asp Glu Leu Gln
                435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His
        485

<210> SEQ ID NO 17
<211> LENGTH: 1455
<212> TYPE: DNA
<213> ORGANISM: Artificial sequence
<220> FEATURE:
<223> OTHER INFORMATION: EcoExo I C51A/C98S/C144M/C306S/C330T/M184C
      (ONLD0417)

<400> SEQUENCE: 17
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
```

```
aatgtgattg gcgaaccgga agtgttttat gcgaaaccgg ccgatgatta tctgccgcag      180
ccgggtgcgg tgctgattac cggtattacc ccgcaggaag cgcgcgcgaa aggtgaaaac      240
gaagcggcgt tgccgcgcg cattcatagc ctgtttaccg tgccgaaaac cagcattctg       300
ggctataaca atgtgcgctt cgatgatgaa gttacccgta atatctttta tcgtaacttt      360
tatgatccgt atgcgtggag ctggcagcat gataacagcc gttgggatct gctggatgtg     420
atgcgcgcga tgtatgcgct cgcccggaa ggcattaatt ggccggaaaa cgatgatggc       480
ctgccgagct ttcgtctgga acatctgacc aaagccaacg gcattgaaca tagcaatgcc     540
catgatgcgt gcgccgatgt ttatgcgacc attgcgatgg cgaaactggt taaaacccgt     600
cagccgcgcc tgtttgatta tctgtttacc caccgtaaca acacaaaact gatggcgctg      660
attgatgttc gcagatgaa accgctggtg catgtgagcg gcatgtttgg cgcctggcgc      720
ggcaacacca gctgggtggc cccgctggcc tggcacccgg aaaatcgtaa cgccgtgatt     780
atggttgatc tggccggtga tattagcccg ctgctggaac tggatagcga tacccctgcgt    840 gaacgcctgt ataccgccaa aaccgatctg gcgataatg ccgccgtgcc ggtgaaactg       900
gttcacatta caaaagccc ggtgctggcc caggcgaaca ccctgcgccc ggaagatgcg       960
gatcgtctgg gtattaatcg ccagcatacc ctggataatc tgaaaatcct gcgtgaaaac     1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca ttttccgggg tacctggat     1260 tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc tgaaagcgct gtggcagtat gcggaagaaa tcgtttctgg ctctggtcac    1440
catcatcatc accac                                                     1455
```

<210> SEQ ID NO 18
<211> LENGTH: 485
<212> TYPE: PRT
<213> ORGANISM: Artificial sequence
<220> FEATURE:
<223> OTHER INFORMATION: EcoExo I C51A/C98S/C144M/C306S/C330T/M184C
      (ONLD0417)

<400> SEQUENCE: 18

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110
```

```
Arg Asn Ile Phe Tyr Arg Asn Phe Tyr Asp Pro Tyr Ala Trp Ser Trp
            115                 120                 125

Gln His Asp Asn Ser Arg Trp Asp Leu Leu Asp Val Met Arg Ala Met
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Cys Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 19
<211> LENGTH: 1455
<212> TYPE: DNA
<213> ORGANISM: Artificial sequence
<220> FEATURE:
<223> OTHER INFORMATION: EcoExo I C51A/C98S/C144T/C306S/C330T/M184C
```

(ONLD0418)

<400> SEQUENCE: 19

| | | | | | |
|---|---|---|---|---|---|
| atgatgaacg | atggcaaaca | gcagagcacc | ttcctgtttc | atgattatga | aaccttcggt | 60 |
| acccatccgg | ccctggatcg | tccggcgcag | tttgcggcca | ttcgcaccga | tagcgaattc | 120 |
| aatgtgattg | gcgaaccgga | agtgttttat | gcgaaaccgg | ccgatgatta | tctgccgcag | 180 |
| ccgggtgcgg | tgctgattac | cggtattacc | ccgcaggaag | cgcgcgcgaa | aggtgaaaac | 240 |
| gaagcggcgt | tgccgcgcg | cattcatagc | ctgtttaccg | tgccgaaaac | cagcattctg | 300 |
| ggctataaca | atgtgcgctt | cgatgatgaa | gttacccgta | atatctttta | tcgtaacttt | 360 |
| tatgatccgt | atgcgtggag | ctggcagcat | gataacagcc | gttgggatct | gctggatgtg | 420 |
| atgcgcgcga | cctatgcgct | cgcccggaa | ggcattaatt | ggccgaaaa | cgatgatggc | 480 |
| ctgccgagct | ttcgtctgga | acatctgacc | aaagccaacg | gcattgaaca | tagcaatgcc | 540 |
| catgatgcgt | cgccgatgt | ttatgcgacc | attgcgatgg | cgaaactggt | taaaacccgt | 600 |
| cagccgcgcc | tgtttgatta | tctgtttacc | caccgtaaca | aacacaaact | gatggcgctg | 660 |
| attgatgttc | cgcagatgaa | accgctggtg | catgtgagcg | gcatgtttgg | cgcctggcgc | 720 |
| ggcaacacca | gctgggtggc | cccgctggcc | tggcacccgg | aaaatcgtaa | cgccgtgatt | 780 |
| atggttgatc | tggccggtga | tattagcccg | ctgctggaac | tggatagcga | taccctgcgt | 840 |
| gaacgcctgt | ataccgccaa | aaccgatctg | ggcgataatg | ccgccgtgcc | ggtgaaactg | 900 |
| gttcacatta | caaaagccc | ggtgctggcc | caggcgaaca | ccctgcgccc | ggaagatgcg | 960 |
| gatcgtctgg | gtattaatcg | ccagcatacc | ctggataatc | tgaaaatcct | gcgtgaaaac | 1020 |
| ccgcaggtgc | gtgaaaaagt | ggtggcgatc | ttcgcggaag | cggaaccgtt | caccccgagc | 1080 |
| gataacgtga | tgcgcagct | gtataacggc | ttctttagcg | atgccgatcg | cgcggcgatg | 1140 |
| aaaatcgttc | tggaaaccga | accgcgcaat | ctgccggcgc | tggatattac | ctttgttgat | 1200 |
| aaacgtattg | aaaaactgct | gtttaattat | cgtgcgcgca | atttccgggg | taccctggat | 1260 |
| tatgccgaac | agcagcgttg | gctggaacat | cgtcgtcagg | ttttcacccc | ggaatttctg | 1320 |
| cagggttatg | cggatgaact | gcagatgctg | gttcagcagt | atgccgatga | taagaaaaa | 1380 |
| gtggcgctgc | tgaaagcgct | gtggcagtat | gcggaagaaa | tcgtttctgg | ctctggtcac | 1440 |
| catcatcatc | accac | | | | | 1455 |

<210> SEQ ID NO 20
<211> LENGTH: 485
<212> TYPE: PRT
<213> ORGANISM: Artificial sequence
<220> FEATURE:
<223> OTHER INFORMATION: EcoExo I C51A/C98S/C144T/C306S/C330T/M184C
       (ONLD0418)

<400> SEQUENCE: 20

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

```
Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Cys Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His
            485
```

<210> SEQ ID NO 21
<211> LENGTH: 1455
<212> TYPE: DNA
<213> ORGANISM: Artificial sequence
<220> FEATURE:
<223> OTHER INFORMATION: EcoExo I C51A/C98S/C144T/C306S/C330T (ONLD0411)

<400> SEQUENCE: 21

| | |
|---|---|
| atgatgaacg atggcaaaca gcagagcacc ttcctgtttc atgattatga aaccttcggt | 60 |
| acccatccgg ccctggatcg tccggcgcag tttgcggcca ttcgcaccga tagcgaattc | 120 |
| aatgtgattg cgaaccgga agtgttttat gcgaaaccgg ccgatgatta tctgccgcag | 180 |
| ccgggtgcgg tgctgattac cggtattacc ccgcaggaag cgcgcgcgaa aggtgaaaac | 240 |
| gaagcggcgt tgccgcgcg cattcatagc ctgtttaccg tgccgaaaac cagcattctg | 300 |
| ggctataaca atgtgcgctt cgatgatgaa gttacccgta atatctttta tcgtaacttt | 360 |
| tatgatccgt atgcgtggag ctggcagcat gataacagcc gttgggatct gctggatgtg | 420 |
| atgcgcgcga cctatgcgct cgccccggaa ggcattaatt ggccgaaaaa cgatgatggc | 480 |
| ctgccgagct tcgtctggga acatctgacc aaagccaacg gcattgaaca tagcaatgcc | 540 |
| catgatgcga tggccgatgt ttatgcgacc attgcgatgg cgaaactggt taaaacccgt | 600 |
| cagccgcgcc tgtttgatta tctgtttacc caccgtaaca aacacaaact gatggcgctg | 660 |
| attgatgttc gcagatgaa accgctggtg catgtgagcg catgtttgg cgcctggcgc | 720 |
| ggcaacacca gctgggtggc cccgctggcc tggcacccgg aaaatcgtaa cgccgtgatt | 780 |
| atggttgatc tggccggtga tattagcccg ctgctggaac tggatagcga tacccctgcgt | 840 |
| gaacgcctgt ataccgccaa aaccgatctg ggcgataatg ccgccgtgcc ggtgaaactg | 900 |
| gttcacatta caaaaagccc ggtgctggcc caggcgaaca ccctgcgccc ggaagatgcg | 960 |
| gatcgtctgg gtattaatcg ccagcatacc ctggataatc tgaaaatcct gcgtgaaaac | 1020 |
| ccgcaggtgc gtgaaaaagt ggtggcgatc ttcgcggaag cggaaccgtt caccccgagc | 1080 |
| gataacgtgg atgcgcagct gtataacggc ttctttagcg atgccgatcg cgcggcgatg | 1140 |
| aaaatcgttc tggaaaccga accgcgcaat ctgccggcgc tggatattac ctttgttgat | 1200 |
| aaacgtattg aaaaactgct gtttaattat cgtgcgcgca attttccggg tacccctggat | 1260 |
| tatgccgaac agcagcgttg gctggaacat cgtcgtcagg ttttcacccc ggaatttctg | 1320 |
| cagggttatg cggatgaact gcagatgctg gttcagcagt atgccgatga taaagaaaaa | 1380 |
| gtggcgctgc tgaaagcgct gtggcagtat gcggaagaaa tcgtttctgg ctctggtcac | 1440 |
| catcatcatc accac | 1455 |

<210> SEQ ID NO 22
<211> LENGTH: 485
<212> TYPE: PRT
<213> ORGANISM: Artificial sequence
<220> FEATURE:
<223> OTHER INFORMATION: EcoExo I C51A/C98S/C144T/C306S/C330T (ONLD0411)

<400> SEQUENCE: 22

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

```
Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Ser Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
                115                 120                 125

Gln His Asp Asn Ser Arg Trp Asp Leu Leu Asp Val Met Arg Ala Thr
            130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
            195                 200                 205

Phe Thr His Arg Asn Lys His Lys Leu Met Ala Leu Ile Asp Val Pro
210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
            290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Arg Trp Leu Glu His Arg Arg
            420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
```

```
                   465                 470                 475                 480

His His His His His
                 485

<210> SEQ ID NO 23
<211> LENGTH: 1455
<212> TYPE: DNA
<213> ORGANISM: Artificial sequence
<220> FEATURE:
<223> OTHER INFORMATION: EcoExo I C51A/C98T/C144T/C306S/C330T (ONLD0432)

<400> SEQUENCE: 23
atgatgaacg atggcaaaca gcagagcacc ttcctgtttc atgattatga aaccttcggt        60
acccatccgg ccctggatcg tccggcgcag tttgcggcca ttcgcaccga tagcgaattc       120
aatgtgattg cgaaccgga  agtgttttat gcgaaaccgg ccgatgatta tctgccgcag       180
ccgggtgcgg tgctgattac cggtattacc ccgcaggaag cgcgcgcgaa aggtgaaaac       240
gaagcggcgt tgccgcgcg  cattcatagc ctgtttaccg tgccgaaaac caccattctg       300
ggctataaca atgtgcgctt cgatgatgaa gttacccgta atatctttta tcgtaacttt       360
tatgatccgt atgcgtggag ctggcagcat gataacagcc gttgggatct gctggatgtg       420
atgcgcgcga cctatgcgct cgccccggaa ggcattaatt ggccggaaaa cgatgatggc       480
ctgccgagct tcgtctggaa acatctgacc aaagccaacg gcattgaaca tagcaatgcc       540
catgatgcga tggccgatgt ttatgcgacc attgcgatgg cgaaactggt taaacccgt        600 cagccgcgcc tgtttgatta tctgtttacc caccgtaaca acacaaaact gatggcgctg       660
attgatgttc gcagatgaa  accgctggtg catgtgagcg gcatgtttgg cgcctggcgc       720
ggcaacacca gctgggtggc cccgctggcc tggcacccgg aaaatcgtaa cgccgtgatt       780
atggttgatc tggccggtga tattagcccg ctgctggaac tggatagcga tacccctgcgt       840 gaacgcctgt ataccgccaa aaccgatctg ggcgataatg ccgccgtgcc ggtgaaactg       900
gttcacatta caaaagcccc ggtgctggcc caggcgaaca ccctgcgccc ggaagatgcg       960
gatcgtctgg gtattaatcg ccagcatacc ctggataatc tgaaaatcct gcgtgaaaac      1020
ccgcaggtgc gtgaaaaagt ggtggcgatc ttcgcggaag cggaaccgtt cacccccgagc      1080 gataacgtgg atgcgcagct gtataacggc ttctttagcg atgccgatcg cgcggcgatg      1140
aaaatcgttc tggaaaccga accgcgcaat ctgccggcgc tggatattac ctttgttgat      1200
aaacgtattg aaaaactgct gtttaattat cgtgcgcgca attttccggg taccctggat      1260
tatgccgaac agcagcgttg gctgaacat  cgtcgtcagg ttttcacccc ggaatttctg      1320
cagggttatg cggatgaact gcagatgctg gttcagcagt atgccgatga taaagaaaaa      1380
gtggcgctgc tgaaagcgct gtggcagtat gcggaagaaa tcgtttctgg ctctggtcac      1440
catcatcatc accac                                                       1455

<210> SEQ ID NO 24
<211> LENGTH: 485
<212> TYPE: PRT
<213> ORGANISM: Artificial sequence
<220> FEATURE:
<223> OTHER INFORMATION: EcoExo I C51A/C98T/C144T/C306S/C330T (ONLD0432)

<400> SEQUENCE: 24

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
```

```
                    20                  25                  30
Ala Ile Arg Thr Asp Ser Glu Phe Asn Val Ile Gly Glu Pro Glu Val
                35                  40                  45

Phe Tyr Ala Lys Pro Ala Asp Asp Tyr Leu Pro Gln Pro Gly Ala Val
        50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
            115                 120                 125

Gln His Asp Asn Ser Arg Trp Asp Leu Leu Asp Val Met Arg Ala Thr
        130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445
```

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
465                 470                 475                 480

His His His His His
            485

<210> SEQ ID NO 25
<211> LENGTH: 1455
<212> TYPE: DNA
<213> ORGANISM: Artificial sequence
<220> FEATURE:
<223> OTHER INFORMATION: EcoExo I C51A/C98T/C144T/C306T/C330T (ONLD0433)

<400> SEQUENCE: 25

| | | | | | |
|---|---|---|---|---|---|
| atgatgaacg | atggcaaaca | gcagagcacc | ttcctgtttc | atgattatga | aaccttcggt | 60 |
| acccatccgg | ccctggatcg | tccggcgcag | tttgcggcca | ttcgcaccga | tagcgaattc | 120 |
| aatgtgattg | gcgaaccgga | agtgttttat | gcgaaaccgg | ccgatgatta | tctgccgcag | 180 |
| ccgggtgcgg | tgctgattac | cggtattacc | cgcaggaag | cgcgcgcgaa | aggtgaaaac | 240 |
| gaagcggcgt | ttgccgcgcg | cattcatagc | ctgtttaccg | tgccgaaaac | caccattctg | 300 |
| ggctataaca | atgtgcgctt | cgatgatgaa | gttacccgta | atatctttta | tcgtaacttt | 360 |
| tatgatccgt | atgcgtggag | ctggcagcat | gataacagcc | gttgggatct | gctggatgtg | 420 |
| atgcgcgcga | cctatgcgct | gcgcccggaa | ggcattaatt | ggccggaaaa | cgatgatggc | 480 |
| ctgccgagct | ttcgtctgga | acatctgacc | aaagccaacg | gcattgaaca | tagcaatgcc | 540 |
| catgatgcga | tggccgatgt | ttatgcgacc | attgcgatgg | cgaaactggt | taaaacccgt | 600 |
| cagccgcgcc | tgtttgatta | tctgtttacc | caccgtaaca | aacacaaact | gatggcgctg | 660 |
| attgatgttc | gcagatgaa | accgctggtg | catgtgagcg | gcatgtttgg | cgcctggcgc | 720 |
| ggcaacacca | gctgggtggc | cccgctggcc | tggcacccgg | aaaatcgtaa | cgccgtgatt | 780 |
| atggttgatc | tggccggtga | tattagcccg | ctgctggaac | tggatagcga | taccctgcgt | 840 |
| gaacgcctgt | ataccgccaa | aaccgatctg | gcgataatg | ccgccgtgcc | ggtgaaactg | 900 |
| gttcacatta | caaaaacccc | ggtgctggcc | caggcgaaca | ccctgcgccc | ggaagatgcg | 960 |
| gatcgtctgg | gtattaatcg | ccagcatacc | ctggataatc | tgaaaatcct | gcgtgaaaac | 1020 |
| ccgcaggtgc | gtgaaaaagt | ggtggcgatc | ttcgcggaag | cggaaccgtt | caccccgagc | 1080 |
| gataacgtgg | atgcgcagct | gtataacggc | ttctttagcg | atgccgatcg | cgcggcgatg | 1140 |
| aaaatcgttc | tggaaaccga | accgcgcaat | ctgccggcgc | tggatattac | ctttgttgat | 1200 |
| aaacgtattg | aaaaactgct | gtttaattat | cgtgcgcgca | tttttccggg | taccctggat | 1260 |
| tatgccgaac | agcagcgttg | gctggaacat | cgtcgtcagg | ttttcacccc | ggaatttctg | 1320 |
| cagggttatg | cggatgaact | gcagatgctg | gttcagcagt | atgccgatga | taaagaaaaa | 1380 |
| gtggcgctgc | tgaaagcgct | gtggcagtat | gcggaagaaa | tcgtttctgg | ctctggtcac | 1440 |
| catcatcatc | accac | | | | | 1455 |

<210> SEQ ID NO 26
<211> LENGTH: 485
<212> TYPE: PRT
<213> ORGANISM: Artificial sequence
<220> FEATURE:
<223> OTHER INFORMATION: EcoExo I C51A/C98T/C144T/C306T/C330T (ONLD0433)

<400> SEQUENCE: 26

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Thr Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 27
<211> LENGTH: 1455
<212> TYPE: DNA
<213> ORGANISM: Artificial sequence
<220> FEATURE:
<223> OTHER INFORMATION: EcoExo I C51A/C98T/C144M/C306S/C330T (ONLD0451)

<400> SEQUENCE: 27

```
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat gcgaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac caccattctg     300
ggctataaca atgtgcgctt cgatgatgaa gttacccgta atatcttta tcgtaacttt     360
tatgatccgt atgcgtggag ctggcagcat gataacagcc gttgggatct gctggatgtg     420
atgcgcgcga tgtatgcgct cgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc caccgtaaca acacaaact gatggcgctg     660
attgatgttc gcagatgaa accgctggtg catgtgagcg gcatgtttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga taccctgcgt     840
gaacgcctgt ataccgccaa aaccgatctg gcgataatg ccgccgtgcc ggtgaaactg     900
gttcacatta caaaagccc ggtgctggcc caggcgaaca ccctgcgccc ggaagatgcg     960
gatcgtctgg gtattaatcg ccagcatacc ctggataatc tgaaaatcct gcgtgaaaac    1020
ccgcaggtgc gtgaaaaagt ggtggcgatc ttcgcggaag cggaaccgtt caccccgagc    1080
gataacgtga tgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca tttttcgggg tacccctgat    1260
tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc tgaaagcgct gtggcagtat gcggaagaaa tcgtttctgg ctctggtcac    1440
catcatcatc accac                                                    1455
```

<210> SEQ ID NO 28
<211> LENGTH: 485
<212> TYPE: PRT

<213> ORGANISM: Artificial sequence
<220> FEATURE:
<223> OTHER INFORMATION: EcoExo I C51A/C98T/C144M/C306S/C330T (ONLD0451)

<400> SEQUENCE: 28

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Met
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
```

```
            385                 390                 395                 400
Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Lys Val Ala Leu Leu
        450                 455                 460

Lys Ala Leu Trp Gln Tyr Ala Glu Glu Ile Val Ser Gly Ser Gly His
465                 470                 475                 480

His His His His His
            485

<210> SEQ ID NO 29
<211> LENGTH: 1455
<212> TYPE: DNA
<213> ORGANISM: Artificial sequence
<220> FEATURE:
<223> OTHER INFORMATION: EcoExo I C51A/C98T/C144M/C306T/C330T (ONLD0452)

<400> SEQUENCE: 29
atgatgaacg atggcaaaca gcagagcacc ttcctgtttc atgattatga aaccttcggt        60
acccatccgg ccctggatcg tccggcgcag tttgcggcca ttcgcaccga tagcgaattc       120
aatgtgattg gcgaaccgga agtgttttat gcgaaaccgg ccgatgatta tctgccgcag       180
ccgggtgcgg tgctgattac cggtattacc ccgcaggaag cgcgcgcgaa aggtgaaaac       240
gaagcggcgt tgccgcgcg cattcatagc ctgtttaccg tgccgaaaac caccattctg       300
ggctataaca atgtgcgctt cgatgatgaa gttacccgta atatctttta tcgtaacttt       360
tatgatccgt atgcgtggag ctggcagcat gataacagcc gttgggatct gctggatgtg       420
atgcgcgcga tgtatgcgct cgcccccgaa ggcattaatt ggccggaaaa cgatgatggc       480
ctgccgagct ttcgtctgga acatctgacc aaagccaacg gcattgaaca tagcaatgcc       540
catgatgcga tggccgatgt ttatgcgacc attgcgatgg cgaaactggt taaaacccgt       600
cagccgcgcc tgtttgatta tctgtttacc caccgtaaca acacaaaact gatggcgctg       660
attgatgttc gcagatgaa accgctggtg catgtgagcg gcatgtttgg cgcctggcgc       720
ggcaacacca gctgggtggc cccgctggcc tggcacccgg aaaatcgtaa cgccgtgatt       780
atggttgatc tggccggtga tattagcccg ctgctggaac tggatagcga taccctgcgt       840
gaacgcctgt ataccgccaa accgatctg gcgataatg ccgccgtgcc ggtgaaactg       900
gttcacatta caaaaccccc ggtgctggcc caggcgaaca ccctgcgccc ggaagatgcg       960
gatcgtctgg gtattaatcg ccagcatacc ctggataatc tgaaaatcct gcgtgaaaac      1020
ccgcaggtgc gtgaaaaagt ggtggcgatc ttcgcggaag cggaaccgtt caccccgagc      1080
gataacgtgg atgcgcagct gtataacggc ttctttagcg atgccgatcg cgcggcgatg      1140
aaaatcgttc tggaaaccga accgcgcaat ctgccggcgc tggatattac ctttgttgat      1200
aaacgtattg aaaaactgct gtttaattat cgtgcgcgca ttttccggg taccctggat      1260 tatgccgaac agcagcgttg gctggaacat cgtcgtcagg ttttcacccc ggaatttctg      1320
cagggttatg cggatgaact gcagatgctg gttcagcagt atgccgatga taaagaaaaa      1380
gtggcgctgc tgaaagcgct gtggcagtat gcggaagaaa tcgtttctgg ctctggtcac      1440
catcatcatc accac                                                       1455
```

<210> SEQ ID NO 30
<211> LENGTH: 485
<212> TYPE: PRT
<213> ORGANISM: Artificial sequence
<220> FEATURE:
<223> OTHER INFORMATION: EcoExo I C51A/C98T/C144M/C306T/C330T (ONLD0452)

<400> SEQUENCE: 30

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Met
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Thr Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365
```

```
Asn Gly Phe Phe Ser Asp Ala Asp Arg Ala Ala Met Lys Ile Val Leu
            370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
                435                 440                 445

Met Leu Val Gln Gln Tyr Ala Asp Asp Lys Glu Lys Val Ala Leu Leu
            450                 455                 460

Lys Ala Leu Trp Gln Tyr Ala Glu Glu Ile Val Ser Gly Ser Gly His
465                 470                 475                 480

His His His His His
            485

<210> SEQ ID NO 31
<211> LENGTH: 1455
<212> TYPE: DNA
<213> ORGANISM: Artificial sequence
<220> FEATURE:
<223> OTHER INFORMATION: EcoExo I C51A/C98G/C144T/C306S/C330T (ONLD0453)

<400> SEQUENCE: 31
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccgga agtgttttat gcgaaaccgg ccgatgatta tctgccgcag     180
ccgggtgcgg tgctgattac cggtattacc cgcaggaag cgcgcgcgaa aggtgaaaac     240
gaagcggcgt tgccgcgcg cattcatagc ctgtttaccg tgccgaaaac cggcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcga cctatgcgct cgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaacccgt      600 cagccgcgcc tgtttgatta tctgtttacc caccgtaaca acacaaaact gatggcgctg     660
attgatgttc cgcagatgaa accgctggtg catgtgagcg catgttttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga tacccctgcgt     840 gaacgcctgt ataccgccaa aaccgatctg ggcgataatg ccgccgtgcc ggtgaaactg     900
gttcacatta caaaagccc ggtgctggcc caggcgaaca ccctgcgccc ggaagatgcg     960
gatcgtctgg gtattaatcg ccagcatacc ctggataatc tgaaaatcct gcgtgaaaac    1020
ccgcaggtgc gtgaaaaagt ggtggcgatc ttcgcggaag cggaaccgtt caccccgagc    1080
gataacgtga tgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca ttttccgggg taccctggat    1260
tatgccgaac agcagcgttg gctggaacat cgtcgtcagg ttttcacccc ggaatttctg    1320
```

```
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 32
<211> LENGTH: 485
<212> TYPE: PRT
<213> ORGANISM: Artificial sequence
<220> FEATURE:
<223> OTHER INFORMATION: EcoExo I C51A/C98G/C144T/C306S/C330T (ONLD0453)

<400> SEQUENCE: 32

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Gly Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335
```

```
Leu Arg Glu Asn Pro Gln Val Arg Glu Lys Val Val Ala Ile Phe Ala
              340                 345                 350
Glu Ala Glu Pro Phe Thr Pro Ser Asp Asn Val Asp Ala Gln Leu Tyr
          355                 360                 365
Asn Gly Phe Phe Ser Asp Ala Asp Arg Ala Ala Met Lys Ile Val Leu
      370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
              405                 410                 415
Gly Thr Leu Asp Tyr Ala Glu Gln Gln Arg Trp Leu Glu His Arg Arg
          420                 425                 430
Gln Val Phe Thr Pro Glu Phe Leu Gln Gly Tyr Ala Asp Glu Leu Gln
      435                 440                 445
Met Leu Val Gln Gln Tyr Ala Asp Asp Lys Glu Lys Val Ala Leu Leu
  450                 455                 460
Lys Ala Leu Trp Gln Tyr Ala Glu Glu Ile Val Ser Gly Ser Gly His
465                 470                 475                 480
His His His His His
              485
```

<210> SEQ ID NO 33
<211> LENGTH: 1455
<212> TYPE: DNA
<213> ORGANISM: Artificial sequence
<220> FEATURE:
<223> OTHER INFORMATION: EcoExo I C51A/C98T/C144T/C306S/C330T (ONLD0491)

<400> SEQUENCE: 33

```
atgatgaacg atggcaaaca gcagagcacc ttcctgtttc atgattatga aaccttcggt    60
acccatccgg ccctggatcg tccggcgcag tttgcggcca ttcgcaccga tagcgaattc   120
aatgtgattg cgaaccgga agtgttttat gcgaaaccgg ccgatgatta tctgccgcag   180
ccgggtgcgg tgctgattac cggtattacc cgcaggaag cgcgcgcgaa aggtgaaaac   240
gaagcggcgt ttgccgcgcg cattcatagc ctgtttaccg tgccgaaaac cgatattctg   300
ggctataaca atgtgcgctt cgatgatgaa gttacccgta atatctttta tcgtaacttt   360
tatgatccgt atgcgtggag ctggcagcat gataacagcc gttgggatct gctggatgtg   420
atgcgcgcga cctatgcgct cgcccggaa ggcattaatt ggccggaaaa cgatgatggc   480
ctgccgagct ttcgtctgga acatctgacc aaagccaacg gcattgaaca tagcaatgcc   540
catgatgcga tggccgatgt ttatgcgacc attgcgatgg cgaaactggt taaaacccgt   600
cagccgcgcc tgtttgatta tctgtttacc caccgtaaca acacaaaact gatggcgctg   660
attgatgttc cgcagatgaa accgctggtg catgtgagcg catgtttgg cgcctggcgc   720
ggcaacacca gctgggtggc cccgctggcc tggcacccgg aaaatcgtaa cgccgtgatt   780
atggttgatc tggccggtga tattagcccg ctgctggaac tggatagcga taccctgcgt   840
gaacgcctgt ataccgccaa aaccgatctg ggcgataatg ccgccgtgcc ggtgaaactg   900
gttcacatta caaaagccc ggtgctggcc caggcgaaca ccctgcgccc ggaagatgcg   960
gatcgtctgg gtattaatcg ccagcatacc ctggataatc tgaaaatcct gcgtgaaaac  1020
ccgcaggtgc gtgaaaaagt ggtggcgatc ttcgcggaag cggaaccgtt cacccccgagc  1080
gataacgtga tgcgcagct gtataacggc ttctttagcg atgccgatcg cgcggcgatg  1140
aaaatcgttc tggaaaccga accgcgcaat ctgccggcgc tggatattac ctttgttgat  1200
```

-continued

```
aaacgtattg aaaaactgct gtttaattat cgtgcgcgca atttccgggg taccctggat   1260
tatgccgaac agcagcgttg gctggaacat cgtcgtcagg ttttcaccc  ggaatttctg   1320 cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 34
<211> LENGTH: 485
<212> TYPE: PRT
<213> ORGANISM: Artificial sequence
<220> FEATURE:
<223> OTHER INFORMATION: EcoExo I C51A/C98T/C144T/C306S/C330T (ONLD0491)

<400> SEQUENCE: 34

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Asp Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Ser Pro Val Leu Ala Gln Ala Asn Thr Leu Arg Pro Glu Asp Ala
```

```
                305                 310                 315                 320
Asp Arg Leu Gly Ile Asn Arg Gln His Thr Leu Asp Asn Leu Lys Ile
                325                 330                 335
Leu Arg Glu Asn Pro Gln Val Arg Glu Lys Val Val Ala Ile Phe Ala
                340                 345                 350
Glu Ala Glu Pro Phe Thr Pro Ser Asp Asn Val Asp Ala Gln Leu Tyr
                355                 360                 365
Asn Gly Phe Phe Ser Asp Ala Asp Arg Ala Ala Met Lys Ile Val Leu
                370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
                420                 425                 430
Gln Val Phe Thr Pro Glu Phe Leu Gln Gly Tyr Ala Asp Glu Leu Gln
                435                 440                 445
Met Leu Val Gln Gln Tyr Ala Asp Asp Lys Glu Lys Val Ala Leu Leu
                450                 455                 460
Lys Ala Leu Trp Gln Tyr Ala Glu Glu Ile Val Ser Gly Ser Gly His
465                 470                 475                 480
His His His His His
                485

<210> SEQ ID NO 35
<211> LENGTH: 1455
<212> TYPE: DNA
<213> ORGANISM: Artificial sequence
<220> FEATURE:
<223> OTHER INFORMATION: EcoExo I C51A/C98K/C144T/C306S/C330T (ONLD0454)

<400> SEQUENCE: 35
atgatgaacg atggcaaaca gcagagcacc ttcctgtttc atgattatga aaccttcggt        60
acccatccgg ccctggatcg tccggcgcag tttgcggcca ttcgcaccga tagcgaattc       120
aatgtgattg gcgaaccgga agtgttttat gcgaaaccgg ccgatgatta tctgccgcag       180
ccgggtgcgg tgctgattac cggtattacc cgcaggaag cgcgcgcgaa aggtgaaaac        240
gaagcggcgt ttgccgcgcg cattcatagc ctgtttaccg tgccgaaaac caaaattctg       300
ggctataaca tgtgcgctt cgatgatgaa gttacccgta atatcttta tcgtaacttt        360 tatgatccgt atgcgtggag ctggcagcat gataacagcc gttgggatct gctggatgtg       420
atgcgcgcga cctatgcgct gcgcccggaa ggcattaatt ggccggaaaa cgatgatggc       480
ctgccgagct ttcgtctgga acatctgacc aaagccaacg gcattgaaca tagcaatgcc       540
catgatgcga tggccgatgt ttatgcgacc attgcgatgg cgaaactggt taaaacccgt       600
cagccgcgcc tgtttgatta tctgtttacc accgtaaca acacaaaact gatggcgctg       660
attgatgttc gcagatgaa accgctggtg catgtgagcg gcatgtttgg cgcctggcgc       720
ggcaacacca gctgggtggc cccgctggcc tggcacccgg aaaatcgtaa cgccgtgatt       780
atggttgatc tggccggtga tattagcccg ctgctggaac tggatagcga tacccctgcgt       840 gaacgcctgt ataccgccaa aaccgatctg ggcgataatg ccgccgtgcc ggtgaaactg       900
gttcacatta caaaagcccc ggtgctggcc caggcgaaca ccctgcgccc ggaagatgcg       960
gatcgtctgg gtattaatcg ccagcatacc ctggataatc tgaaaatcct gcgtgaaaac      1020
```

-continued

```
ccgcaggtgc gtgaaaaagt ggtggcgatc ttcgcggaag cggaaccgtt cacccccgagc   1080 gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 36
<211> LENGTH: 485
<212> TYPE: PRT
<213> ORGANISM: Artificial sequence
<220> FEATURE:
<223> OTHER INFORMATION: EcoExo I C51A/C98K/C144T/C306S/C330T (ONLD0454)

<400> SEQUENCE: 36

```
Met Met Asn Asp Gly Lys Gln Gln Ser Thr Phe Leu Phe His Asp Tyr
1               5                   10                  15
Glu Thr Phe Gly Thr His Pro Ala Leu Asp Arg Pro Ala Gln Phe Ala
            20                  25                  30
Ala Ile Arg Thr Asp Ser Glu Phe Asn Val Ile Gly Glu Pro Glu Val
        35                  40                  45
Phe Tyr Ala Lys Pro Ala Asp Asp Tyr Leu Pro Gln Pro Gly Ala Val
    50                  55                  60
Leu Ile Thr Gly Ile Thr Pro Gln Glu Ala Arg Ala Lys Gly Glu Asn
65                  70                  75                  80
Glu Ala Ala Phe Ala Ala Arg Ile His Ser Leu Phe Thr Val Pro Lys
                85                  90                  95
Thr Lys Ile Leu Gly Tyr Asn Asn Val Arg Phe Asp Asp Glu Val Thr
            100                 105                 110
Arg Asn Ile Phe Tyr Arg Asn Phe Tyr Asp Pro Tyr Ala Trp Ser Trp
        115                 120                 125
Gln His Asp Asn Ser Arg Trp Asp Leu Leu Asp Val Met Arg Ala Thr
    130                 135                 140
Tyr Ala Leu Arg Pro Glu Gly Ile Asn Trp Pro Glu Asn Asp Asp Gly
145                 150                 155                 160
Leu Pro Ser Phe Arg Leu Glu His Leu Thr Lys Ala Asn Gly Ile Glu
                165                 170                 175
His Ser Asn Ala His Asp Ala Met Ala Asp Val Tyr Ala Thr Ile Ala
            180                 185                 190
Met Ala Lys Leu Val Lys Thr Arg Gln Pro Arg Leu Phe Asp Tyr Leu
        195                 200                 205
Phe Thr His Arg Asn Lys His Lys Leu Met Ala Leu Ile Asp Val Pro
    210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
```

```
Asp Leu Gly Asp Asn Ala Ala Val Pro Val Lys Leu Val His Ile Asn
        290                 295                 300
Lys Ser Pro Val Leu Ala Gln Ala Asn Thr Leu Arg Pro Glu Asp Ala
305                 310                 315                 320
Asp Arg Leu Gly Ile Asn Arg Gln His Thr Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
        435                 440                 445
Met Leu Val Gln Gln Tyr Ala Asp Asp Lys Glu Lys Val Ala Leu Leu
450                 455                 460
Lys Ala Leu Trp Gln Tyr Ala Glu Glu Ile Val Ser Gly Ser Gly His
465                 470                 475                 480
His His His His
            485

<210> SEQ ID NO 37
<211> LENGTH: 1455
<212> TYPE: DNA
<213> ORGANISM: Artificial sequence
<220> FEATURE:
<223> OTHER INFORMATION: EcoExo I C51A/C98L/C144T/C306S/C330T (ONLD0455)

<400> SEQUENCE: 37
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccggaa gtgttttat gcgaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac cctgattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcga cctatgcgct cgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc accgtaaca aacacaaact gatgcgctg      660
attgatgttc gcagatgaa accgctggtg catgtgagcg gcatgtttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga taccctgcgt     840
gaacgcctgt ataccgccaa aaccgatctg ggcgataatg ccgccgtgcc ggtgaaactg     900
```

-continued

```
gttcacatta acaaaagccc ggtgctggcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt caccccgagc   1080
gataacgtga tgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 38
<211> LENGTH: 485
<212> TYPE: PRT
<213> ORGANISM: Artificial sequence
<220> FEATURE:
<223> OTHER INFORMATION: EcoExo I C51A/C98L/C144T/C306S/C330T (ONLD0455)

<400> SEQUENCE: 38

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Leu Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255
```

```
Asn Ala Val Ile Met Val Asp Leu Ala Gly Asp Ile Ser Pro Leu Leu
                260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
        290                 295                 300

Lys Ser Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His
            485

<210> SEQ ID NO 39
<211> LENGTH: 1455
<212> TYPE: DNA
<213> ORGANISM: Artificial sequence
<220> FEATURE:
<223> OTHER INFORMATION: EcoExo I C51A/C98V/C144T/C306S/C330T (ONLD0456)

<400> SEQUENCE: 39
atgatgaacg atggcaaaca gcagagcacc ttcctgtttc atgattatga aaccttcggt     60
acccatccgg ccctggatcg tccggcgcag tttgcggcca ttcgcaccga tagcgaattc    120
aatgtgattg cgaaccgga agtgttttat gcgaaaccgg ccgatgatta tctgccgcag    180
ccgggtgcgt tgctgattac cggtattacc ccgcaggaag cgcgcgcgaa aggtgaaaac    240
gaagcggcgt tgccgcgcg cattcatagc ctgtttaccg tgccgaaaac cgtgattctg    300
ggctataaca atgtgcgctt cgatgatgaa gttacccgta atatctttta tcgtaacttt    360
tatgatccgt atgcgtggag ctggcagcat gataacagcc gttgggatct gctggatgtg    420
atgcgcgcga cctatgcgct gcgcccggaa ggcattaatt ggccggaaaa cgatgatggc    480
ctgccgagct ttcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca acacaaaact gatggcgctg    660
attgatgttc gcagatgaa accgctggtg catgtgagcg gcatgtttgg cgcctggcgc    720
```

```
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta acaaaagccc ggtgctggcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg tacccctggat  1260 tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 40
<211> LENGTH: 485
<212> TYPE: PRT
<213> ORGANISM: Artificial sequence
<220> FEATURE:
<223> OTHER INFORMATION: EcoExo I C51A/C98V/C144T/C306S/C330T (ONLD0456)

<400> SEQUENCE: 40

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Val Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
```

```
                225                 230                 235                 240
            Gly Asn Thr Ser Trp Val Ala Pro Leu Ala Trp His Pro Glu Asn Arg
                            245                 250                 255

Asn Ala Val Ile Met Val Asp Leu Ala Gly Asp Ile Ser Pro Leu Leu
                        260                 265                 270

Glu Leu Asp Ser Asp Thr Leu Arg Glu Arg Leu Tyr Thr Ala Lys Thr
                    275                 280                 285

Asp Leu Gly Asp Asn Ala Ala Val Pro Val Lys Leu Val His Ile Asn
                290                 295                 300

Lys Ser Pro Val Leu Ala Gln Ala Asn Thr Leu Arg Pro Glu Asp Ala
            305                 310                 315                 320

Asp Arg Leu Gly Ile Asn Arg Gln His Thr Leu Asp Asn Leu Lys Ile
                            325                 330                 335

Leu Arg Glu Asn Pro Gln Val Arg Glu Lys Val Val Ala Ile Phe Ala
                        340                 345                 350

Glu Ala Glu Pro Phe Thr Pro Ser Asp Asn Val Asp Ala Gln Leu Tyr
                    355                 360                 365

Asn Gly Phe Phe Ser Asp Ala Asp Arg Ala Ala Met Lys Ile Val Leu
                370                 375                 380

Glu Thr Glu Pro Arg Asn Leu Pro Ala Leu Asp Ile Thr Phe Val Asp
            385                 390                 395                 400

Lys Arg Ile Glu Lys Leu Leu Phe Asn Tyr Arg Ala Arg Asn Phe Pro
                            405                 410                 415

Gly Thr Leu Asp Tyr Ala Glu Gln Gln Arg Trp Leu Glu His Arg Arg
                        420                 425                 430

Gln Val Phe Thr Pro Glu Phe Leu Gln Gly Tyr Ala Asp Glu Leu Gln
                    435                 440                 445

Met Leu Val Gln Gln Tyr Ala Asp Asp Lys Glu Lys Val Ala Leu Leu
                450                 455                 460

Lys Ala Leu Trp Gln Tyr Ala Glu Glu Ile Val Ser Gly Ser Gly His
            465                 470                 475                 480

His His His His His
                        485

<210> SEQ ID NO 41
<211> LENGTH: 1455
<212> TYPE: DNA
<213> ORGANISM: Artificial sequence
<220> FEATURE:
<223> OTHER INFORMATION: EcoExo I C51A/C98V/C144T/C306T/C330T (ONLD0476)

<400> SEQUENCE: 41
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat gcgaaaccgg ccgatgatta tctgccgcag     180
ccgggtgcgg tgctgattac cggtattacc ccgcaggaag cgcgcgcgaa aggtgaaaac     240
gaagcggcgt tgccgcgcgc cattcatagc ctgtttaccg tgccgaaaac cgtgattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcga cctatgcgct gcgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
```

```
cagccgcgcc tgtttgatta tctgtttacc caccgtaaca aacacaaact gatggcgctg    660
attgatgttc cgcagatgaa accgctggtg catgtgagcg catgtttgg  cgcctggcgc    720 ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta caaaacccc  ggtgctggcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                   1455

<210> SEQ ID NO 42
<211> LENGTH: 485
<212> TYPE: PRT
<213> ORGANISM: Artificial sequence
<220> FEATURE:
<223> OTHER INFORMATION: EcoExo I C51A/C98V/C144T/C306T/C330T (ONLD0476)

<400> SEQUENCE: 42

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
                20                  25                  30

Ala Ile Arg Thr Asp Ser Glu Phe Asn Val Ile Gly Glu Pro Glu Val
            35                  40                  45

Phe Tyr Ala Lys Pro Ala Asp Asp Tyr Leu Pro Gln Pro Gly Ala Val
        50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Val Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205
```

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
                260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
        290                 295                 300

Lys Thr Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 43
<211> LENGTH: 1455
<212> TYPE: DNA
<213> ORGANISM: Artificial sequence
<220> FEATURE:
<223> OTHER INFORMATION: EcoExo I C51A/C98T/C144T/C306M/C330T (ONLD0477)

<400> SEQUENCE: 43
atgatgaacg atggcaaaca gcagagcacc ttcctgtttc atgattatga aaccttcggt    60
acccatccgg ccctggatcg tccggcgcag tttgcggcca ttcgcaccga tagcgaattc   120
aatgtgattg gcgaaccgga agtgttttat gcgaaaccgg ccgatgatta tctgccgcag   180
ccgggtgcgt gctgattac cggtattacc ccgcaggaag cgcgcgcgaa aggtgaaaac   240
gaagcggcgt tgccgcgcg cattcatagc ctgtttaccg tgccgaaaac caccattctg   300
ggctataaca atgtgcgctt cgatgatgaa gttacccgta atatcttta cgtaactttt   360 tatgatccgt atgcgtggag ctggcagcat gataacagcc gttgggatct gctggatgtg   420

```
atgcgcgcga cctatgcgct gcgcccggaa ggcattaatt ggccggaaaa cgatgatggc    480
ctgccgagct ttcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca acacaaaact gatggcgctg    660
attgatgttc cgcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga tacccctgcgt    840
gaacgcctgt ataccgccaa aaccgatctg ggcgataatg ccgccgtgcc ggtgaaactg    900
gttcacatta acaaaatgcc ggtgctggcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt cacccccgagc  1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 44
<211> LENGTH: 485
<212> TYPE: PRT
<213> ORGANISM: Artificial sequence
<220> FEATURE:
<223> OTHER INFORMATION: EcoExo I C51A/C98T/C144T/C306M/C330T (ONLD0477)

<400> SEQUENCE: 44

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175
```

His Ser Asn Ala His Asp Ala Met Ala Asp Val Tyr Ala Thr Ile Ala
            180                 185                 190
Met Ala Lys Leu Val Lys Thr Arg Gln Pro Arg Leu Phe Asp Tyr Leu
        195                 200                 205
Phe Thr His Arg Asn Lys His Lys Leu Met Ala Leu Ile Asp Val Pro
    210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
Asp Leu Gly Asp Asn Ala Ala Val Pro Val Lys Leu Val His Ile Asn
    290                 295                 300
Lys Met Pro Val Leu Ala Gln Ala Asn Thr Leu Arg Pro Glu Asp Ala
305                 310                 315                 320
Asp Arg Leu Gly Ile Asn Arg Gln His Thr Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
    370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
        435                 440                 445
Met Leu Val Gln Gln Tyr Ala Asp Asp Lys Glu Lys Val Ala Leu Leu
    450                 455                 460
Lys Ala Leu Trp Gln Tyr Ala Glu Glu Ile Val Ser Gly Ser Gly His
465                 470                 475                 480
His His His His
            485

<210> SEQ ID NO 45
<211> LENGTH: 1455
<212> TYPE: DNA
<213> ORGANISM: Artificial sequence
<220> FEATURE:
<223> OTHER INFORMATION: EcoExo I C51A/C98T/C144T/C306N/C330T (ONLD0478)

<400> SEQUENCE: 45
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat gcgaaaccgg ccgatgatta tctgccgcag     180
ccgggtgcgc tgctgattac cggtattacc ccgcaggaag cgcgcgcgaa aggtgaaaac     240
gaagcggcgt tgccgcgcgc cattcatagc ctgtttaccg tgccgaaaac caccattctg     300

-continued

```
ggctataaca atgtgcgctt cgatgatgaa gttacccgta atatctttta tcgtaacttt    360
tatgatccgt atgcgtggag ctggcagcat gataacagcc gttgggatct gctggatgtg    420
atgcgcgcga cctatgcgct gcgcccggaa ggcattaatt ggccggaaaa cgatgatggc    480
ctgccgagct ttcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca aacacaaact gatggcgctg    660
attgatgttc gcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta acaaaaaccc ggtgctggcc caggcgaaca ccctgcgccc ggaagatgcg    960
gatcgtctgg gtattaatcg ccagcatacc ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc tgaaagcgct gtggcagtat gcggaagaaa tcgtttctgg ctctggtcac   1440
catcatcatc accac                                                    1455
```

<210> SEQ ID NO 46
<211> LENGTH: 485
<212> TYPE: PRT
<213> ORGANISM: Artificial sequence
<220> FEATURE:
<223> OTHER INFORMATION: EcoExo I C51A/C98T/C144T/C306N/C330T (ONLD0478)

<400> SEQUENCE: 46

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
```

```
                145                 150                 155                 160
Leu Pro Ser Phe Arg Leu Glu His Leu Thr Lys Ala Asn Gly Ile Glu
                    165                 170                 175

His Ser Asn Ala His Asp Ala Met Ala Asp Val Tyr Ala Thr Ile Ala
                180                 185                 190

Met Ala Lys Leu Val Lys Thr Arg Gln Pro Arg Leu Phe Asp Tyr Leu
            195                 200                 205

Phe Thr His Arg Asn Lys His Lys Leu Met Ala Leu Ile Asp Val Pro
        210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
                260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
        290                 295                 300

Lys Asn Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
                340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
        370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
                420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
        450                 455                 460

Lys Ala Leu Trp Gln Tyr Ala Glu Glu Ile Val Ser Gly Ser Gly His
465                 470                 475                 480

His His His His
            485

<210> SEQ ID NO 47
<211> LENGTH: 1455
<212> TYPE: DNA
<213> ORGANISM: Artificial sequence
<220> FEATURE:
<223> OTHER INFORMATION: EcoExo I C51A/C98T/C144T/C306D/C330T (ONLD0479)

<400> SEQUENCE: 47
atgatgaacg atggcaaaca gcagagcacc ttcctgtttc atgattatga aaccttcggt        60
acccatccgg ccctggatcg tccggcgcag tttgcggcca ttcgcaccga tagcgaattc       120
```

```
aatgtgattg gcgaaccgga agtgttttat gcgaaaccgg ccgatgatta tctgccgcag      180
ccgggtgcgg tgctgattac cggtattacc ccgcaggaag cgcgcgcgaa aggtgaaaac      240
gaagcggcgt ttgccgcgcg cattcatagc ctgtttaccg tgccgaaaac caccattctg      300
ggctataaca atgtgcgctt cgatgatgaa gttacccgta atatctttta tcgtaacttt      360
tatgatccgt atgcgtggag ctggcagcat gataacagcc gttgggatct gctggatgtg      420
atgcgcgcga cctatgcgct cgcccggaa ggcattaatt ggccgaaaaa cgatgatggc      480
ctgccgagct ttcgtctgga acatctgacc aaagccaacg gcattgaaca tagcaatgcc      540
catgatgcga tggccgatgt ttatgcgacc attgcgatgg cgaaactggt taaaacccgt      600
cagccgcgcc tgtttgatta tctgtttacc caccgtaaca aacacaaact gatggcgctg      660
attgatgttc cgcagatgaa accgctggtg catgtgagcg gcatgtttgg cgcctggcgc      720
ggcaacacca gctgggtggc cccgctggcc tggcacccgg aaaatcgtaa cgccgtgatt      780
atggttgatc tggccggtga tattagcccg ctgctggaac tggatagcga tacctgcgt       840
gaacgcctgt ataccgccaa aaccgatctg gcgataatg ccgccgtgcc ggtgaaactg       900
gttcacatta acaaagatcc ggtgctggcc caggcgaaca ccctgcgccc ggaagatgcg      960
gatcgtctgg gtattaatcg ccagcatacc ctggataatc tgaaaatcct gcgtgaaaac      1020
ccgcaggtgc gtgaaaaagt ggtggcgatc ttcgcggaag cggaaccgtt caccccgagc      1080
gataacgtga tgcgcagct gtataacggc ttctttagcg atgccgatcg cgcggcgatg       1140
aaaatcgttc tggaaaccga accgcgcaat ctgccggcgc tggatattac ctttgttgat      1200
aaacgtattg aaaaactgct gtttaattat cgtgcgcgca attttccggg tacctggat       1260
tatgccgaac agcagcgttg gctggaacat cgtcgtcagg ttttcacccc ggaattctg       1320
cagggttatg cggatgaact gcagatgctg gttcagcagt atgccgatga taagaaaaa       1380
gtggcgctgc tgaaagcgct gtggcagtat gcggaagaaa tcgtttctgg ctctggtcac      1440
catcatcatc accac                                                      1455
```

<210> SEQ ID NO 48
<211> LENGTH: 485
<212> TYPE: PRT
<213> ORGANISM: Artificial sequence
<220> FEATURE:
<223> OTHER INFORMATION: EcoExo I C51A/C98T/C144T/C306D/C330T (ONLD0479)

<400> SEQUENCE: 48

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
                20                  25                  30

Ala Ile Arg Thr Asp Ser Glu Phe Asn Val Ile Gly Glu Pro Glu Val
            35                  40                  45

Phe Tyr Ala Lys Pro Ala Asp Asp Tyr Leu Pro Gln Pro Gly Ala Val
        50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125
```

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Asp Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 49
<211> LENGTH: 1455
<212> TYPE: DNA
<213> ORGANISM: Artificial sequence
<220> FEATURE:
<223> OTHER INFORMATION: EcoExo I C51A/C98T/C144T/C306A/C330T (ONLD0480)

<400> SEQUENCE: 49

```
atgatgaacg atggcaaaca gcagagcacc ttcctgtttc atgattatga aaccttcggt    60
acccatccgg ccctggatcg tccggcgcag tttgcggcca ttcgcaccga tagcgaattc   120
aatgtgattg gcgaaccgga agtgttttat gcgaaaccgg ccgatgatta tctgccgcag   180
ccgggtgcgg tgctgattac cggtattacc ccgcaggaag cgcgcgcgaa aggtgaaaac   240
gaagcggcgt ttgccgcgcg cattcatagc ctgtttaccg tgccgaaaac caccattctg   300
ggctataaca atgtgcgctt cgatgatgaa gttacccgta atatctttta tcgtaacttt   360
tatgatccgt atgcgtggag ctggcagcat gataacagcc gttgggatct gctggatgtg   420
atgcgcgcga cctatgcgct cgcccggaa ggcattaatt ggccggaaaa cgatgatggc   480
ctgccgagct ttcgtctgga acatctgacc aaagccaacg gcattgaaca tagcaatgcc   540
catgatgcga tggccgatgt ttatgcgacc attgcgatgg cgaaactggt taaaacccgt   600
cagccgcgcc tgtttgatta tctgtttacc caccgtaaca acacaaaact gatggcgctg   660
attgatgttc cgcagatgaa accgctggtg catgtgagcg gcatgtttgg cgcctggcgc   720
ggcaacacca gctgggtggc cccgctggcc tggcacccgg aaaatcgtaa cgccgtgatt   780
atggttgatc tggccggtga tattagcccg ctgctggaac tggatagcga tccctgcgt   840
gaacgcctgt ataccgccaa aaccgatctg ggcgataatg ccgccgtgcc ggtgaaactg   900
gttcacatta caaagcgcc ggtgctggcc caggcgaaca ccctgcgccc ggaagatgcg   960
gatcgtctgg gtattaatcg ccagcatacc ctggataatc tgaaaatcct gcgtgaaaac  1020
ccgcaggtgc gtgaaaaagt ggtggcgatc ttcgcggaag cggaaccgtt caccccgagc  1080
gataacgtgg atgcgcagct gtataacggc ttctttagcg atgccgatcg cgcggcgatg  1140
aaaatcgttc tggaaaccga accgcgcaat ctgccggcgc tggatattac ctttgttgat  1200
aaacgtattg aaaaactgct gtttaattat cgtgcgcgca tttttccggg taccctggat  1260
tatgccgaac agcagcgttg gctggaacat cgtcgtcagg ttttcacccc ggaatttctg  1320
cagggttatg cggatgaact gcagatgctg gttcagcagt atgccgatga taaagaaaaa  1380
gtggcgctgc tgaaagcgct gtggcagtat gcggaagaaa tcgtttctgg ctctggtcac  1440
catcatcatc accac                                                   1455
```

<210> SEQ ID NO 50
<211> LENGTH: 485
<212> TYPE: PRT
<213> ORGANISM: Artificial sequence
<220> FEATURE:
<223> OTHER INFORMATION: EcoExo I C51A/C98T/C144T/C306A/C330T (ONLD0480)

<400> SEQUENCE: 50

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95
```

Thr Thr Ile Leu Gly Tyr Asn Asn Val Arg Phe Asp Asp Glu Val Thr
            100                 105                 110
Arg Asn Ile Phe Tyr Arg Asn Phe Tyr Asp Pro Tyr Ala Trp Ser Trp
            115                 120                 125
Gln His Asp Asn Ser Arg Trp Asp Leu Leu Asp Val Met Arg Ala Thr
        130                 135                 140
Tyr Ala Leu Arg Pro Glu Gly Ile Asn Trp Pro Glu Asn Asp Asp Gly
145                 150                 155                 160
Leu Pro Ser Phe Arg Leu Glu His Leu Thr Lys Ala Asn Gly Ile Glu
                165                 170                 175
His Ser Asn Ala His Asp Ala Met Ala Asp Val Tyr Ala Thr Ile Ala
            180                 185                 190
Met Ala Lys Leu Val Lys Thr Arg Gln Pro Arg Leu Phe Asp Tyr Leu
        195                 200                 205
Phe Thr His Arg Asn Lys His Lys Leu Met Ala Leu Ile Asp Val Pro
210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
Asp Leu Gly Asp Asn Ala Ala Val Pro Val Lys Leu Val His Ile Asn
290                 295                 300
Lys Ala Pro Val Leu Ala Gln Ala Asn Thr Leu Arg Pro Glu Asp Ala
305                 310                 315                 320
Asp Arg Leu Gly Ile Asn Arg Gln His Thr Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
        435                 440                 445
Met Leu Val Gln Gln Tyr Ala Asp Asp Lys Glu Lys Val Ala Leu Leu
450                 455                 460
Lys Ala Leu Trp Gln Tyr Ala Glu Glu Ile Val Ser Gly Ser Gly His
465                 470                 475                 480
His His His His His
            485

<210> SEQ ID NO 51
<211> LENGTH: 804
<212> TYPE: DNA

<213> ORGANISM: Escherichia. coli

<400> SEQUENCE: 51

```
atgaaatttg tctcttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
ggccattatg gcgtggcgct gctgaccaaa gagacgccga ttgccgtgcg tcgcggcttt     240
cccggtgacg acgaagaggc gcagcggcgg attattatgg cggaaatccc ctcactgctg     300
ggtaatgtca ccgtgatcaa cggttacttc ccgcagggtg aaagccgcga ccatccgata     360
aaattcccgg caaaagcgca gttttatcag aatctgcaaa actacctgga aaccgaactc     420
aaacgtgata tccggtact gattatgggc gatatgaata tcagccctac agatctggat     480
atcggcattg gcgaagaaaa ccgtaagcgc tggctgcgta ccggtaaatg ctctttcctg     540
ccggaagagc gcgaatggat ggacaggctg atgagctggg ggttggtcga taccttccgc     600
catgcgaatc cgcaaacagc agatcgtttc tcatggtttg attaccgctc aaaaggtttt     660
gacgataacc gtggtctgcg catcgacctg ctgctcgcca gccaaccgct ggcagaatgt     720
tgcgtagaaa ccggcatcga ctatgaaatc cgcagcatgg aaaaaccgtc cgatcacgcc     780
cccgtctggg cgaccttccg ccgc                                            804
```

<210> SEQ ID NO 52
<211> LENGTH: 268
<212> TYPE: PRT
<213> ORGANISM: Escherichia. coli

<400> SEQUENCE: 52

```
Met Lys Phe Val Ser Phe Asn Ile Asn Gly Leu Arg Ala Arg Pro His
  1               5                  10                  15

Gln Leu Glu Ala Ile Val Glu Lys His Gln Pro Asp Val Ile Gly Leu
             20                  25                  30

Gln Glu Thr Lys Val His Asp Asp Met Phe Pro Leu Glu Glu Val Ala
         35                  40                  45

Lys Leu Gly Tyr Asn Val Phe Tyr His Gly Gln Lys Gly His Tyr Gly
     50                  55                  60

Val Ala Leu Leu Thr Lys Glu Thr Pro Ile Ala Val Arg Arg Gly Phe
 65                  70                  75                  80

Pro Gly Asp Asp Glu Glu Ala Gln Arg Arg Ile Ile Met Ala Glu Ile
                 85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205
```

```
Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

```
<210> SEQ ID NO 53
<211> LENGTH: 1275
<212> TYPE: DNA
<213> ORGANISM: Thermus. thermophilus

<400> SEQUENCE: 53
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg cgtggaagt cattgttacc      360 gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg gaatacgcgg acctggcagc cgttggcacc     540
attgccgacg ttgccccgct gtggggttgg aatcgtgcac tggtgaaaga aggtctggca     600
cgcatcccgc cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct gcgcctgctg ctgacggatg atgcggcaga agctcaggcg     780
ctggtcggcg aactgcaccg tctgaacgcc cgtcgtcaga ccctggaaga agcgatgctg     840
cgcaaactgc tgccgcaggc cgacccggaa gcgaaagcca tcgttctgct ggacccggaa     900
ggccatccgg tgttatgggt atttgtggcc tctcgcatcc tggaagcgac cctgcgcccg     960
gtctttctgg tggcccaggg caaaggcacc gtgcgttcgc tggctccgat tccgccgtc    1020 gaagcactgc gcagcgcgga agatctgctg ctgcgttatg gtggtcataa agaagcggcg    1080
ggtttcgcaa tggatgaagc gctgtttccg gcgttcaaag cacgcgttga agcgtatgcc    1140
gcacgtttcc cggatccggt tcgtgaagtg gcactgctgg atctgctgcc ggaaccgggc    1200
ctgctgccgc aggtgttccg tgaactggca ctgctggaac cgtatggtga aggtaacccg    1260
gaaccgctgt tcctg                                                    1275
```

```
<210> SEQ ID NO 54
<211> LENGTH: 425
<212> TYPE: PRT
<213> ORGANISM: Thermus. thermophilus

<400> SEQUENCE: 54

Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
```

```
                35                  40                  45
Thr Gly Thr Ala Ile Leu Val Arg Gly Leu Ala Ala Leu Gly Ala Asp
 50                  55                  60

Val His Pro Phe Ile Pro His Arg Leu Glu Glu Gly Tyr Gly Val Leu
 65                  70                  75                  80

Met Glu Arg Val Pro Glu His Leu Glu Ala Ser Asp Leu Phe Leu Thr
                 85                  90                  95

Val Asp Cys Gly Ile Thr Asn His Ala Glu Leu Arg Glu Leu Leu Glu
                100                 105                 110

Asn Gly Val Glu Val Ile Val Thr Asp His His Thr Pro Gly Lys Thr
            115                 120                 125

Pro Pro Pro Gly Leu Val Val His Pro Ala Leu Thr Pro Asp Leu Lys
130                 135                 140

Glu Lys Pro Thr Gly Ala Gly Val Ala Phe Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
                180                 185                 190

Ala Leu Val Lys Glu Gly Leu Ala Arg Ile Pro Ala Ser Ser Trp Val
            195                 200                 205

Gly Leu Arg Leu Leu Ala Glu Ala Val Gly Tyr Thr Gly Lys Ala Val
210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
                260                 265                 270

Gln Thr Leu Glu Glu Ala Met Leu Arg Lys Leu Leu Pro Gln Ala Asp
            275                 280                 285

Pro Glu Ala Lys Ala Ile Val Leu Leu Asp Pro Glu Gly His Pro Gly
290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
                340                 345                 350

Tyr Gly Gly His Lys Glu Ala Ala Gly Phe Ala Met Asp Glu Ala Leu
            355                 360                 365

Phe Pro Ala Phe Lys Ala Arg Val Glu Ala Tyr Ala Ala Arg Phe Pro
370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
                420                 425

<210> SEQ ID NO 55
<211> LENGTH: 738
<212> TYPE: DNA
<213> ORGANISM: Bacteriophage
```

<400> SEQUENCE: 55

```
tccggaagcg gctctggtag tggttctggc atgacaccgg acattatcct gcagcgtacc        60
gggatcgatg tgagagctgt cgaacagggg gatgatgcgt ggcacaaatt acggctcggc       120
gtcatcaccg cttcagaagt tcacaacgtg atagcaaaac cccgctccgg aaagaagtgg       180
cctgacatga aaatgtccta cttccacacc ctgcttgctg aggtttgcac cggtgtggct       240
ccggaagtta acgctaaagc actggcctgg ggaaaacagt acgagaacga cgccagaacc       300
ctgtttgaat tcacttccgg cgtgaatgtt actgaatccc cgatcatcta tcgcgacgaa       360
agtatgcgta ccgcctgctc tcccgatggt ttatgcagtg acggcaacgg ccttgaactg       420
aaatgcccgt ttacctcccg ggatttcatg aagttccggc tcggtggttt cgaggccata       480
aagtcagctt acatggccca ggtgcagtac agcatgtggg tgacgcgaaa aaatgcctgg       540
tactttgcca actatgaccc gcgtatgaag cgtgaaggcc tgcattatgt cgtgattgag       600
cgggatgaaa agtacatggc gagttttgac gagatcgtgc cggagttcat cgaaaaaatg       660
gacgaggcac tggctgaaat tggttttgta tttggggagc aatggcgatc tggctctggt       720
tccggcagcg gttccgga                                                      738
```

<210> SEQ ID NO 56
<211> LENGTH: 226
<212> TYPE: PRT
<213> ORGANISM: Bacteriophage

<400> SEQUENCE: 56

```
Met Thr Pro Asp Ile Ile Leu Gln Arg Thr Gly Ile Asp Val Arg Ala
  1               5                  10                  15
Val Glu Gln Gly Asp Asp Ala Trp His Lys Leu Arg Leu Gly Val Ile
                 20                  25                  30
Thr Ala Ser Glu Val His Asn Val Ile Ala Lys Pro Arg Ser Gly Lys
             35                  40                  45
Lys Trp Pro Asp Met Lys Met Ser Tyr Phe His Thr Leu Leu Ala Glu
         50                  55                  60
Val Cys Thr Gly Val Ala Pro Glu Val Asn Ala Lys Ala Leu Ala Trp
 65                  70                  75                  80
Gly Lys Gln Tyr Glu Asn Asp Ala Arg Thr Leu Phe Glu Phe Thr Ser
                 85                  90                  95
Gly Val Asn Val Thr Glu Ser Pro Ile Ile Tyr Arg Asp Glu Ser Met
                100                 105                 110
Arg Thr Ala Cys Ser Pro Asp Gly Leu Cys Ser Asp Gly Asn Gly Leu
            115                 120                 125
Glu Leu Lys Cys Pro Phe Thr Ser Arg Asp Phe Met Lys Phe Arg Leu
        130                 135                 140
Gly Gly Phe Glu Ala Ile Lys Ser Ala Tyr Met Ala Gln Val Gln Tyr
145                 150                 155                 160
Ser Met Trp Val Thr Arg Lys Asn Ala Trp Tyr Phe Ala Asn Tyr Asp
                165                 170                 175
Pro Arg Met Lys Arg Glu Gly Leu His Tyr Val Val Ile Glu Arg Asp
            180                 185                 190
Glu Lys Tyr Met Ala Ser Phe Asp Glu Ile Val Pro Glu Phe Ile Glu
        195                 200                 205
Lys Met Asp Glu Ala Leu Ala Glu Ile Gly Phe Val Phe Gly Glu Gln
    210                 215                 220
```

Trp Arg
225

<210> SEQ ID NO 57
<211> LENGTH: 67
<212> TYPE: DNA
<213> ORGANISM: Artificial sequence
<220> FEATURE:
<223> OTHER INFORMATION: nucleic sequence from which preferred nucleic
      acid linkers can be generated

<400> SEQUENCE: 57
tgtgttctat gtcttattct tacttcgtta ttcttgtctc tattctgttt atgtttcttg    60
tttgtta                                                             67

<210> SEQ ID NO 58
<211> LENGTH: 17
<212> TYPE: DNA
<213> ORGANISM: Artificial sequence
<220> FEATURE:
<223> OTHER INFORMATION: nucleic acid linker

<400> SEQUENCE: 58
tgtgttctat gtctttt                                                  17

<210> SEQ ID NO 59
<211> LENGTH: 27
<212> TYPE: DNA
<213> ORGANISM: Artificial sequence
<220> FEATURE:
<223> OTHER INFORMATION: nucleic acid linker

<400> SEQUENCE: 59
tgtgttctat gtcttattct tactttt                                       27

<210> SEQ ID NO 60
<211> LENGTH: 37
<212> TYPE: DNA
<213> ORGANISM: Artificial sequence
<220> FEATURE:
<223> OTHER INFORMATION: nucleic acid linker

<400> SEQUENCE: 60
tgtgttctat gtcttattct tacttcgtta ttctttt                            37

<210> SEQ ID NO 61
<211> LENGTH: 17
<212> TYPE: DNA
<213> ORGANISM: Artificial sequence
<220> FEATURE:
<223> OTHER INFORMATION: nucleic acid linker

<400> SEQUENCE: 61
aagacataga acacatt                                                  17

<210> SEQ ID NO 62
<211> LENGTH: 27
<212> TYPE: DNA
<213> ORGANISM: Artificial sequence
<220> FEATURE:
<223> OTHER INFORMATION: nucleic acid linker

<400> SEQUENCE: 62
aagtaagaat aagacataga acacatt                                       27

```
<210> SEQ ID NO 63
<211> LENGTH: 37
<212> TYPE: DNA
<213> ORGANISM: Artificial sequence
<220> FEATURE:
<223> OTHER INFORMATION: nucleic acid linker

<400> SEQUENCE: 63
aagaataacg aagtaagaat aagacataga acacatt                              37

<210> SEQ ID NO 64
<211> LENGTH: 40
<212> TYPE: DNA
<213> ORGANISM: Artificial sequence
<220> FEATURE:
<223> OTHER INFORMATION: nucleic acid linker

<400> SEQUENCE: 64
aagaataacg aagtaagaat aagacataga acacatttt                            40

<210> SEQ ID NO 65
<211> LENGTH: 35
<212> TYPE: DNA
<213> ORGANISM: Artificial sequence
<220> FEATURE:
<223> OTHER INFORMATION: nucleic acid linker

<400> SEQUENCE: 65
tgtgttctat gtcttattct tacttcgtta ttctt                                35

<210> SEQ ID NO 66
<211> LENGTH: 15
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (12)..(12)
<223> OTHER INFORMATION: U base with azide groups

<400> SEQUENCE: 66
cctagtctcc gyagc                                                      15

<210> SEQ ID NO 67
<211> LENGTH: 15
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with azide groups
<220> FEATURE:
<221> NAME/KEY: modified_base
<222> LOCATION: (12)..(12)
<223> OTHER INFORMATION: U base with azide groups

<400> SEQUENCE: 67
ccyagtctcc gyagc                                                      15

<210> SEQ ID NO 68
<211> LENGTH: 15
<212> TYPE: DNA
<213> ORGANISM: Artificial sequence
<220> FEATURE:
<223> OTHER INFORMATION: nucleic acid linker
<220> FEATURE:
```

```
<221> NAME/KEY: modified_base
<222> LOCATION: (3)..(3)
<223> OTHER INFORMATION: U base with alkyne groups

<400> SEQUENCE: 68
gcyacggaga ctagg                                                    15

<210> SEQ ID NO 69
<211> LENGTH: 15
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with allyne groups
<220> FEATURE:
<221> NAME/KEY: modified_base
<222> LOCATION: (12)..(12)
<223> OTHER INFORMATION: U base with allyne groups

<400> SEQUENCE: 69
gcyacggaga cyagg                                                    15

<210> SEQ ID NO 70
<211> LENGTH: 6
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (2)..(2)
<223> OTHER INFORMATION: U base with azide groups
<220> FEATURE:
<221> NAME/KEY: modified_base
<222> LOCATION: (5)..(5)
<223> OTHER INFORMATION: U base with azide groups

<400> SEQUENCE: 70 cyaayg                                                               6

<210> SEQ ID NO 71
<211> LENGTH: 8
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (2)..(2)
<223> OTHER INFORMATION: U base with azide groups
<220> FEATURE:
<221> NAME/KEY: modified_base
<222> LOCATION: (5)..(5)
<223> OTHER INFORMATION: U base with azide groups

<400> SEQUENCE: 71 cyacyagc                                                             8

<210> SEQ ID NO 72
<211> LENGTH: 10
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with azide groups
```

```
<220> FEATURE:
<221> NAME/KEY: modified_base
<222> LOCATION: (7)..(7)
<223> OTHER INFORMATION: U base with azide groups

<400> SEQUENCE: 72 ccyagcyagc                                                               10

<210> SEQ ID NO 73
<211> LENGTH: 6
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with alkyne groups
<220> FEATURE:
<221> NAME/KEY: modified_base
<222> LOCATION: (4)..(4)
<223> OTHER INFORMATION: U base with alkyne groups

<400> SEQUENCE: 73 cayyag                                                                    6

<210> SEQ ID NO 74
<211> LENGTH: 8
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with alkyne groups
<220> FEATURE:
<221> NAME/KEY: modified_base
<222> LOCATION: (6)..(6)
<223> OTHER INFORMATION: U base with alkyne groups

<400> SEQUENCE: 74 gcyagyag                                                                  8

<210> SEQ ID NO 75
<211> LENGTH: 10
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with alkyne groups
<220> FEATURE:
<221> NAME/KEY: modified_base
<222> LOCATION: (7)..(7)
<223> OTHER INFORMATION: U base with alkyne groups

<400> SEQUENCE: 75 gcyagcyagg                                                               10

<210> SEQ ID NO 76
<211> LENGTH: 49
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (41)..(41)
```

```
<223> OTHER INFORMATION: U base with alkyne groups

<400> SEQUENCE: 76
ttgatcgtgt cgtatatccc gcctattttt ttttaagaca yagaacaca          49

<210> SEQ ID NO 77
<211> LENGTH: 15
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (10)..(10)
<223> OTHER INFORMATION: U base with azide groups

<400> SEQUENCE: 77
tgtgttctay gtctt                                                15

<210> SEQ ID NO 78
<211> LENGTH: 100
<212> TYPE: DNA
<213> ORGANISM: Artificial sequence
<220> FEATURE:
<223> OTHER INFORMATION: nucleic acid linker
<220> FEATURE:
<221> NAME/KEY: modified_base
<222> LOCATION: (3)..(3)
<223> OTHER INFORMATION: U base with alkyne groups
<220> FEATURE:
<221> NAME/KEY: modified_base
<222> LOCATION: (12)..(12)
<223> OTHER INFORMATION: U base with alkyne groups

<400> SEQUENCE: 78
gcyacggaga cyaggttttt tttttttttt tttttttttt tttttttttt          60
tttttttttt tttttttttt tttttttttt tttttttttt                    100
```

HYBRIDIZATION LINKERS

RELATED APPLICATIONS

This application is a 35 U.S.C. §371 national stage filing of PCT Application No. PCT/GB2010/000132 filed on Jan. 29, 2010, which claims priority to, and the benefit of, U.S. Provisional Patent Application No. 61/148,726 filed Jan. 30, 2009. The contents of the aforementioned applications are hereby incorporated by reference.

FIELD OF THE INVENTION

The invention relates to a method of covalently coupling two or more moieties. The invention involves the use of two or more linkers each comprising a hybridizable region and the use of two or more groups capable of forming a covalent bond. The hybridizable regions in the linkers hybridize and link the moieties. The linked moieties are then coupled via the formation of covalent bonds between the groups.

BACKGROUND OF THE INVENTION

The covalent coupling of two or more moieties has many applications within chemistry and biochemistry. When chemical coupling methods are employed, the reaction rate between moieties is dependent upon the concentrations of the moieties available to react. If the concentration of moieties is low, then the reaction rate may be rate limited by the moiety concentration. For many applications the concentration of moieties may be low, it is therefore desirable to produce methods that enhance the rate or reaction (or alternatively, methods that lower the concentration of moieties required).

It is well known that certain molecules, or collections of molecules, can be made to self assemble to form larger, more complex structures, examples of these include: DNA, proteins, lipids, liquid crystals, polymers etc. The molecular components of these species often have a very high affinity for each other and self assemble in low concentration. A drawback to self-assembling systems is that they often aggregate through non-covalent interactions and therefore have limited stability.

SUMMARY OF THE INVENTION

The inventors have surprisingly demonstrated that two or more moieties can be covalently coupled at low concentrations utilising the high affinity of self-assembling systems. More specifically, the inventors have surprisingly demonstrated that two or more high affinity hybridization linkers can be used to link two or more moieties before they are coupled using chemical groups that are capable of covalently reacting together. The resulting complex has a greater stability than the equivalent non-covalent complex formed using just the high affinity hybridization linkers.

The invention therefore provides a method of covalently coupling two or more moieties, the method comprising:
(a) providing a first moiety having covalently attached thereto (i) at least one first linker comprising a first hybridizable region and (ii) at least one first group capable of forming a covalent bond;
(b) providing a second moiety having covalently attached thereto (i) at least one second linker comprising a second hybridizable region capable of hybridizing to the first hybridizable region and (ii) at least one second group capable of forming a covalent bond with the first group;
(c) contacting the first and second moieties under conditions that allow the first and second hybridizable regions to hybridize and link the moieties; and
(d) exposing the linked moieties to conditions that allow the formation of a covalent bond between the first and second groups.

The invention also provides:
first and second moieties coupled using a method of the invention;
a first moiety coupled to a second moiety using first and second linkers of the invention;
a pair of first and second linkers of the invention; and
use of a pair of linkers of the invention to couple a first moiety to a second moiety.

DESCRIPTION OF THE SEQUENCE LISTING

Figure 1:
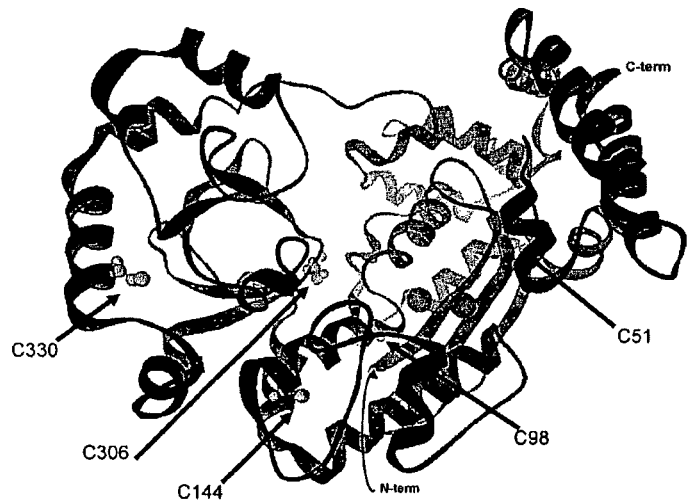
FIG. 1 shows a cartoon of the structure of EcoExo I showing the position and residue number of naturally occurring cysteines (obtained from crystal structure).

SEQ ID NO: 1 shows the polynucleotide sequence encoding one subunit of wild type α-hemolysin (α-HL).

SEQ ID NO: 2 shows the amino acid sequence of one subunit of wild type α-HL. Amino acids 2 to 6, 73 to 75, 207 to 209, 214 to 216 and 219 to 222 form α-helices. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 form β-strands. All the other non-terminal amino acids, namely 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 form loop regions. Amino acids 1 and 294 are terminal amino acids.

SEQ ID NO: 3 shows the polynucleotide sequence encoding one subunit of α-HL L135C/N139Q (HL-CQ).

SEQ ID NO: 4 shows the amino acid sequence of one subunit of α-HL L135C/N139Q (HL-CQ). The same amino acids that form α-helices, β-strands and loop regions in wild type α-HL form the corresponding regions in this subunit.

SEQ ID NO: 5 shows the codon optimised polynucleotide sequence derived from the sbcB gene from E. coli. It encodes the exonuclease I enzyme (EcoExo I) from E. coli.

SEQ ID NO: 6 shows the amino acid sequence of exonuclease I enzyme (EcoExo I) from E. coli. This enzyme performs processive digestion of 5' monophosphate nucleosides from single stranded DNA (ssDNA) in a 5' to 3' direction. Amino acids 60 to 68, 70 to 78, 80 to 93, 107 to 119, 124 to 128, 137 to 148, 165 to 172, 182 to 211, 213 to 221, 234 to 241, 268 to 286, 313 to 324, 326 to 352, 362 to 370, 373 to 391, 401 to 454 and 457 to 475 form α-helices Amino acids 10 to 18, 28 to 26, 47 to 50, 97 to 101, 133 to 136, 229 to 232, 243 to 251, 258 to 263, 298 to 302 and 308 to 311 form β-strands. All the other non-terminal amino acids, 19 to 27, 37 to 46, 51 to 59, 69, 79, 94 to 96 102 to 106, 120 to 123, 129 to 132, 149 to 164, 173 to 181, 212, 222 to 228 233, 242, 252 to 257, 264 to 267, 287 to 297, 303 to 307, 312, 325, 353 to 361, 371, 372, 392 to 400, 455 and 456, form loops. Amino acids 1 to 9 are terminal amino acids. The overall fold of the enzyme is such that three regions combine to form a molecule with the appearance of the letter C, although residues 355-358, disordered in the crystal structure, effectively convert this C into an O-like shape. The amino terminus (1-206) forms the exonuclease domain and has homology to the DnaQ superfamily, the following residues (202-354) form an SH3-like domain and the carboxyl domain (359-475) extends the exonuclease domain to form the C-like shape of the molecule. Four acidic residues of EcoExo I are conserved with the active site residues of the DnaQ superfamily (corresponding to D15, E17, D108 and D186). It is suggested a single metal ion is bound by residues D15 and 108. Hydrolysis of DNA is likely catalyzed by attack of the scissile phosphate with an activated water molecule, with H181 being the catalytic residue and aligning the nucleotide substrate.

SEQ ID NO: 7 shows the codon optimised polynucleotide sequence encoding EcoExo I C98S/C306S/C330T/C51A (ONLD0393).

SEQ ID NO: 8 shows the amino acid sequence of EcoExo I C98S/C306S/C330T/C51A (ONLD0393).

SEQ ID NO: 9 shows the codon optimised polynucleotide sequence encoding EcoExo I C98S/C306S/C330T/C144M (ONLD0403).

SEQ ID NO: 10 shows the amino acid sequence of EcoExo I C98S/C306S/C330T/C144M (ONLD0403).

SEQ ID NO: 11 shows the codon optimised polynucleotide sequence encoding EcoExo I C98S/C306S/C330T/C144T (ONLD0404).

SEQ ID NO: 12 shows the amino acid sequence of EcoExo I C98S/C306S/C330T/C144T (ONLD0404).

SEQ ID NO: 13 shows the codon optimised polynucleotide sequence encoding EcoExo I C51A/C98S/C144M/C306S/C330TN42C (ONLD0415).

SEQ ID NO: 14 shows the amino acid sequence of EcoExo I C51A/C98S/C144M/C306S/C330TN42C (ONLD0415).

SEQ ID NO: 15 shows the codon optimised polynucleotide sequence encoding EcoExo I C51A/C98S/C144T/C306S/C330TN42C (ONLD0416).

SEQ ID NO: 16 shows the amino acid sequence of EcoExo I C51A/C98S/C144T/C306S/C330TN42C (ONLD0416).

SEQ ID NO: 17 shows the codon optimised polynucleotide sequence encoding EcoExo I C51A/C98S/C144M/C306S/C330T/M184C (ONLD0417).

SEQ ID NO: 18 shows the amino acid sequence of EcoExo I C51A/C98S/C144M/C306S/C330T/M184C (ONLD0417).

SEQ ID NO: 19 shows the codon optimised polynucleotide sequence encoding EcoExo I C51A/C98S/C144T/C306S/C330T/M184C (ONLD0418).

SEQ ID NO: 20 shows the amino acid sequence of EcoExo I C51A/C98S/C144T/C306S/C330T/M184C (ONLD0418).

SEQ ID NO: 21 shows the codon optimised polynucleotide sequence encoding EcoExo I C51A/C98S/C144T/C306S/C330T (ONLD0411).

SEQ ID NO: 22 shows the amino acid sequence of EcoExo I C51A/C98S/C144T/C306S/C330T (ONLD0411).

SEQ ID NO: 23 shows the codon optimised polynucleotide sequence encoding EcoExo I C51A/C98T/C144T/C306S/C330T (ONLD0432).

SEQ ID NO: 24 shows the amino acid sequence of EcoExo I C51A/C98T/C144T/C306S/C330T (ONLD0432).

SEQ ID NO: 25 shows the codon optimised polynucleotide sequence encoding EcoExo I C51A/C98T/C144T/C306T/C330T (ONLD0433).

SEQ ID NO: 26 shows the amino acid sequence of EcoExo I C51A/C98T/C144T/C306T/C330T (ONLD0433).

SEQ ID NO: 27 shows the codon optimised polynucleotide sequence encoding EcoExo I C51A/C98T/C144M/C306S/C330T (ONLD0451).

SEQ ID NO: 28 shows the amino acid sequence of EcoExo I C51A/C98T/C144M/C306S/C330T (ONLD0451).

SEQ ID NO: 29 shows the codon optimised polynucleotide sequence encoding EcoExo I C51A/C98T/C144M/C306T/C330T (ONLD0452).

SEQ ID NO: 30 shows the amino acid sequence of EcoExo I C51A/C98T/C144M/C306T/C330T (ONLD0452).

SEQ ID NO: 31 shows the codon optimised polynucleotide sequence encoding EcoExo I C51A/C98G/C144T/C306S/C330T (ONLD0453).

SEQ ID NO: 32 shows the amino acid sequence of EcoExo I C51A/C98G/C144T/C306S/C330T (ONLD0453).

SEQ ID NO: 33 shows the codon optimised polynucleotide sequence encoding EcoExo I C51A/C98D/C144T/C306S/C330T (ONLD0491).

SEQ ID NO: 34 shows the amino acid sequence of EcoExo I C51A/C98D/C144T/C306S/C330T (ONLD0491).

SEQ ID NO: 35 shows the codon optimised polynucleotide sequence encoding EcoExo I C51A/C98K/C144T/C306S/C330T (ONLD0454).

SEQ ID NO: 36 shows the amino acid sequence of EcoExo I C51A/C98K/C144T/C306S/C330T (ONLD0454).

SEQ ID NO: 37 shows the codon optimised polynucleotide sequence encoding EcoExo I C51A/C98L/C144T/C306S/C330T (ONLD0455).

SEQ ID NO: 38 shows the amino acid sequence of EcoExo I C51A/C98L/C144T/C306S/C330T (ONLD0455).

SEQ ID NO: 39 shows the codon optimised polynucleotide sequence encoding EcoExo I C51A/C98V/C144T/C306S/C330T (ONLD0456).

SEQ ID NO: 40 shows the amino acid sequence of EcoExo I C51A/C98V/C144T/C306S/C330T (ONLD0456).

SEQ ID NO: 41 shows the codon optimised polynucleotide sequence encoding EcoExo I C51A/C98V/C144T/C306T/C330T (ONLD0476).

SEQ ID NO: 42 shows the amino acid sequence of EcoExo I C51A/C98V/C144T/C306T/C330T (ONLD0476).

SEQ ID NO: 43 shows the codon optimised polynucleotide sequence encoding EcoExo I C51A/C98T/C144T/C306M/C330T (ONLD0477).

SEQ ID NO: 44 shows the amino acid sequence of EcoExo I C51A/C98T/C144T/C306M/C330T (ONLD0477).

SEQ ID NO: 45 shows the codon optimised polynucleotide sequence encoding EcoExo I C51A/C98T/C144T/C306N/C330T (ONLD0478).

SEQ ID NO: 46 shows the amino acid sequence of EcoExo I C51A/C98T/C144T/C306N/C330T (ONLD0478).

SEQ ID NO: 47 shows the codon optimised polynucleotide sequence encoding EcoExo I C51A/C98T/C144T/C306D/C330T (ONLD0479).

SEQ ID NO: 48 shows the amino acid sequence of EcoExo I C51A/C98T/C144T/C306D/C330T (ONLD0479).

SEQ ID NO: 49 shows the codon optimised polynucleotide sequence encoding EcoExo I C51A/C98T/C144T/C306A/C330T (ONLD0480).

SEQ ID NO: 50 shows the amino acid sequence of EcoExo I C51A/C98T/C144T/C306A/C330T (ONLD0480).

In all of the mutants described in SEQ ID NOs: 7 to 50, the same amino acids that form α-helices, β-strands and loop regions in wild type EcoExo I form the corresponding regions in this mutant.

SEQ ID NO: 51 shows the codon optimised polynucleotide sequence derived from the xthA gene from *E. coli*. It encodes the exonuclease III enzyme from *E. coli*.

SEQ ID NO: 52 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides. Amino acids 11 to 13, 15 to 25, 39 to 41, 44 to 49, 85 to 89, 121 to 139, 158 to 160, 165 to 174, 181 to 194, 198 to 202, 219 to 222, 235 to 240 and 248 to 252 form α-helices. Amino acids 2 to 7, 29 to 33, 53 to 57, 65 to 70, 75 to 78, 91 to 98, 101 to 109, 146 to 151, 195 to 197, 229 to 234 and 241 to 246 form β-strands. All the other non-terminal amino acids, 8 to 10, 26 to 28, 34 to 38, 42, 43, 50 to 52, 58 to 64, 71 to 74, 79 to 84, 90, 99, 100, 110 to 120, 140 to 145, 152 to 157, 161 to 164, 175 to 180, 203 to 218, 223 to 228, 247 and 253 to 261, form loops. Amino acids 1, 267 and 268 are terminal amino acids. The enzyme active site is formed by loop regions connecting $\beta_1$-$\alpha_1$, $\beta_3$-$\beta_4$, $\beta_5$-$\beta_6$, $\beta_{III}$-$\alpha_I$, $\beta_{IV}$-$\alpha_{II}$ and $\beta_V$-$\beta_{VI}$ (consisting of amino acids 8-10, 58-64, 90, 110-120, 152-164, 175-180, 223-228 and 253-261 respectively). A single divalent metal ion is bound at residue E34 and aids nucleophilic attack on the phosphodiester bond by the D229 and H259 histidine-aspartate catalytic pair.

SEQ ID NO: 53 shows the codon optimised polynucleotide sequence derived from the recJ gene from *T. thermophilus*. It encodes the RecJ enzyme from *T. thermophilus* (TthRecJ-cd).

SEQ ID NO: 54 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides. Amino acids 19 to 33, 44 to 61, 80 to 89, 103 to 111, 136 to 140, 148 to 163, 169 to 183, 189 to 202, 207 to 217, 223 to 240, 242 to 252, 254 to 287, 302 to 318, 338 to 350 and 365 to 382 form α-helices. Amino acids 36 to 40, 64 to 68, 93 to 96, 116 to 120, 133 to 135, 294 to 297, 321 to 325, 328 to 332, 352 to 355 and 359 to 363 form β-strands. All the other non-terminal amino acids, 34, 35, 41 to 43, 62, 63, 69 to 79, 90 to 92, 97 to 102, 112 to 115, 121 to 132, 141 to 147, 164 to 168, 184 to 188 203 to 206, 218 to 222, 241, 253, 288 to 293, 298 to 301, 319, 320, 326, 327, 333 to 337, 351 to 358 and 364, form loops. Amino acids 1 to 18 and 383 to 425 are terminal amino acids. The crystal structure has only been resolved for the core domain of RecJ from *Thermus thermophilus* (residues 40-463). To ensure initiation of translation and in vivo expression of the RecJ core domain a methionine residue was added at its amino terminus, this is absent from the crystal structure information. The resolved structure shows two domains, an amino (2-253) and a carboxyl (288-463) region, connected by a long α-helix (254-287). The catalytic residues (D46, D98, H122, and D183) co-ordinate a single divalent metal ion for nucleophilic attack on the phosphodiester bond. D46 and H120 proposed to be the catalytic pair; however, mutation of any of these conserved residues in the *E. coli* RecJ was shown to abolish activity.

SEQ ID NO: 55 shows the codon optimised polynucleotide sequence derived from the bacteriphage lambda exo (redX) gene. It encodes the bacteriophage lambda exonuclease.

SEQ ID NO: 56 shows the amino acid sequence of the bacteriophage lambda exonuclease. The sequence is one of three identical subunits that assemble into a trimer. The enzyme performs highly processive digestion of nucleotides from one strand of dsDNA, in a 3'-5' direction. Enzyme initiation on a strand preferentially requires a 5' overhang of approximately 4 nucleotides with a 5' phosphate. Amino acids 3 to 10, 14 to 16, 22 to 26, 34 to 40, 52 to 67, 75 to 95, 135 to 149, 152 to 165 and 193 to 216 form α-helices. Amino acids 100 to 101, 106 to 107, 114 to 116, 120 to 122, 127 to 131, 169 to 175 and 184 to 190 form β-strands. All the other non-terminal amino acids, 11 to 13, 17 to 21, 27 to 33, 41 to 51, 68 to 74, 96 to 99, 102 to 105, 108 to 113, 117 to 119, 123 to 126, 132 to 134, 150 to 151, 166 to 168, 176 to 183, 191 to 192, 217 to 222, form loops. Amino acids 1, 2 and 226 are terminal amino acids. Lambda exonuclease is a homo-trimer that forms a toroid with a tapered channel through the middle, apparently large enough for dsDNA to enter at one end and only ssDNA to exit at the other. The catalytic residues are undetermined but a single divalent metal ion appears bound at each subunit by residues D119, E129 and L130.

SEQ ID NO: 57 shows the nucleic sequence from which preferred nucleic acid linkers can be generated.

SEQ ID NO: 58 shows a preferred nucleic acid linker. MAL is maleimide. This linker is used in combination with SEQ ID NO: 61.

SEQ ID NO: 59 shows a preferred nucleic acid linker. MAL is maleimide. This linker is used in combination with SEQ ID NO: 62.

SEQ ID NO: 60 shows a preferred nucleic acid linker. MAL is maleimide. This linker is used in combination with SEQ ID NO: 63.

SEQ ID NO: 61 shows a preferred nucleic acid linker. MAL is maleimide. This linker is complementary to and used in combination with SEQ ID NO: 58.

SEQ ID NO: 62 shows a preferred nucleic acid linker. MAL is maleimide. This linker is complementary to and used in combination with SEQ ID NO: 59.

SEQ ID NO: 63 shows a preferred nucleic acid linker. MAL is maleimide. This linker is complementary to and used in combination with SEQ ID NO: 60.

SEQ ID NO: 64 shows a preferred nucleic acid linker. This linker is used in combination with SEQ ID NO: 65.

SEQ ID NO: 65 shows a preferred nucleic acid linker. This linker is used in combination with SEQ ID NO: 64.

SEQ ID NO: 66 shows a preferred nucleic acid linker. This linker is used in combination with SEQ ID NO: 68.

SEQ ID NO: 67 shows a preferred nucleic acid linker. This linker is used in combination with SEQ ID NO: 69.

SEQ ID NO: 68 shows a preferred nucleic acid linker. This linker is complementary to and used in combination with SEQ ID NO: 66.

SEQ ID NO: 69 shows a preferred nucleic acid linker. This linker is complementary to and used in combination with SEQ ID NO: 67.

SEQ ID NO: 70 shows a preferred nucleic acid linker. This linker is complementary to and used in combination with SEQ ID NO: 73.

SEQ ID NO: 71 shows a preferred nucleic acid linker. This linker is complementary to and used in combination with SEQ ID NO: 74.

SEQ ID NO: 72 shows a preferred nucleic acid linker. This linker is used in combination with SEQ ID NO: 75.

SEQ ID NO: 73 shows a preferred nucleic acid linker. This linker is used in combination with SEQ ID NO: 70.

SEQ ID NO: 74 shows a preferred nucleic acid linker. This linker is used in combination with SEQ ID NO: 71.

SEQ ID NO: 75 shows a preferred nucleic acid linker. This linker is complementary to and used in combination with SEQ ID NO: 72.

SEQ ID NO: 76 shows a preferred nucleic acid linker. This linker is used in combination with SEQ ID NO: 77.

SEQ ID NO: 77 shows a preferred nucleic acid linker. This linker is used in combination with SEQ ID NO: 76.

SEQ ID NO: 78 shows a preferred nucleic acid linker. This linker is complementary to and used in combination with SEQ ID NO: 67.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a linker" includes "linkers", reference to "a transmembrane protein pore" includes two or more such pores, reference to "a moiety" includes two or more such moieties, and the like.

All publications, patents and patent applications cited herein, whether supra or infra, are hereby incorporated by reference in their entirety.

Methods

The invention provides a method for coupling two or more moieties. The invention involves the use of (1) two or more linkers each comprising a hybridizable region and (2) two or more groups capable of forming a covalent bond. The hybridizable regions in the linkers hybridize and link the moieties. The linked moieties are then coupled via the formation of covalent bonds between the groups.

The method of the invention covalently couples two or more moieties. The method comprises providing a first moiety having covalently attached thereto (i) at least one first linker comprising a first hybridizable region and (ii) at least one first group capable of forming a covalent bond. The method also comprises providing a second moiety having covalently attached thereto (i) at least one second linker comprising a second hybridizable region capable of hybridizing to the first hybridizable region and (ii) at least a second group capable of forming a covalent bond with the first group. The first and second moieties are contacted under conditions that allow the first and second hybridizable regions to hybridize and link the moieties. The high affinity of the hybridization reaction allows the moieties to be linked at low concentrations. This is discussed in more detail below. The linked moieties are then exposed to conditions that allow the formation of a covalent bond between the first and second groups. The formation of one or more covalent bonds strengthens the link between the two moieties and results in a more stable complex than would be achieved using just hybridization.

It is preferred that none of the groups used in the invention react with themselves. This improves the yield of the method when two or more different moieties are being coupled because it prevents a moiety from coupling with another version of itself rather than to the different moiety to which it should be coupled.

In one embodiment, the at least one first group is covalently attached directly to the first moiety or is attached to the first moiety via a separate linker (i.e. a different linker from the first linker) and/or the at least one second group is covalently attached directly to the second moiety or is attached to the second moiety via a separate linker (i.e. a different linker from the second linker). The separate linker may be any type of linker. Suitable linkers are known in the art and may be any of the linkers discussed in more detail below.

In another, more preferred, embodiment, the at least one first group is covalently attached to the first moiety via the first linker and/or the at least one second group is covalently attached to the second moiety via the second linker. In this embodiment, the first moiety preferably has covalently attached thereto at least one first linker comprising both a first hybridizable region and a first group capable of forming a covalent bond and/or the second moiety preferably has covalently attached thereto at least one second linker comprising a second hybridizable region capable of hybridizing to the first hybridizable region and a second group capable of forming a covalent bond with the first group. In the most preferred embodiment, the first and second groups are covalently attached to the first and second moieties via the first and second linkers respectively. Hence, in a preferred embodiment, the method comprises (a) providing a first moiety having covalently attached thereto at least one first linker comprising a first hybridizable region and a first group capable of forming a covalent bond; (b) providing a second moiety having covalently attached thereto at least one second linker comprising a second hybridizable region capable of hybridizing to the first hybridizable region and a second group capable of forming a covalent bond with the first group; (c) contacting the first and second moieties under conditions that allow the first and second hybridizable regions to hybridize and link the moieties; and (d) exposing the linked moieties to conditions that allow the formation of a covalent bond between the first and second groups.

Each moiety has covalently attached thereto at least one linker. Methods for covalently attaching linkers to moieties are well-known in the art. For instance, the linker may be attached a cysteine residue is a protein moiety via a disulphide bond. This is discussed in more detail below. Each moiety may have more than one linker, such as 2, 3, 4 or more linkers, covalently attached thereto. In such embodiments, the two or more moieties being coupled typically have the same number of linkers covalently attached thereto. However, the two or more moieties being coupled may each have different numbers of linkers covalently attached thereto. This is also discussed in more detail below.

If more than one linker is used per moiety, it is preferred that linkers on each moiety form pairs that attach together. In other words, the hybriziable regions of two linkers on respective moieties are preferably capable of specifically hybridizing to each other. The most straightforward way of achieving this is to design the hybridizable regions of two linkers such that they only hybridize to each other and not to any of the other hybridization regions being used in the invention. If the first and second groups are attached to the first and second linkers, pairs of linkers may also be formed using click chemistry as described below.

In a preferred embodiment, the first moiety has 2, 3 or 4 first linkers covalently attached thereto and the second moiety has the corresponding number of second linkers attached thereto and the linkers form one or more pairs of first and second linkers in which the hybridizable regions in each pair specifically hybridize to each other but do not hybridize to any of the hybridizable regions in the other the pairs. In this embodiment, the moieties will be form a stable complex because they will be coupled by 2, 3 or 4 covalent bonds. This embodiment can also be used to fix the two moieties in a desired orientation.

In a more preferred embodiment, the moieties are coupled by two linkers and the method comprises (a) providing a first moiety having covalently attached thereto (i) a first linker comprising a first hybridizable region, (i) a first group capable of forming a covalent bond, (iii) a third linker comprising a third hybridizable region and (iv) a third group capable of forming a covalent bond; (b) providing a second moiety having covalently attached thereto (i) a second linker comprising a second hybridizable region capable of hybridizing to the first hybridizable region, (ii) a second group capable of forming a covalent bond with the first group, (iii) a fourth linker comprising a fourth hybridizable region capable of hybridizing to the third hybridizable region and (iv) a fourth group capable of forming a covalent bond with the third group; (c) contacting the first and second moieties under conditions that allow the first and second hybridizable regions to hybridize and allow the third and fourth hybridizable regions to hybridize and link the moieties; and (d) exposing the linked moieties to conditions that allow the formation of a covalent bond between the first and second groups and the third and fourth groups. In a more preferred embodiment, the method comprises (a) providing a first moiety having covalently attached thereto (1) a first linker comprising a first hybridizable region and a first group capable of forming a covalent bond and (2) a third linker comprising a third hybridizable region and a third group capable of forming a covalent bond; (b) providing a second moiety having covalently attached thereto (1) a second linker comprising a second hybridizable region capable of hybridizing to the first hybridizable region and a second group capable of forming a covalent bond with the first group and (2) a fourth linker comprising a fourth hybridizable region capable of hybridizing to the third hybridizable region and a fourth group capable of forming a covalent bond with the third group; (c) contacting the first and second moieties under conditions that allow the first and second hybridizable regions to hybridize and allow the third and fourth hybridizable regions to hybridize and link the moieties; and (d) exposing the linked moieties to conditions that allow the formation of a covalent bond between the first and second groups and the third and fourth groups.

It is preferred that the first hybridizable region does not hybridize to the third and fourth hybridizable regions, that the second hybridizable region does not hybridize to the third and fourth hybridizable regions, that the third hybridizable region does not hybridize to the first and second hybridizable region and that the fourth hybridizable region does not hybridize to the first and second hybridizable regions.

There are also advantages to coupling the two or more moieties using different numbers of linkers on each moiety. For instance, the relative orientations of the moieties can be controlled. In one embodiment, one of the moieties has 2, 3 or 4 linkers and the other moiety has only one linker. The single or individual linker will of course need to comprise 2, 3 or 4 hybridizable regions that are capable of hybridizing to the hybridizable regions of the multiple linkers on the corresponding moiety. Hybridization to the multiple linkers may cause the single or individual linker to bend or flex. In a preferred embodiment, the first moiety has covalently attached thereto (i) a first linker comprising a first hybridizable region, (ii) a first group capable of forming a covalent bond, (iii) a third linker comprising a third hybridizable region and (iv) a third group capable of forming a covalent bond and the second moiety has covalently attached thereto (i) a second linker comprising a second hybridizable region capable of hybridizing to the first hybridizable region and a fourth hybridizable region capable of hybridizing to the third hybridizable region, (ii) a second group capable of forming a covalent bond with the first group and (iii) a fourth group capable of forming a covalent bond with the third group. In a more preferred embodiment, the first moiety has a first linker and a third linker covalently attached thereto and the second moiety has a second linker covalently attached thereto, wherein the first linker comprises a first hybridizable region and a first group capable of forming a covalent bond, wherein the third linker comprises a third hybridizable region and a third group capable of forming a covalent bond and wherein the second linker comprises a second hybridizable region capable of hybridizing to the first hybridizable region, a fourth hybridizable region capable of hybridizing to the third hybridizable region and second and fourth groups capable of forming covalent bonds with the first and third groups.

Each moiety has covalently attached thereto at least one group. Methods for covalently attaching groups to the moieties or the linkers are well-known in the art. This is discussed in more detail below. Each moiety may have more than one group, such as 2, 3, 4 or more groups, covalently attached thereto. This allows the formation of a strong complex containing the moieties. The linkers and groups can also be designed to fix the moieties in a desired spatial orientation relative to each other. Multiple groups may also be used to constrain the mobility of the moieties relative to each other. For instance, multiple groups may be used to constrain the freedom of one moiety to rotate or its ability to move away from the other moiety.

More than two moieties, such as 3, 4, 5, 6 or more moieties, may be coupled in accordance with the invention. This allows complexes comprising several moieties to be produced. It also allows complexes comprising several moieties in a particular arrangement to be produced. For instance, the hybridizing regions or the groups of the linkers can be designed such that they couple the moieties in a particular arrangement. For instance, if three moieties are used (A, B and C), they can be coupled in each of the specific arrangements, namely A-B-C, A-C-B, B-A-C, B-C-A, C-A-B and C-B-A. The terminal moieties of any of these arrangements can also be coupled together to form a "loop" of moieties.

A person skilled in the art will be able to design suitable moiety and linker combinations to allow the moieties to be linked. For instance, if three moieties are used (A, B and C) as described above, A-B-C can be formed by providing B with two linkers covalently attached thereto, one of which allows coupling via a single linker on A and the other of which allows coupling via a single linker on B. Alternatively, each moiety may have two linkers covalently attached thereto. If one of the linkers on A allows coupling via one of the linkers on B, the other linker on B allows couplvia one of the linkers on C and the other linker on C allows coupling via the remaining linker on A, the three moieties may be coupled in a "loop". Multiple linkers may also be used to couple each moiety as discussed above.

In yet a further embodiment, the linkers may be designed to self-assemble into a structure to which the moieties are covalently attached. Nucleic acid self-assembly is well-known in the art. The interactions between synthetic oligonucleotides, and thus the structures that they form by hybridization, can be controlled through design of their nucleotide sequences using simple rules (Watson-Crick base pairing, supplemented by rules prescribing the design of structural motifs such as junctions, G-quadruplexes, i-motifs etc.). For instance, Seeman et al. have prepared various three-dimensional DNA lattices (for example N C Seeman et al., *J. Theor. Biol.* 99, 237 (1982)). The self-assembled structure is coupled by the covalent bonds formed between the groups on the linkers.

In a preferred embodiment, the method comprises coupling 3, 4 or 5 moieties and wherein each moiety has covalently attached thereto (i) at least one linker which comprises a hybridizable region capable of hybridizing to the hybridizable region of a linker on a different moiety and (ii) at least one covalent group capable of forming a covalent bond with the group on a different moiety. In a more preferred embodiment, the method comprises coupling 3, 4 or 5 moieties and wherein each moiety has at least one linker covalently attached thereto which comprises hybridizable regions capable of hybridizing to the hybridizable region of another linker and a covalent group capable of forming a covalent bond with the group on another linker.

In an even more preferred embodiment, the method comprises a) providing a first moiety having covalently attached thereto (i) a first linker comprising a first hybridizable region and (ii) a first group capable of forming a covalent bond; b) providing a second moiety having covalently attached thereto (i) a second linker comprising a second hybridizable region capable of hybridizing to the first hybridizable region and (ii) a second group capable of forming a covalent bond with the first group, (ii) a third linker comprising a third hybridizable region and (iv) a third group capable of forming a covalent bond; c) providing a third moiety having covalently attached thereto (i) a fourth linker comprising a fourth hybridizable region capable of hybridizing to the third hybridizable region, (ii) a fourth group capable of forming a covalent bond with the third group; d) contacting the first, second and third moieties under conditions that allow the hybridizable regions to hybridize and link the moieties; and d) exposing the linked moieties to conditions that allow the formation of a covalent bond between the groups.

In an even more preferred embodiment, the method comprises (a) providing a first moiety having covalently attached thereto a first linker comprising a first hybridizable region and a first group capable of forming a covalent bond; (b) providing a second moiety having covalently attached thereto (1) a second linker comprising a second hybridizable region capable of hybridizing to the first hybridizable region and a second group capable of forming a covalent bond with the first group and (2) a third linker comprising a third hybridizable region and a third group capable of forming a covalent bond; (c) providing a third moiety having covalently attached thereto a fourth linker comprising a fourth hybridizable region capable of hybridizing to the third hybridizable region and a fourth group capable of forming a covalent bond with the third group; (d) contacting the first, second and third moieties under conditions that allow the hybridizable regions to hybridize and link the moieties; and (e) exposing the linked moieties to conditions that allow the formation of a covalent bond between the groups.

Moieties

The two or more moieties may be any substance or surface that may be covalently coupled using linkers. Preferred moieties include, but are not limited to, polypeptides, proteins, nucleic acids, chemical groups, dyes, affinity tags, polymers, beads, antibodies, supports, immobilised metal affinity matrices, glutathione sepharose, dextrin sepharose, affinity matrices, IgG sepharoses, activated thiol-sepharoses, metal films, nanoparticles, glass, treated glass, plastics, resin surfaces, solid state nanopores, sensor surfaces and single molecular detectors.

Suitable solid state pores include, but are not limited to, silicon nitride pores, silicon dioxide pores and graphene pores. Other suitable solid state pores and methods of producing them are discussed in U.S. Pat. No. 6,464,842, WO 03/003446, WO 2005/061373, U.S. Pat. No. 7,258,838, U.S. Pat. No. 7,466,069, U.S. Pat. No. 7,468,271 and U.S. Pat. No. 7,253,434.

The two or more moieties may be the same or different.

It is preferred that the first moiety is a protein and the second moiety is a protein, a nucleic acid, a reporter group, an affinity tag or a support. The two or more moieties may be attached in any configuration. For instance, if they are proteins, they may be attached via their terminal (i.e. amino or carboxy terminal) amino acids.

It is more preferred that the first moiety is a nucleic acid binding protein and the second moiety is a transmembrane protein pore. Suitable configurations include, but are not limited to, the amino terminus of the nucleic acid binding protein being attached to the carboxy terminus of the transmembrane protein pore and vice versa. Alternatively, the two components may be attached via amino acids within their sequences. For instance, the nucleic acid binding protein may be attached to one or more amino acids in a loop region of the moiety. In a preferred embodiment, terminal amino acids of the nucleic acid binding protein are attached to one or more amino acids in the loop region of the moiety. Terminal amino acids and loop regions are discussed below.

If the first moiety is a nucleic acid binding protein and the second moiety is a transmembrane protein pore, the first and second groups are preferably from 0.05 nm to 10 nm from their respective moieties, more preferably from 0.05 nm to 5 nm and most preferably about 0.1 nm, or 3 nucleotides, from their respective moieties. If the first moiety is a nucleic acid binding protein and the second moiety is a transmembrane protein pore, the distance between the coupled first and second moieties is preferably from 0.1 nm to 100 nm, more preferably from 0.1 nm to 25 nm, more preferably from 0.1 nm to 5 nm and most preferably 0.5 nm. To achieve distances of around 0.5 nm between moieties it will be necessary to have the attached linkers in a "head to head" arrangement. If the linkers are used in a "head to tail" arrangement, a minimum of 5 or 6 nucleotides in each linker is needed to provide sufficient hybridization. Shorter linkers will not hybridize adequately, if at all, and thus shorter moiety-moiety distances can only be achieved using a different conformation.

In a preferred embodiment, the site of covalent attachment is selected such that, when the moiety is a pore, the nucleic acid binding protein handles a target nucleic acid sequence in such a way that a proportion of the nucleotides in the target sequence interacts with the pore. Nucleotides are then distinguished on the basis of the different ways in which they affect the current flowing through the pore during the interaction.

There are a number of ways that pores can be used to sequence nucleic acid molecules. One way involves the use of an exonuclease enzyme, such as a deoxyribonuclease. In this approach, the exonuclease enzyme is used to sequentially detach the nucleotides from a target nucleic strand. The nucleotides are then detected and discriminated by the pore in order of their release, thus reading the sequence of the original strand. For such an embodiment, the exonuclease enzyme is preferably attached to a pore subunit such that a proportion of the nucleotides released from the target nucleic acid is capable of entering and interacting with the barrel or channel of a pore comprising the subunit. The exonuclease is preferably attached to the subunit at a site in close proximity to the part of the subunit that forms the opening of the barrel of channel of the pore. The exonuclease enzyme is more preferably attached to the subunit such that its nucleotide exit trajectory site is orientated towards the part of the subunit that forms part of the opening of the pore.

Another way of sequencing nucleic acids involves the use of an enzyme that pushes or pulls the target nucleic acid strand through the pore in combination with an applied potential. In this approach, the ionic current fluctuates as a nucleotide in the target strand passes through the pore. The fluctuations in the current are indicative of the sequence of the strand. For such an embodiment, the enzyme is preferably attached to a pore subunit such that it is capable of pushing or pulling the target nucleic acid through the barrel or channel of a pore comprising the subunit and does not interfere with the flow of ionic current through the pore. The enzyme is preferably attached to the subunit at a site in close proximity to the part of the subunit that forms part of the opening of the barrel of channel of the pore. The enzyme is more preferably attached to the subunit such that its active site is orientated towards the part of the subunit that forms part of the opening of the pore.

A third way of sequencing a nucleic acid strand is to detect the byproducts of a polymerase in close proximity to a pore detector. In this approach, nucleoside phosphates (nucleotides) are labelled so that a phosphate labelled species is released upon the addition of a polymerase to the nucleotide strand and the phosphate labelled species is detected by the pore. The phosphate species contains a specific label for each nucleotide. As nucleotides are sequentially added to the nucleic acid strand, the bi-products of the base addition are detected. The order that the phosphate labelled species are detected can be used to determine the sequence of the nucleic acid strand.

The nucleic acid binding protein is preferably attached to the part of a pore or a subunit thereof that forms part of the cis side of a pore. In electrophysiology, the cis side is the grounded side by convention. If a hemolysin pore is inserted correctly into an electrophysiology apparatus, the Cap region is on the cis side. It is well known that, under a positive potential, nucleotides will migrate from the cis to the trans side of pores used for stochastic sensing. Positioning the nucleic acid binding protein at the cis side of a pore allows it to handle the target nucleic acid such that a proportion of the nucleotides in the sequence enters the barrel or channel of the pore and interacts with it. Preferably, at least 20%, at least 40%, at least 50%, at least 80% or at least 90% of the nucleotides in the sequence enters the barrel or channel of the pore and interacts with it.

The site and method of covalent attachment is preferably selected such that mobility of the nucleic acid binding protein is constrained. This helps to ensure that the protein handles the target nucleic acid sequence in such a way that a proportion of the nucleotides in the target sequence interacts with the pore. For instance, constraining the ability of nucleic acid binding protein to move means that its active site can be permanently orientated towards the part of the subunit that forms part of the opening of the barrel of channel of the pore. The mobility of the nucleic acid binding protein may be constrained by increasing the number of points at which the protein is attached to the moiety and/or the use of specific linkers.

Biologically active moieties are typically coupled in such a way that they retain their biological activity. The biological activity of any of the moieties described herein can be determined using methods well-known in the art. If a nucleic acid binding protein and a transmembrane protein pore are coupled together, both proteins preferably retain their binding and pore properties respectively.

If one or more of the moieties is a protein, at least one native accessible cysteine residue may be removed from the protein as described in a co-pending International application claiming priority from U.S. Application No. 61/148,726 and being filed simultaneously with this application [J A Kemp & Co Ref: N.106566A; Oxford Nanopore Technologies Ref: ONL IP 007]. However, the protein may comprise one or more accessible cysteine residues and may be attached to the other moieties via those residues. The presence of a limited number of accessible cysteine residues allows controlled coupling between moieties.

The ionisable side chain of cysteine residues is a potent nucleophile for engaging in addition reactions and so is a popular choice for use in bioconjugation techniques. However, a common barrier to the effective use of these techniques is the native cysteine residues present in wild type proteins. Modification of one or more of the native cysteine residues can cause both ambiguous enzyme activity and uncontrolled linkage.

The invention may involve site directed mutagenesis of native cysteine residues from protein moieties. All but one or more of the accessible native cysteines can be removed. Alternatively, all the accessible cysteine residues can be removed and one or more cysteine residues can be introduced to the protein. The presence of specific accessible cysteine residues facilitates the attachment of the binding protein to another moiety, such as another protein, a solid support or a chemical reagent.

Removal of native cysteine residues and targeted addition of single or multiple cysteine residue improves on previous methodologies as it conveys the ability to control coupling, while also minimising the possible interaction of the proteins with one another to form dimers, trimers and the like via undesired surface thiols. If the protein contains only a single cysteine residue at a designed position in its structure, then the thiol group of that residue can be used to form either a direct disulphide bond with other sulfhydryl groups or coupling can be mediated by a reactive linker. These targeted cysteine residues ensure only the desired number of enzyme molecules cross-link to the desired number of target molecules, whilst also conferring a degree of favourable conformation, so that for instance active sites can be optimally orientated.

The native cysteine residues present in wild type proteins do not readily permit the use of specific linkers containing thiol reactive groups, such as maleimide, iodoactemide or ortho-pyridyl disulphide (OPSS). The potential for reaction with any structurally or catalytically important cysteine residues could impact upon the protein's activity, which is of particular importance for use in single molecule applications. The use of linkers for bioconjugation is preferred to ensure some spatial separation so that protein activity is not affected by being in close proximity to another moiety, such as a protein or a surface.

Nucleic Acid Binding Protein

One of the moieties is preferably a nucleic acid binding protein. Examples of such proteins include, but are not limited to, nucleic acid handling enzymes, such as nucleases, polymerases, topoisomerases, ligases and helicases, and non-catalytic binding proteins such as those classified by SCOP (Structural Classification of Proteins) under the Nucleic acid-binding protein superfamily (50249). The nucleic acid handling enzyme is modified to remove and/or replace cysteine residues as described above and in a co-pending International application claiming priority from U.S. Application No. 61/148,726 and being filed simultaneously with this application [J A Kemp & Co Ref: N.106566A; Oxford Nanopore Technologies Ref: ONL IP 007]. At least one native accessible cysteine residue is preferably removed from the nucleic acid binding protein. However, the nucleic acid binding protein comprises one or more accessible cysteine residues and is attached to another moiety via those residues. The presence of a limited number of accessible cysteine residues allows controlled attachment to another moiety.

A nucleic acid is a macromolecule comprising two or more nucleotides. The nucleic acid bound by the protein may comprise any combination of any nucleotides. The nucleotides can be naturally occurring or artificial. The nucleotide can be oxidized or methylated. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are preferably selected from AMP, TMP, GMP, CMP, UMP, dAMP, dTMP, dGMP or dCMP.

The nucleic acid can be deoxyribonucleic acid (DNA) or ribonucleic acid (RNA). The nucleic acid may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The nucleic acid bound by the protein is preferably single stranded, such as cDNA, RNA, GNA, TNA or LNA. The nucleic acid bound by the protein is preferably double stranded, such as DNA. Proteins that bind single stranded nucleic acids may be used to sequence double stranded DNA as long as the double stranded DNA is dissociated into a single strand before it is bound by the protein.

It is preferred that the tertiary structure of the nucleic acid binding protein is known. Knowledge of the three dimensional structure of the binding protein allows modifications to be made to the protein to facilitate its function in the coupled structure.

The protein may be any size and have any structure. For instance, the protein may be an oligomer, such as a dimer or trimer. The protein is preferably a small, globular polypeptide formed from one monomer. Such proteins are easy to handle and are less likely to interfere with the other moiety. For instance, such proteins are less likely to interfere with the pore forming ability of a pore subunit.

It is also preferred that the location and function of the active site of the protein is known. This prevents modifications being made to the active site that abolish the activity of the protein. It also allows the protein to be attached to the other moiety so that the protein binds the target nucleic acid sequence in a particular way. For instance, if the protein is being attached to a transmembrane protein pore for sequencing purposes, it allows a proportion of the nucleotides in a target sequence to interact with the pore as described below. In such embodiments, it is beneficial to position the active site of the protein as close as possible to the opening of the barrel of channel of the pore, without the protein itself presenting a block to the flow of current. Knowledge of the way in which a protein may orient nucleic acids also allows an effective coupled structure to be designed.

It may be necessary to purify the structure produced by the method of the invention. It is preferred that the nucleic acid binding protein is capable of withstanding the conditions used to purify the structure.

The other moiety may comprise a pore. Such pores may be used to sequence nucleic acids. In order that most of the nucleotides in the target nucleic acid are correctly identified by stochastic sensing, the protein preferably binds the nucleic acid in a buffer background which is compatible with discrimination of the nucleotides. The protein preferably has at least residual activity in a salt concentration well above the normal physiological level, such as from 100 mM to 2000 mM. The protein is more preferably modified to increase its activity at high salt concentrations. The protein may also be modified to improve its processivity, stability and shelf life.

Suitable modifications can be determined from the characterisation of nucleic acid handling enzymes from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The enzyme also preferably retains at least partial activity at temperatures from 10° C. to 60° C., such as at room temperature. This allows nucleic acids to be sequenced at a variety of temperatures, including room temperature.

The nucleic acid binding protein is preferably a nucleic acid handling enzyme. A nucleic acid handling enzyme is a polypeptide that is capable of interacting with and modifying at least one property of a nucleic acid. The enzyme may modify the nucleic acid by cleaving it to form individual nucleotides or shorter chains of nucleotides, such as di- or trinucleotides. The enzyme may modify the nucleic acid by orienting it or moving it to a specific position.

The nucleic acid handling enzyme is preferably derived from a nucleolytic enzyme. The nucleic acid handling enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The nucleic acid handling enzyme is more preferably based on any one of the following enzymes:

3.1.11.—Exodeoxyribonucleases producing 5'-phosphomonoesters.
  3.1.11.1 Exodeoxyribonuclease I.
  3.1.11.2 Exodeoxyribonuclease III.
  3.1.11.3 Exodeoxyribonuclease (lambda-induced).
  3.1.11.4 Exodeoxyribonuclease (phage SP3-induced).
  3.1.11.5 Exodeoxyribonuclease V.
  3.1.11.6 Exodeoxyribonuclease VII.
3.1.13.—Exoribonucleases producing 5'-phosphomonoesters.
  3.1.13.1 Exoribonuclease II.
  3.1.13.2 Exoribonuclease H.
  3.1.13.3 Oligonucleotidase.
  3.1.13.4 Poly(A)-specific ribonuclease.
  3.1.13.5 Ribonuclease D.
3.1.14.—Exoribonucleases producing 3'-phosphomonoesters.
  3.1.14.1 Yeast ribonuclease.
3.1.15.—Exonucleases active with either ribo- or deoxyribonucleic acid producing 5' phosphomonoesters
  3.1.15.1 Venom exonuclease.
3.1.16.—Exonucleases active with either ribo- or deoxyribonucleic acid producing 3' phosphomonoesters
  3.1.16.1 Spleen exonuclease.
3.1.21.—Endodeoxyribonucleases producing 5'-phosphomonoesters.
  3.1.21.1 Deoxyribonuclease I.
  3.1.21.2 Deoxyribonuclease IV (phage-T(4)-induced).
  3.1.21.3 Type I site-specific deoxyribonuclease.
  3.1.21.4 Type II site-specific deoxyribonuclease.
  3.1.21.5 Type III site-specific deoxyribonuclease.
  3.1.21.6 CC-preferring endodeoxyribonuclease.
  3.1.21.7 Deoxyribonuclease V.
3.1.22.—Endodeoxyribonucleases producing other than 5'-phosphomonoesters.
  3.1.22.1 Deoxyribonuclease II.
  3.1.22.2 Aspergillus deoxyribonuclease K(1).
  3.1.22.3 Transferred entry: 3.1.21.7.
  3.1.22.4 Crossover junction endodeoxyribonuclease.
  3.1.22.5 Deoxyribonuclease X.
3.1.25.—Site-specific endodeoxyribonucleases specific for altered bases.
  3.1.25.1 Deoxyribonuclease (pyrimidine dimer).
  3.1.25.2 Transferred entry: 4.2.99.18.
3.1.26.—Endoribonucleases producing 5'-phosphomonoesters.
  3.1.26.1 Physarum polycephalum ribonuclease.
  3.1.26.2 Ribonuclease alpha.
  3.1.26.3 Ribonuclease III.
  3.1.26.4 Ribonuclease H.
  3.1.26.5 Ribonuclease P.
  3.1.26.6 Ribonuclease IV.
  3.1.26.7 Ribonuclease P4.
  3.1.26.8 Ribonuclease M5.
  3.1.26.9 Ribonuclease (poly-(U)-specific).
  3.1.26.10 Ribonuclease IX.
  3.1.26.11 Ribonuclease Z.
3.1.27.—Endoribonucleases producing other than 5'-phosphomonoesters.
  3.1.27.1 Ribonuclease T(2).
  3.1.27.2 Bacillus subtilis ribonuclease.
  3.1.27.3 Ribonuclease T(1).
  3.1.27.4 Ribonuclease U(2).
  3.1.27.5 Pancreatic ribonuclease.
  3.1.27.6 Enterobacter ribonuclease.
  3.1.27.7 Ribonuclease F.
  3.1.27.8 Ribonuclease V.
  3.1.27.9 tRNA-intron endonuclease.
  3.1.27.10 rRNA endonuclease.
3.1.30.—Endoribonucleases active with either ribo- or deoxyribonucleic producing 5' phosphomonoesters
  3.1.30.1 Aspergillus nuclease S(1).
  3.1.30.2 Serratia marcescens nuclease.
3.1.31.—Endoribonucleases active with either ribo- or deoxyribonucleic producing 3' phosphomonoesters
  3.1.31.1 Micrococcal nuclease.

The enzyme is most preferably derived from an exonuclease, such as a deoxyribonuclease, which cleaves nucleic acids to form individual nucleotides. The advantages of exodeoxyribonucleases are that they are active on both single stranded and double stranded DNA and hydrolyse bases either in the 5'-3' or 3'-5' direction.

An individual nucleotide is a single nucleotide. An individual nucleotide is one which is not bound to another nucleotide or nucleic acid by any bond, such as a phosphodiester bond. A phosphodiester bond involves one of the phosphate groups of a nucleotide being bound to the sugar group of another nucleotide. An individual nucleotide is typically one which is not bound in any manner to another nucleic acid sequence of at least 5, at least 10, at least 20, at least 50, at least 100, at least 200, at least 500, at least 1000 or at least 5000 nucleotides.

Preferred enzymes for use in the invention include exonuclease I from E. coli (SEQ ID NO: 6), exonuclease III enzyme from E. coli (SEQ ID NO: 52), RecJ from T. thermophilus (SEQ ID NO: 54) and bacteriophage lambda exonuclease (SEQ ID NO: 56) and variants thereof. Three identical subunits of SEQ ID NO: 56 interact to form a trimer exonuclease. The enzyme is most preferably based on exonuclease I from E. coli (SEQ ID NO: 6).

The nucleic acid handling enzyme is preferably derived from an exonuclease enzyme comprising any of the sequences shown in SEQ ID NOs: 6, 52, 54 and 56 or a variant thereof. In other words, the enzyme preferably comprises any of the sequences shown in SEQ ID NOs: 6, 52, 54 and 56 or a variant thereof before its cysteine residues are modified as described above.

A variant of SEQ ID NO: 6, 52, 54 or 56 is an enzyme that has an amino acid sequence which varies from that of SEQ ID NO: 6, 52, 54 or 56 and which retains nucleic acid handling ability. The ability of a variant to handle nucleic acids can be assayed using any method known in the art. For instance, the ability of a variant to handle nucleic acids can be assayed as described in the Example. The variant must also retain its ability to be expressed as described in the Example.

The variant may include modifications that facilitate handling of the nucleic acid and/or facilitate its activity at high salt concentrations and/or room temperature.

The enzyme, may be a naturally occurring variant which is expressed by an organism, for instance by an E. coli bacterium. Variants also include non-naturally occurring variants produced by recombinant technology. Over the entire length of the amino acid sequence of SEQ ID NO: 6, 52, 54 or 56, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6, 52, 54 or 56 over the entire sequence. There may be at least 80%, for example at least 85%, 90% or 95%, amino acid identity over a stretch of 200 or more, for example 230, 250, 270 or 280 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Amino acid substitutions may be made to the amino acid sequence of SEQ ID NO: 6, 52, 54 or 56 in addition to those discussed above, for example up to 1, 2, 3, 4, 5, 10, 20 or 30 substitutions. Conservative substitutions may be made, for example, according to Table 1 below.

TABLE 1

Conservative substitutions
Amino acids in the same block in the second column and preferably in the same line in the third column may be substituted for each other.

| NON-AROMATIC | Non-polar | G A P |
| | | I L V |
| | Polar - uncharged | C S T M |
| | | N Q |
| | Polar - charged | D E |
| | | H K R |
| AROMATIC | | H F W Y |

One or more amino acid residues of the amino acid sequence of SEQ ID NO: 6, 52, 54 or 56 may additionally be deleted from the polypeptides described above. Up to 1, 2, 3, 4, 5, 10, 20 or 30 residues may be deleted, or more.

Variants may be fragments of SEQ ID NO: 6, 52, 54 or 56. Such fragments retain nucleic acid handling activity. Fragments may be at least 50, 100, 200 or 250 amino acids in length. A fragment preferably comprises the nucleic acid handling domain of SEQ ID NO: 6, 52, 54 or 56.

One or more amino acids may be alternatively or additionally added to the polypeptides described above. An extension may be provided at the amino terminus or carboxy terminus of the amino acid sequence of SEQ ID NO: 6, 52, 54 or 56 or a variant or fragment thereof. The extension may be quite short, for example from 1 to 10 amino acids in length. Alternatively, the extension may be longer, for example up to 50 or 100 amino acids. A carrier protein may be fused to a subunit or variant.

As discussed above, a variant of SEQ ID NO: 6, 52, 54 or 56 is a protein that has an amino acid sequence which varies from that of SEQ ID NO: 6, 52, 54 or 56 and which retains its ability to handle nucleic acids. A variant typically contains the regions of SEQ ID NO: 6, 52, 54 or 56 that are responsible for handling nucleic acids. The catalytic domains of SEQ ID NOs: 6, 52, 54 and 56 are discussed above in the description of the sequence listing. A variant of SEQ ID NO: 6, 52, 54 or 56 preferably comprises the relevant catalytic domain. A variant SEQ ID NO: 6, 52, 54 or 56 typically includes one or more modifications, such as substitutions, additions or deletions, outside the relevant catalytic domain. Specific variants of SEQ ID NO: 6 are discussed in more detail below.

The variant may be modified for example by the addition of histidine or aspartic acid residues to assist its identification or purification or by the addition of a signal sequence to promote their secretion from a cell where the polypeptide does not naturally contain such a sequence.

Preferred enzymes that are capable of pushing or pulling the target nucleic acid sequence through the pore include polymerases, nucleases, helicases and topoisomerases, such as gyrases. The nucleic acid handling enzyme can be derived from any of these types of enzymes. The polymerase is preferably a member of any of the Enzyme Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The helicase is preferably based on a member of any of the Enzyme Classification (EC) groups 3.6.1.- and 2.7.7.-. The helicase is preferably an ATP-dependent DNA helicase (EC group 3.6.1.8), an ATP-dependent RNA helicase (EC group 3.6.1.8) or an ATP-independent RNA helicase. The topoisomerase is preferably a member of any of the Enzyme Classification (EC) groups 5.99.1.2 and 5.99.1.3.

The nucleic acid binding protein may be labelled with a revealing label. The revealing label may be any suitable label which allows the pore to be detected. Suitable labels include, but are not limited to, fluorescent molecules, radioisotopes, e.g. $^{125}$I, $^{35}$S, $^{14}$C, enzymes, antibodies, antigens, polynucleotides and ligands such as biotin.

The nucleic acid binding protein may be isolated from a binding protein producing organism, such as *E. coli, T. thermophilus* or bacteriophage, or made synthetically or by recombinant means. For example, the nucleic acid binding protein may be synthesised by in vitro translation and transcription. The amino acid sequence of the nucleic acid binding protein may be modified to include non-naturally occurring amino acids or to increase the stability of the protein. When the nucleic acid binding protein is produced by synthetic means, such amino acids may be introduced during production. The nucleic acid binding protein may also be altered following either synthetic or recombinant production.

The nucleic acid binding protein may also be produced using D-amino acids. For instance, the nucleic acid binding proteins may comprise a mixture of L-amino acids and D-amino acids. This is conventional in the art for producing such proteins or peptides.

The nucleic acid binding protein may also contain other non-specific chemical modifications as long as they do not interfere with its ability to handle nucleic acids or attach to the other moiety. A number of non-specific side chain modifications are known in the art and may be made to the side chains of the pores. Such modifications include, for example, reductive alkylation of amino acids by reaction with an aldehyde followed by reduction with NaBH$_4$, amidination with methylacetimidate or acylation with acetic anhydride. The modifications to the nucleic acid binding protein can be made after expression of the nucleic acid binding protein or after the nucleic acid binding protein has been used in the method of the invention.

The nucleic acid binding protein can be produced using standard methods known in the art. Polynucleotide sequences encoding a nucleic acid binding protein may be isolated and replicated using standard methods in the art. Such sequences are discussed in more detail below. Polynucleotide sequences encoding a nucleic acid binding protein may be expressed in a bacterial host cell using standard techniques in the art. The nucleic acid binding protein may be produced in a cell by in situ expression of the polypeptide from a recombinant expression vector. The expression vector optionally carries an inducible promoter to control the expression of the polypeptide.

A nucleic acid binding protein may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system.

The nucleic acid handling enzyme is preferably derived from an exonuclease enzyme comprising the sequence shown in SEQ ID NO: 6 or a variant thereof. In other words, the enzyme preferably comprises the sequence shown in SEQ ID NO: 6 or a variant thereof before its cysteine residues are modified as described above. Variants of SEQ ID NO: 6 are discussed above.

SEQ ID NO: 6 has five native cysteine residues at positions 51, 98, 144, 306 and 330. All five cysteine residues at these positions are accessible. A variant of SEQ ID NO: 6 preferably comprises all five of these residues before it is modified in accordance with the invention.

In one embodiment, all five of the cysteines at positions 51, 98, 144, 306 and 330 are removed from SEQ ID NO: 6 and one or more non-native cysteine residues are introduced.

In another embodiment, all but one or more of the five cysteine residues at positions 51, 98, 144, 306 and 330 are removed from SEQ ID NO: 6. Any combination of one or more of the five cysteine residues at positions 51, 98, 144, 306 and 330 can remain in an enzyme derived from SEQ ID NO: 6 after mutagenesis. Preferred combinations include, but are not limited, to 144 and 330. In a preferred embodiment, only the native cysteine residue at position 144 or 330 of SEQ ID NO: 6 remains.

One or more of the five cysteine residues in SEQ ID NO: 6 are preferably substituted with alanine, serine, methionine or threonine. The cysteine residue at position 51 in SEQ ID NO: 6 is more preferably substituted with alanine. The cysteine residue at position 98 in SEQ ID NO: 6 is more preferably substituted with serine or threonine. The cysteine residue at position 144 in SEQ ID NO: 6 is more preferably substituted with methionine or threonine. The cysteine residue at position 306 in SEQ ID NO: 6 is more preferably substituted with serine or threonine. The cysteine residue at position 330 in SEQ ID NO: 6 is more preferably substituted with threonine. In the most preferred embodiment, the cysteine residue at position 51 in SEQ ID NO: 6 is substituted with alanine, the cysteine residue at position 98 in SEQ ID NO: 6 is substituted with threonine, the cysteine residue at position 144 in SEQ ID NO: 6 is substituted with threonine, the cysteine residue at position 306 in SEQ ID NO: 6 is substituted with threonine and the cysteine residue at position 330 in SEQ ID NO: 6 is substituted with threonine.

The nucleic acid handling enzyme preferably comprises the sequence shown in any one of SEQ ID NOs: 8, 10, 12, 14, 16, 18, 20, 22, 24, 26, 28, 30, 32, 34, 36, 38, 40, 42, 44, 46, 48 and 50 or a variant thereof. A variant of SEQ ID NO: 8, 10, 12, 14, 16, 18, 20, 22, 24, 26, 28, 30, 32, 34, 36, 38, 40, 42, 44, 46, 48 and 50 is a protein that has an amino acid sequence which varies from that of SEQ ID NO: 8, 10, 12, 14, 16, 18, 20, 22, 24, 26, 28, 30, 32, 34, 36, 38, 40, 42, 44, 46, 48 and 50 and which retains its ability to handle nucleic acids. Variants may differ from SEQ ID NO: 8, 10, 12, 14, 16, 18, 20, 22, 24, 26, 28, 30, 32, 34, 36, 38, 40, 42, 44, 46, 48 or 50 to the same extent as variants of SEQ ID NO: 6 differ from SEQ ID NO: 6 as discussed above. However, variants of SEQ ID NOs: 8, 10, 12, 14, 16, 18, 20, 22, 24, 26, 28, 30, 32, 34, 36, 38, 40, 42, 44, 46, 48 and 50 must comprise the changes made compared with the wild type enzyme. For instance, variants of SEQ ID NOs: 8, 10 and 12 must comprise the same residues as SEQ ID NOs: 8, 10 and 12 at positions 98, 144, 306 and 330. Variants of SEQ ID NOs: 14 and 16 must comprise the same residues as SEQ ID NOs: 14 and 16 at positions 42, 51, 98, 144, 306 and 330. Variants of SEQ ID NOs: 18, 20, 22, 24, 26, 28, 30, 32, 34, 36, 38, 40, 42, 44, 46, 48 and 50 must comprise the same residues as SEQ ID NOs: 18, 20, 22, 24, 26, 28, 30, 32, 34, 36, 38, 40, 42, 44, 46, 48 and 50 at positions 51, 98, 144, 184, 306 and 330.

The nucleic acid handling enzyme is typically attached to the moiety via one or more of its surface accessible residues having side chains of a preferred orientation. The following residues in SEQ ID NO: 6 should not be used as attachment points because they are buried and inaccessible to solvent or attachment to a linker will result is severe disruption of the protein global structure: 13, 101, 104, 111, 114, 115, 117, 190, 194, 197, 208, 232, 233, 236, 246, 247, 248, 258, 259, 261, 262, 283, 298, 309, 310, 347, 406, and 267. The following residues in SEQ ID NO: 6 are close to DNA binding groove and would not be a good location to attach a linker even though they are surface accessible: 21, 22, 103, 105, 106, 107, 109, 110, 114, 115, 117, 118, 231, 242, 252, 256, 257, 285, 287, 288, 289, 300, 301, 302, 304, 305, 307, 355, 356, 357, 358, 359, 360 368, 369 and 371. All the remaining residues in SEQ ID NO: 6 could potentially be used as attachment points.

The following residues in SEQ ID NO: 6 are preferred attachment points because they provide a side chain, are exposed and are solvent accessible and mutation of the side chain would be predicted to lead to little disruption of the overall protein structure: 8, 9, 37, 38, 39, 41, 43, 44, 45, 47, 76, 77, 96, 150, 151, 153, 156, 159, 161, 171, 173, 176, 178, 179, 184, 195, 198, 199, 200, 203, 209, 218, 222, 225, 227, 256, 273, 275, 277, 278, 280, 281, 282, 285, 292, 293, 311, 313, 316, 318, 321, 326, 327, 328, 332, 335, 338, 339, 340, 342, 345, 353, 374, 381, 385, 387, 389, 390, 395, 397, 401, 417, 420, 423, 424, 429, 432, 437, 438, 441, 445, 448, 452, 456, 458, 459, 465, 458, 459, 462, 466 and 467. The following residues are most preferred as attachment points: 184, 83, 42, 94, 90, 188, 184, 185, 186, 187, 188, 189, 190, 191, 192, 193, 194, 195, 196, 197, 198, 199, 215, 216, 217, 218, 219, 220, 221, 222 and 223. Any of the preferred attachment residues may be modified by substitution. Preferably one or more of the preferred attachment residues is substituted with cysteine. Preferred substitutions in SEQ ID NO: 6 or a variant thereof include, but are not limited to, M184C, A83C, V42C, V94C, 590C, Y188C, Y188C, A219C, A219C, M218C and M218C. As discussed in more detail below, the enzyme may be attached to the moiety via more than one residue.

The nucleic acid binding protein can be attached to another moiety at one or more positions, such as at one, two, three or four positions. The nucleic acid binding protein is preferably attached at one or two positions. After removal of native cysteine residues from the nucleic acid binding protein, one or more cysteine residues can be incorporated into the protein at specific positions for the attachments. Attachment at two positions can reduce the flexibility of the complex and can fix the nucleic acid binding protein on the moiety in a chosen specific orientation.

In a preferred embodiment, the method comprises coupling (1) exonuclease I from *E. coli* (SEQ ID NO: 6) or a variant thereof with the substitutions M184C and V94C to (2) α-HL (SEQ ID NO: 2) or a variant thereof having the substitutions N17C and E287C. The M184C position in SEQ ID NO: 6 or a variant thereof is coupled to the N17C position in SEQ ID NO: 2 or a variant thereof. The V94C position in SEQ ID NO: 6 or a variant thereof is coupled to the E287C position in SEQ ID NO: 2 or a variant thereof by a different linker.

Table 2 below shows the positions of other preferred first and second attachment points.

| | First A SEQ ID NO: 6 or variant thereof | First B (attached to First A) SEQ ID NO: 2 or variant thereof | Second A SEQ ID NO: 6 or variant thereof | Second B (attached to Second A) SEQ ID NO: 2 or variant thereof |
|---|---|---|---|---|
| 1 | M184C | N17C | A83C | K237C |
| 2 | M184C | N17C | S90C | S239C |
| 3 | M184C | N17C | V94C | E287C |
| 4 | V42C | T19C | A83C | K237C |
| 5 | V42C | T19C | S90C | S239C |
| 6 | V42C | T19C | V94C | E287C |

Transmembrane Protein Pore

One of the moieties is preferably a transmembrane protein pore. A transmembrane protein pore is a polypeptide or a collection of polypeptides that permits ions driven by an applied potential to flow from one side of a membrane to the other side of the membrane. The pore preferably permits nucleotides to flow from one side of a membrane to the other along the applied potential. The pore preferably allows a nucleic acid, such as DNA or RNA, to be pushed or pulled through the pore.

The pore may be a monomer or an oligomer. The pore is preferably made up of several repeating subunits, such as 6, 7 or 8 subunits. The pore is more preferably a heptameric pore. The pore typically comprises a barrel or channel through which the ions may flow. The subunits of the pore typically surround a central axis and contribute strands to a transmembrane β barrel or channel or a transmembrane α-helix bundle or channel.

The barrel or channel of the pore typically comprises amino acids that facilitate interaction with nucleotides or nucleic acids. These amino acids are preferably located near a constriction of the barrel or channel. The pore typically comprises one or more positively charged amino acids, such as arginine, lysine or histidine. These amino acids typically facilitate the interaction between the pore and nucleotides or nucleic. The nucleotide detection can be facilitated with an adaptor. This is discussed in more detail below.

Pores for use in accordance with the invention can be β-barrel pores, α-helix bundle pores or solid state pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin A (MspA), outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA.

The moiety may be a pore itself. Alternatively, if the pore is an oligomer, the moiety may be a pore subunit. The moiety may be isolated, substantially isolated, purified or substantially purified as described above.

The pore or subunit is preferably derived from α-hemolysin (α-HL). The wild type α-HL pore is formed of seven identical monomers or subunits (i.e. it is heptameric). The sequence of one wild type monomer or subunit of α-hemolysin is shown in SEQ ID NO: 2. The moiety preferably comprises the sequence shown in SEQ ID NO: 2 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 2 form loop regions. Residues 113 and 147 of SEQ ID NO: 2 form part of a constriction of the barrel or channel of α-HL. The nucleic acid binding protein is preferably attached to one or more of amino acids 8, 9, 17, 18, 19, 44, 45, 50 and 51 of SEQ ID NO: 2.

A variant of SEQ ID NO: 2 is a subunit that has an amino acid sequence which varies from that of SEQ ID NO: 2 and which retains its pore forming ability. The ability of a variant to form a pore can be assayed using any method known in the art. For instance, the variant may be inserted into a membrane along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

The variant may include modifications that facilitate covalent attachment to or interaction with the nucleic acid binding protein. The variant preferably comprises one or more reactive cysteine residues that facilitate attachment to the nucleic acid binding protein. For instance, the variant may include a cysteine at one or more of positions 8, 9, 17, 18, 19, 44, 45, 50, 51, 237, 239 and 287 and/or on the amino or carboxy terminus of SEQ ID NO: 2. Preferred variants comprise a substitution of the residue at position 8, 9, 17, 237, 239 and 287 of SEQ ID NO: 2 with cysteine (K8C, T9C, N17C, K237C, S239C or E287C).

The variant may also include modifications that facilitate any interaction with nucleotides or facilitate orientation of a molecular adaptor as discussed below. The variant may also contain modifications that facilitate covalent attachment of a molecular adaptor.

In particular, the variant preferably has a glutamine at position 139 of SEQ ID NO: 2. The variant preferably has a cysteine at position 119, 121 or 135 of SEQ ID NO: 2. SEQ ID NO: 4 shows the sequence of SEQ ID NO: 2 except that it has an cysteine at position 135 (L135C) and a glutamine at position 139 (N139Q). SEQ ID NO: 4 or a variant thereof may be used to form a pore in accordance with the invention. The variant may have an arginine at position 113 of SEQ ID NO: 2.

The variant may be a naturally occurring variant which is expressed naturally by an organism, for instance by a *Staphylococcus* bacterium, or expressed recombinantly by a bacterium such as *Escherichia coli*. Variants also include non-naturally occurring variants produced by recombinant technology. Over the entire length of the amino acid sequence of SEQ ID NO: 2 or 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 or 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be measured as described above.

Amino acid substitutions may be made to the amino acid sequence of SEQ ID NO: 2 or 4 in addition to those discussed above, for example up to 1, 2, 3, 4, 5, 10, 20 or 30 substitutions. Conservative substitutions may be made, for example, according to Table 1 above.

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may fragments of SEQ ID NO: 2 or 4. Such fragments retain pore forming activity. Fragments may be at least 50, 100, 200 or 250 amino acids in length. A fragment preferably comprises the pore forming domain of SEQ ID NO: 2 or 4. Fragments typically include residues 119, 121, 135. 113 and 139 of SEQ ID NO: 2 or 4.

One or more amino acids may be alternatively or additionally added to the polypeptides described above. An extension may be provided at the amino terminus or carboxy terminus of the amino acid sequence of SEQ ID NO: 2 or 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 2 or 4 is a subunit that has an amino acid sequence which varies from that of SEQ ID NO: 2 or 4 and which retains its ability to form a pore. A variant typically contains the regions of SEQ ID NO: 2 or 4 that are responsible for pore formation. The pore forming ability of α-HL, which contains β-barrel, is provided by β-strands in each subunit. A variant of SEQ ID NO: 2 or 4 typically comprises the regions in SEQ ID NO: 2 that form β-strands. The amino acids of SEQ ID NO: 2 or 4 that form β-strands are discussed above. One or more modifications can be made to the regions of SEQ ID NO: 2 or 4 that form β-strands as long as the resulting variant retains its ability to form a pore. Specific modifications that can be made to the β-strand regions of SEQ ID NO: 2 or 4 are discussed above.

A variant of SEQ ID NO: 2 or 4 preferably includes one or more modifications, such as substitutions, additions or deletions, within its α-helices and/or loop regions. Amino acids that form α-helices and loops are discussed above.

The variant may be modified for example by the addition of histidine or aspartic acid residues to assist its identification or purification or by the addition of a signal sequence to promote their secretion from a cell where the polypeptide does not naturally contain such a sequence.

Variants may also comprise any of the non-specific modifications discussed above for the nucleic acid binding protein. Subunits or pores can be made as discussed above.

Linkers and Groups

The two or more moieties have at least one linker and at least one group as defined above covalently attached thereto. Methods for attaching linkers and groups to moieties are well-known in the art. The linkers and groups are preferably chemically fused to the moiety. Suitable methods include, but are not limited to, primary amine/carboxylic acid coupling, reaction between thiols, reaction between non-natural amino acids and cysteine linkage.

The method of the invention may further comprise the step of attaching the at least one linker and/or the at least one group to each moiety.

The first moiety is preferably attached to the second moiety using linkers at one or more positions, for example at two, three or four positions. The position of attachment of each linker to its relevant moiety may be designed to constrain the relative mobility of the moieties. The number of positions at which the moieties are linked will have an effect on the rigidity of the final complex.

The linkers and/or groups may be attached to one or more reactive groups on the moiety, such as cysteine residues, reactive lysine residues or non-natural amino acids. Preferably, the linkers and/or groups are attached to one or more accessible cysteine residues in the moiety. Typically the linkers and/or groups are attached to the moiety via a disulphide bridge from one cysteine residue to another.

The linkers are high affinity hybridization linkers. They comprise at least one hybridizable region and preferably comprise at least one group capable of forming a covalent bond. Particularly preferred linkers which are effective at low concentrations, for example at nanomolar affinity. The length, flexibility and hydrophilicity of linkers are typically designed such that they do not to disturb the functions of the moieties to be linked. An advantage of using hybridization linkers is that the formation of unwanted homodimers of the moieties is minimized.

A hybridizable region is a region that is capable of undergoing hybridization with a hybridizable region in another linker. The hybridizable region preferably comprises a nucleic acid. The nucleic acid hybridization linkers can comprise any of the nucleic acids discussed above. For instance, they may comprise deoxyribonucleic acid (DNA), ribonucleic acid (RNA) or any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The nucleic acids that allow two linkers to hybridize may the same or different. Most preferably the linkers comprise DNA. Typically, when respective linkers comprise DNA, at least one linker must comprise single-stranded DNA. Prefereably, both linkers comprise single-stranded DNA.

Hybridization may be between two or more linkers, preferably between two or three linkers. In the case where three linkers are used, they form a triplex. The linkers may hybridize in a variety of conformations, for example in a "head to head" conformation or a "head to tail" conformation. In the "head to head" conformation, the linkers align so that the moieties are adjacent at the same end of the hybridized linkers. In the "head to tail" conformation, the linkers align so the moieties are at opposite ends of the hybridized linkers. The linkers may have any suitable three-dimensional conformation. Typically, a linker is linear, but it can also be triangular or shaped in another geometrical confirmation.

Preferred nucleic acid hybridization linkers correspond to the first 15, 25 or 35 nucleotides from the 5' end of SEQ ID NO: 57. The linker preferably also has TT at the 3' end to provide extra flexibility. At the 3' end, the linkers have a group, such as maleimide or Thiol, which allows the linker to be attached to the moiety. Maleimide or Thiol modified oligonucleotides can be obtained commercially, for instance from ATDBio. More preferred linkers are shown in SEQ ID NOs: 58, 59 and 60. Complementary linkers are shown in SEQ ID NOs: 61, 62 and 63. SEQ ID NO: 58, 59 or 60 may be attached to one of the moieties and the complementary linker (SEQ ID NO: 61, 62 or 63 respectively) is attached to the other moiety. The moieties can then be linked by hybridizing the linkers.

The stability of the hybridization depends on the melting temperature of the hybridizing linkers. Depending on the application and the required stability, this can be optimized by changing the sequences of the linkers (e.g. changing the linkers to more GC rich will increase their melting temperature and hence the stability), the length of the linkers (i.e. increasing their length will increase the stability) or the reaction conditions (e.g. increasing their concentration will increase the stability).

For maximum stability of hybridization, it is desirable to have long hybridizing linkers with high melting temperatures, for example linkers more than 15 nucleotides in length, particularly 15 to 45 nucleotides in length, such as 15, 20, 25, 30, 35, 40 or 45 nucleotides in length. However, the use of long linkers increases the distance between the moieties. This may be disadvantageous because interaction between the moieties is disrupted or because proximity is required for the one moiety to detect a substrate which has been released from the other moiety. Increased distance may be advantageous as it may prevent aggregation or electrostatic interactions and may permit flexing. The disadvantages of the increased distance can be overcome by changing the orientation of the nucleic acid attachment. Most preferably, the linkers comprise a nucleic acid that is from 6 to 15 nucleotides in length, such as 6, 8 or 10 nucleotides long.

The first and second hybridizable regions preferably have an affinity of from 1 fM to 1 uM at concentrations of from 1 pM to 1 mM. The first and second hybridizable regions more preferably have an affinity of from 1 fM to 10 nM at concentrations of from 1 pM to 1 uM.

The first and second hybridizable regions most preferably have an affinity of from 1 pM to 100 pM at concentrations of from 100 pM to 10 nM.

A preferred sequence is shown in the SEQ ID NO 64. The 3' end of this linker can be attached to a cysteine residue on the surface. The linker preferably also has TTTTT at the 3' end to provide extra flexibility. 5' end of SEQ ID NO 65 can then be attached to the nucleic acid binding protein. In this example, 3' end of the SEQ ID NO 64 is complementary to a stretch of sequence at the 5' end of the SEQ ID NO 65.

Once the linkers are hybridized to each other, they melt (fall apart) under certain conditions (for example, at high temperatures or lower salt conditions) unless there is a permanent bond between the two linkers. To form a permanent bond, the moieties are modified such they react with one another once they have hybridized. Each moiety has covalently attached thereto a group capable of forming a covalent bond with a group in another moiety. As discussed above, the group is preferably attached to the moiety via the hybridization linker. A pair of moieties can be linked by one or more covalent bonds, for example one, two or three, covalent bonds.

Typically the bond will be a simple disulfide bond between the two moieties. The moieties or hybridization linkers can also be modified to incorporate thiol groups at one or more, such as two, positions. Depending on the application and preferences, thiols groups can be incorporated into the linkers either internally or terminally.

The moieties or hybridization linkers can also be modified to include one or more, such as two, iodoacetamide groups. Again, the iodoacetamide groups can be incorporated into the linkers either internally or terminally. A moiety or a hybridization linker with one or more iodoactamide groups can be covalently linked to thiols on the complementary moiety or hybridization linker.

The moieties or hybridization linkers can also be modified with alkene groups. If incorporated into the hybridization linkers, the alkene groups can be internal or terminal. One or more alkene groups in preferred positions can be subjected to olefin metathesis to make a covalent bond between the alkenes in the moieties or hybridization linkers.

If necessary, a small linker can be added between the moiety or hybridization linker and the reactive groups, such as thiol groups, iodoacetamide groups and alkene groups, to obtain the proper distances necessary to make an efficient covalent bond between the moieties or hybridization linkers.

In a preferred embodiment, the covalent bond between the moieties or hybridization linkers can be made using the click chemistry. Click chemistry is a term first introduced by Kolb et al. in 2001 to describe an expanding set of powerful, selective, and modular building blocks that work reliably in both small- and large-scale applications (Kolb H C, Finn, M G, Sharpless K B, Click chemistry: diverse chemical function from a few good reactions, Angew. Chem. Int. Ed. 40 (2001) 2004-2021). They have defined the set of stringent criteria for click chemistry as follows: "The reaction must be modular, wide in scope, give very high yields, generate only inoffensive byproducts that can be removed by nonchromatographic methods, and be stereospecific (but not necessarily enantioselective). The required process characteristics include simple reaction conditions (ideally, the process should be insensitive to oxygen and water), readily available starting materials and reagents, the use of no solvent or a solvent that is benign (such as water) or easily removed, and simple product isolation. Purification if required must be by nonchromatographic methods, such as crystallization or distillation, and the product must be stable under physiological conditions".

Suitable example of click chemistry include, but are not limited to, the following:
(a) copper-free variant of the 1,3 dipolar cycloaddition reaction, where an azide reacts with an alkyne under strain, for example in a cyclooctane ring;
(b) the reaction of an oxygen nucleophile on one linker with an epoxide or aziridine reactive moiety on the other; and
(c) the Staudinger ligation, where the alkyne moiety can be replaced by an aryl phosphine, resulting in a specific reaction with the azide to give an amide bond.

Preferably the click chemistry reaction is the Cu (I) catalysed 1,3 dipolar cycloaddition reaction between an alkyne and an azide. In a preferred embodiment, the first group is an azide group and the second group is an alkyne group. Nucleic acid bases have already been synthesized incorporating azide and alkyne groups in preferred positions (for example Kocalka P, El-Sagheer A H, Brown T, Rapid and efficient DNA strand cross-linking by click chemistry, Chembiochem. 2008. 9(8): 1280-5). Alkyne groups are available commercially from Berry Associates (Michigan, USA) and azide groups are synthesized by ATDBio.

If nucleotides within the linkers' nucleic acid acid regions are modified to include groups that can form covalent bonds, the modified nucleotides are preferably offset from one another by one nucleotide in order to achieve the link. This follows the published work of Tom Brown (Kocalka et al. (2008) ChemBiochem 9 8 1280-1285).

In a preferred embodiment, a single azide group (SEQ ID NO 66) or more such as two (SEQ ID NO 67) can be incorporated into uracil bases at specific places in a 15 base deoxyribonucleic acid sequence. The cysteine residues on a moiety can then be modified with these azide hybridization linkers using the thiol group at the 5' end (SEQ ID NO 66 and 67). Alkyne groups can also be incorporated into uracil bases at preferred positions in sequences complementary to the SEQ ID NO 66 and 67 (SEQ ID NO 68 and 69 respectively). These sequences can be attached to the cysteines in one of the moieties. Using DNA hybridization followed by 'click chemistry' between the azide and alkyne groups, hybridization linkers can be covalently cross-linked. If the distance between the moieties has been modulated by changing the length of the hybridization linkers, the position of the azide and alkyne modified bases then needs to be changed accordingly.

In a preferred embodiment 6 mer (SEQ ID NO 70), 8 mer (SEQ ID NO 71) or 10 mer (SEQ ID NO 72) DNA in which two uracil bases are modified with azide groups can be attach to the cysteines of the moiety. Complementary sequences of 6 mer (SEQ ID NO 73), 8 mer (SEQ ID NO 74) or 10 mer (SEQ ID NO 75) DNA in which two uracil bases are modified with alkyne groups can be attached to the cysteines of a moiety such as a DNA binding protein. Using these hybridization linkers will bring the moieties closer to each other than with other preferred hybridization linkers of the invention, such as SEQ ID NO 67 and 69. Incorporation of azide and alkyne groups into uracil base units of DNA has been developed by ATDBio.

Other preferred groups for use in the invention are shown in the following Table 3.

TABLE 3

Some preferred groups capable of forming covalent bonds

| Name | Reacts with | Structure |
|---|---|---|
| 1,4-Bis[3-(2-pyridyldithio)propionamido]butane | Thiols | 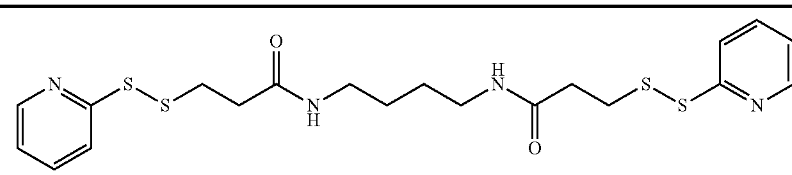 |
| 1,11-bis-Maleimidotriethyleneglycol | Thiols | 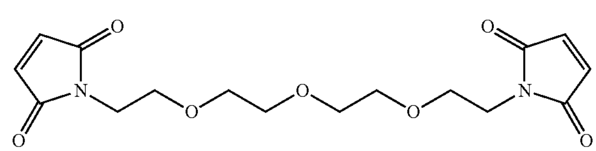 [SMILES: O=C1C=CC(=O)N1CCOCCOCCOCCN1C(=O)C=CC1=O] |
| 3,3'-Dithiodipropionic acid di(N-hydroxysuccinimide ester) | Primary amines | 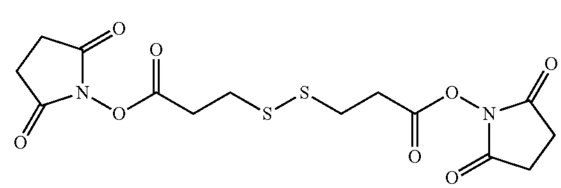 [SMILES: O=C(CCSSCCC(=O)ON1C(=O)CCC1=O)ON1C(=O)CCC1=O] |
| Ethylene glycol-bis(succinic acid N-hydroxysuccinimide ester) | Primary amines | 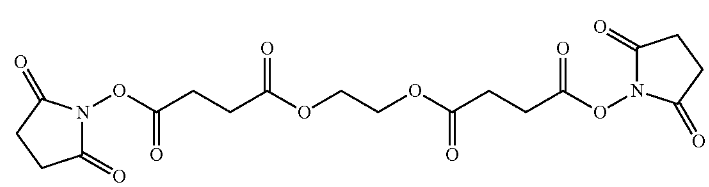 [SMILES: O=C(CCC(=O)ON1C(=O)CCC1=O)OCCOC(=O)CCC(=O)ON1C(=O)CCC1=O] |

TABLE 3-continued

Some preferred groups capable of forming covalent bonds

| Name | Reacts with | Structure |
| --- | --- | --- |
| 4,4'-Diisothiocyanatostilbene-2,2'-disulfonic acid disodium salt | Primary amines | 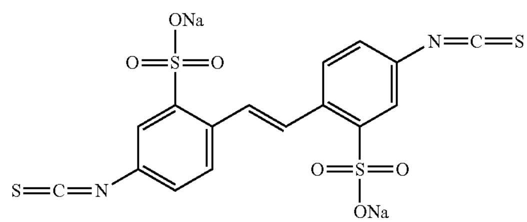 |
| Bis[2-(4-azidosalicylamido)ethyl] disulfide | Photo-activated, non-specific | 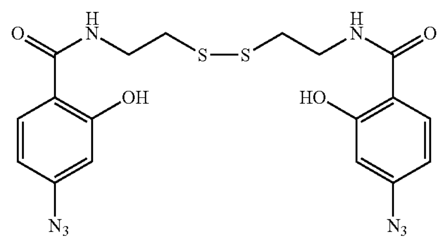 [SMILES: [N-]=[N+]=Nc1ccc(C(=O)NCCSSCCNC(=O)c2ccc(N=[N+]=[N-])cc2O)c(O)c1] |
| 3-(2-Pyridyldithio)propionic acid N-hydroxysuccinimide ester | Thiols, primary amines | 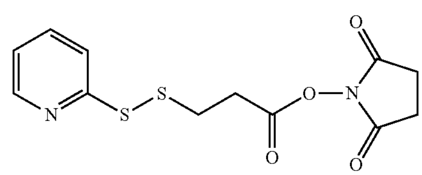 [SMILES: O=C(CCSSc1ccccn1)ON1C(=O)CCC1=O] |
| 4-Maleimidobutyric acid N-hydroxysuccinimide ester | Thiols, primary amines | 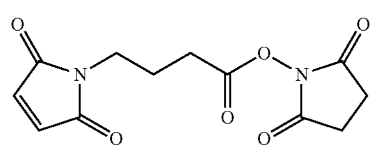 [SMILES: O=C(CCCN1C(=O)C=CC1=O)ON1C(=O)CCC1=O] |
| Iodoacetic acid N-hydroxysuccinimide ester | Thiols, primary amines | 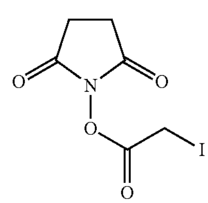 [SMILES: O=C(CI)ON1C(=O)CCC1=O] |
| S-Acetylthioglycolic acid N-hydroxysuccinimide ester | Thiols, primary amines | 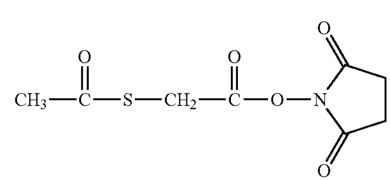 |
| Azide-PEG-maleimide | Thiols, alkyne | n = 5, 10 |

TABLE 3-continued

Some preferred groups capable of forming covalent bonds

| Name | Reacts with | Structure |
|---|---|---|
| Alkyne-PEG-maleimide | Thiols, azide | (maleimide)-CH$_2$CH$_2$-C(O)-NH-CH$_2$CH$_2$-(OCH$_2$CH$_2$)$_n$-O-CH$_2$CH$_2$-NH-C(O)-CH$_2$CH$_2$-C≡CH; n = 6, 10 |

Conditions

The moieties are first contacted under conditions that allow the first and second hybridizable regions to hybridize and link the moieties. Conditions that permit the hybridization are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridization can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridization can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridization can be carried out under high stringency conditions, for example in the presence of a buffered solution of 50% formamide, 1 M NaCl, 1% SDS at 37° C., followed by a wash in 0.1× (0.0165 M Na+) SSC at 60° C. Preferred conditions are those described in Example 1.

The linked moieties are then exposed to conditions that allow the formation of a covalent bond between the first and second groups. These conditions are of course dependent on the groups used. The reaction is preferably carried out at less than ph 7.0. Preferred conditions are those described in Example 1.

If one or more of the moieties are enzymes, such as nucleic acid binding proteins, the activity of the enzyme is preferably inhibited during the coupling and linking reactions. Magnesium-dependent enzymes, such as Exonuclease I, may be inhibited by EDTA or by CaCl$_2$ (Lehman (1960) J. Biol. Chem. 235 5 1479-1487 and internal data).

Preferred Combinations of Moieties

In a preferred embodiment, the first moiety is a protein and the second moiety is a reporter group. Suitable reporter groups include, but are not limited to, optical or fluorescent labels, steric tags, increases to mass, changes to charge, spin labels, radiolabels, magnetic groups and any combination thereof.

In another preferred embodiment, the first moiety is a protein and the second moiety is an affinity tag. Examples of affinity tags are well-known in the art. Suitable affinity tags include, but are not limited to, His-NTA, FLAG-Antibody-M2, myc, STrEP-streptavidin, NANO-streptavidin and biotin-avidin.

In another preferred embodiment, the first moiety is a protein and the second moiety is a support. Examples of supports are well-known in the art. Suitable supports include, but are not limited to, The support may be, but is not limited to metal surfaces, polymer beads, magnetic beads, glass, modified glass and silica gels.

In a preferred embodiment, the first moiety comprises exonuclease I from *E. coli* (SEQ ID NO: 6) or a variant thereof having at least one native accessible cysteine residue and the second moiety comprises α-HL (SEQ ID NO: 2) or a variant thereof. In a more preferred embodiment, the first moiety comprises exonuclease I from *E. coli* (SEQ ID NO: 6) or a variant thereof having all its native accessible cysteine residues removed and the second moiety comprises α-HL (SEQ ID NO: 2) or a variant thereof. In a more preferred embodiment, the first moiety comprises exonuclease I from *E. coli* (SEQ ID NO: 6) or a variant thereof having only the native cysteine residues at position 144 and/or 330 and the second moiety comprises α-HL (SEQ ID NO: 2) or a variant thereof. In a more preferred embodiment, the first moiety comprises exonuclease I from *E. coli* (SEQ ID NO: 6) or a variant thereof having all its native accessible cysteine residues removed and A83C and the second moiety comprises α-HL (SEQ ID NO: 2) or a variant thereof having E287C.

In a preferred embodiment, the first moiety comprises exonuclease I from *E. coli* (SEQ ID NO: 6) or a variant thereof having at least one native accessible cysteine residue removed and the second moiety comprises α-HL or a variant thereof having L135C and N139Q (e.g. SEQ ID NO: 4). In a more preferred embodiment, the first moiety comprises exonuclease I from *E. coli* (SEQ ID NO: 6) or a variant thereof having all its native accessible cysteine residues removed and the second moiety comprises α-HL or a variant thereof having L135C and N139Q (e.g. SEQ ID NO: 4). In a more preferred embodiment, the first moiety comprises exonuclease I from *E. coli* (SEQ ID NO: 6) or a variant thereof having only the native cysteine residues at position 144 and/or 330 and the second moiety comprises α-HL or a variant thereof having L135C and N139Q (e.g. SEQ ID NO: 4). In a more preferred embodiment, the first moiety comprises exonuclease I from *E. coli* (SEQ ID NO: 6) or a variant thereof having all its native accessible cysteine residues removed and A83C and the second moiety comprises α-HL or a variant thereof having L135C, N139Q and E287C.

Products

The invention also provides first and second moieties coupled using a method of the invention and a first moiety coupled to a second moiety using first and second linkers as defined above. The invention further provides a pair of first and second linkers as defined above. The linkers preferably comprise the groups capable of forming covalent bonds. Any of the embodiments described above with reference to the methods of the invention are equally applicable to the products of the invention.

The following Examples illustrate the invention:

1. Example 1

1.1 Materials and Methods

In this manifestation, an azide functional group and an alkyne functional group react with one another in the presence of a copper (I) catalyst to form a triazole ring, in the copper-catalysed alkyne azide cycloaddition reaction (CuAAC).

Figure 11:
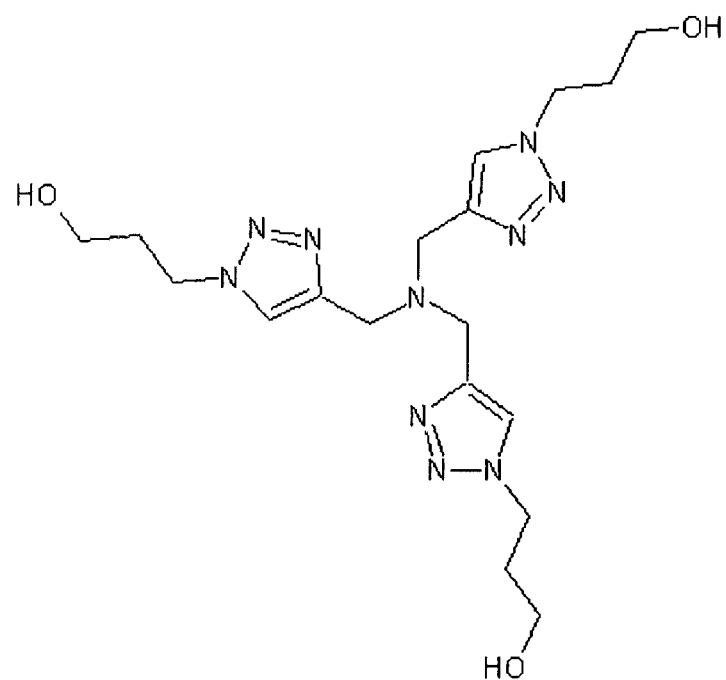
FIG. 11 shows the copper (I) binding ligand used in the Examples.

Copper (II) sulphate, sodium ascorbate, MOPS free acid, sodium phosphate, sodium chloride, calcium chloride, and EDTA were obtained at the highest grade available from standard laboratory suppliers, eg Sigma and Fisher. The copper (I) binding ligand (shown in FIG. 11).

Oligonucleotides with thiol end groups, or with internal azide or alkyne groups were from AtdBio (Southampton, UK); unmodified oligonucleotides were from AtdBio, or IDTDNA(Leuven, Belgium). The sequences of the oligonucleotides are shown in SEQ ID NOs: 64 to 78. In all cases of complementary oligonucleotides, the modified bases are offset from one another by one base in order to achieve the link.

1.2 Hybridization

When hybridizing oligonucleotides, the hybridization was carried out by incubating the oligonucleotides in buffer at 4° C. for at least 1 hour. For oligonucleotides 15 bases long, this buffer could be 100 mM MOPS pH6.8 or 100 mM sodium phosphate pH 7.0. For oligos shorter than this, 1000 mM NaCl was included. When enzyme inhibitors (10 mM EDTA or 20 mM $CaCl_2$) were added, this was in 100 mM phosphate pH 6.8 (for EDTA) or 100 mM MOPS pH6.8 (for either EDTA or $CaCl_2$).

1.3 Linking Reaction

The linking reaction was carried out after an overnight hybridization (for 15 bp duplexes and longer) or a 1 hour incubation (for 6-10 bp duplexes) at 4° C. The linking reaction was achieved by first pre-mixing copper (II) ion, ascorbate reducing agent, and a copper (I) binding ligand. The three components were mixed at the appropriate concentrations to achieve the final conditions. For instance, if the final required conditions were 1 mM copper, 2 mM ascorbate, 1 mM ligand in 100 µl reaction volume, equal volumes of 100 mM copper sulphate (in water), 200 mM sodium ascorbate (in a buffer at pH<7.0), and 100 mM ligand (in water) were mixed in the order specified, then 3 µl of the resulting mixture were added to the 100 µl reaction. After this addition, the reaction was left at 4° C. in the dark for at least 60 minutes.

| Oligos linked | Length of duplex | Link conditions/ [$Cu^I$], [ascorbate], [ligand], buffer | Link? | Confirmation |
|---|---|---|---|---|
| 76 + 77 | 15 bp | 5 µM, 10 µM, 7 µM, 1 | No | Gel |
| 76 + 77 | 15 bp | 0.5 mM, 1 mM, 0.5 mM, 1 | Yes | Gel |
| 66 + 68 (1 link) | 15 bp | 1 mM, 2 mM, 1 mM, 2 | Yes | Gel, $T_m$ |
| 67 + 69 (2 links) | 15 bp | 1 mM, 2 mM, 1 mM, 2 | Yes | Gel, $T_m$ |
| 70 + 73 | 6 bp | 1 mM, 2 mM, 1 mM, 3 | No | |
| 71 + 74 | 8 bp | 1 mM, 2 mM, 1 mM, 3 | Yes | Gel, $T_m$ |
| 72 + 75 | 10 bp | 1 mM, 2 mM, 1 mM, 3 | Yes | Gel, $T_m$ |

Buffer 1 = 100 mM phosphate, 500 mM NaCl pH 7.0
Buffer 2 = 100 mM phosphate pH 6.8
Buffer 3 = 100 mM MOPS, 1000 mM NaCl, 20 mM $CaCl_2$ pH 6.8

1.4 Attachment Reaction

To attach an oligonucleotide to a protein, the oligonucleotides must first be activated. This procedure changes the chemical nature of the supplied oligonucleotides from one that is inert to the protein to one that can react with the protein. This process makes no difference to the linking reaction.

When required, oligonucleotides were attached to proteins through disulphide bonds. This was achieved by incubating a 5× excess of activated oligonucleotide with freshly reduced protein for 1 hour at 37° C. (for exonuclease), or overnight at room temperature (for nanopore). In all cases, oligonucleotides containing the azide base(s) were attached to the nanopore (through E287C on one of the monomers), and the oligonucleotides containing the alkyne base(s) were attached to the exonuclease (through A83C). Unreacted DNA was removed by purification on Strepavidin affinity beads.

1.5 Coupling of Proteins

Purified modified proteins were incubated together under conditions designed to promote hybridization between the oligonucleotides. For 15 base oligonucleotides and longer this buffer could be 100 mM MOPS pH6.8 or 100 mM sodium phosphate pH7.0. When enzyme inhibitors were required, 20 mM $CaCl_2$ was supplemented in to 100 mM MOPS pH6.8. For 6-10 base oligos, the buffer was 100 mM MOPS, 1000 mM NaCl, 20 mM $CaCl_2$ pH6.8.

The linking reaction was carried out as described above, as these conditions have been shown to be compatible with enzyme activity.

| Protein 1 | Protein 2 | Duplex length | Link conditions/ [$Cu^I$], [ascorbate], [ligand], buffer | ONT colloquial name |
|---|---|---|---|---|
| Exo-SEQ 78 | Pore-SEQ 67 | 15 bp | 1 mM, 2 mM, 1 mM, 4 | PK V3 |
| Exo-SEQ 73 | Pore-SEQ 70 | 6 bp | 1 mM, 2 mM, 1 mM, 3 | TL |

Buffer 4 = 100 mM MOPS, 20 mM $CaCl_2$ pH 6.8

2. Example 2

2.1 Materials and Methods 2.1.1 Overview

One method of sequencing nucleic acids using stochastic sensing involves the use of an exonuclease attached to the α-HL pore. This can be done by introducing a chemical linkage between the two proteins. The chemical linkage joins one cysteine on the exonuclease to one cysteine on the hemolysin, either directly (a disulphide bond), or via a linker molecule between the two cysteine residues.

In order to introduce the chemical linkage in a controlled and directed approach it was necessary to replace 5 naturally occurring cysteine residues found within Exonuclease I with other residues. An additional mutation would then be made in order to introduce the cysteine residue attachment point. Computer modeling was used to identify suitable attachment positions (see below).

2.1.2 Modelling Exo I CYS Knockout Mutations

Molecular modelling has been used in an attempt to predict which mutations of the 5 wild type cysteine residues of *E. coli* Exo I are compatible with protein stability. To this end alchemical free energy perturbation simulations where performed for these mutations, allowing predictions to be made about their relative stability. These predictions were used to guide experimental work.

VMD in combination with NAMD was used in conjunction with the CHARMM27 forcefield to perform alchemical free energy perturbation calculations upon wild type CYS to XXX mutations of the *E. coli* Exo I protein structure (PDB accession code: 1ax [14]) were determined. The resulting lambda vs. deltaG curves were used to determine the free energy change upon mutation and if the calculations had converged.

2.1.3 Expressions and Purification

A codon optimised version of the Exonuclease I gene, scsB, from *Escherichia coli* (SEQ ID NOs: 5 and 6) was obtained from GenScript Corporation. Site directed mutagenesis of cysteine residues was performed by an adapted form of in vivo homologous recombination of PCR products (Jones, D. H. PCR mutagenesis and recombination in vivo. (1994) Genome Research, 3. pp 141-148). Plasmids containing the gene of interest were transformed into BL21 (DE3) pLysS (stratagene). Cultures containing 500 ml Terrific Broth in 2 liter baffled shake flasks supplemented with 100 μg/ml ampicillin and 20 μg/ml chloramphenical were inoculated with colonies from agar plates and grown to OD600=2 (approx 6 hours) before induction with 0.2 mM IPTG at reduced temperature (18° C.). Cells were harvested by centrifugation at 4K followed by lysis with bugbuster (Novagen) and benzonase (Merck). Cell debris was removed by centrifugation at 10K and the supernatant filtered before loading onto a His-Trap column (GE Healthcare). Eluted protein was further purified by gel filtration.

2.1.4 Enzyme Assay

Figure 6:
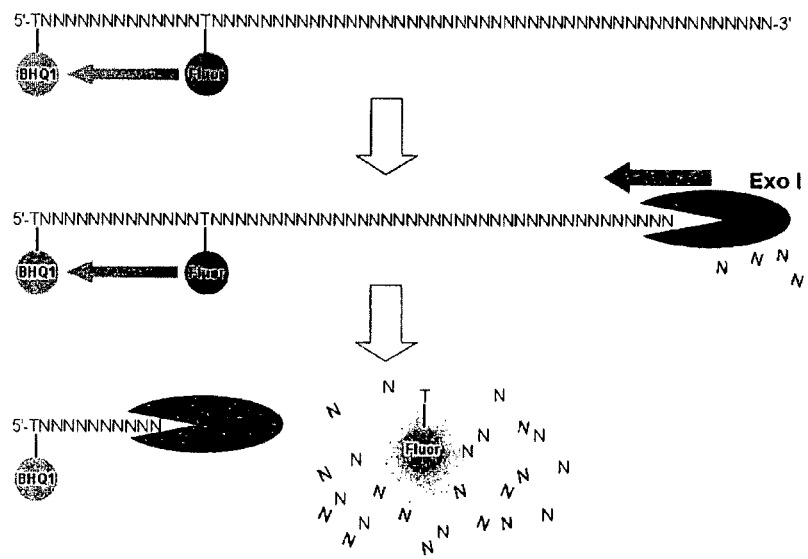
FIG. 6 shows a schematic representation of the Exonuclease I assay.

The Exonuclease I (Exo I) assay employs an oligodeoxynucleotide (DNA template) labelled with a fluorescein dye ("Fluor") on a dT at position 15, and a fluorescein quencher ("BHQ1") on dT at position 1. The template initially exists in a quenched state, with the fluorescein and quencher in close proximity. Upon the introduction of Exo I, the DNA template is digested in a processive manner from the 3'-end, eventually releasing dT-Fluor into solution and leading to a subsequent increase in fluorescence as the dye diffuses away from the quencher (FIG. 6).

Figure 7:
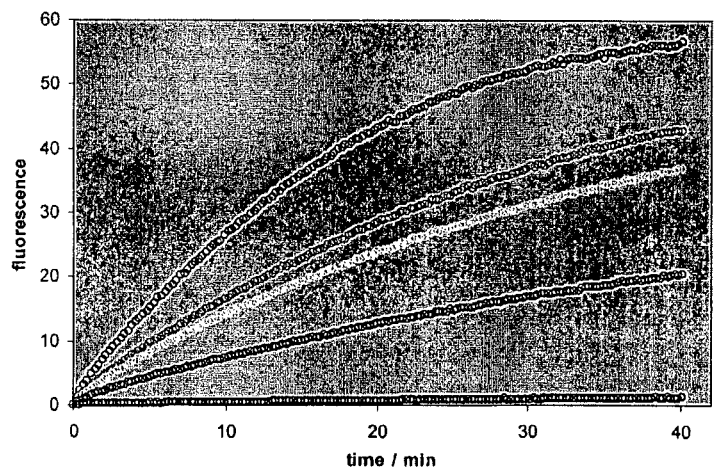
FIG. 7 shows an example of data from the Exonuclease I assay.

To conduct the assay, DNA template is transferred into a cuvette and placed in a Cary Eclipse fluorimeter to equilibrate at a desired temperature. Meanwhile, Exo I is equilibrated separately using a water bath and then added to the template-containing cuvette. The subsequent increase in fluorescence signal is monitored over time (see FIG. 7 for example data) with the initial rate of increase extracted. The end-point-fluorescence after the template has been fully digested is correlated with the initial amount of DNA template in order to convert the fluorescence-based rate to a molecular one.

2.2 Results 2.2.1 Modelling Exo I CYS Knockout Mutations

The results of modelling of mutations is summarized in the Tables below.

| Mutation | deltaG (vacuo) | deltaG (water) | Converged (vacuo) | Converged (water) |
|---|---|---|---|---|
| C51A | +3.4 | +3.2 | YES | YES |
| C51R | −239.2 | −251.2 | NO | NO |
| C51N | −69.5 | −66.8 | NO | NO |
| C51D | −67.7 | −82.6 | NO | NO |
| C51C | +0.9 | +0.9 | YES | YES |
| C51Q | −49.5 | −50.7 | NO | NO |
| C51E | −55.2 | −68.9 | NO | NO |
| C51G | −0.8 | −0.5 | YES | YES |
| C51H | −24.9 | −18.5 | YES | YES |
| C51I | +8.6 | +11.0 | YES | YES |
| C51L | −1.8 | −11.7 | YES | YES |
| C51K | −37.9 | −12.1 | YES | YES |
| C51M | −1.8 | −0.4 | YES | YES |
| C51F | +15.6 | +9.4 | YES | YES |
| C51S | +4.6 | +11.9 | YES | NO |
| C51T | −11.3 | −10.7 | YES | YES |
| C51W | +15.6 | +11.6 | YES | YES |
| C51Y | −9.3 | −12.3 | YES | YES |
| C51V | +3.4 | +4.2 | YES | YES |
| C98A | +0.4 | +4.2 | YES | YES |
| C98R | −203.4 | −231.0 | NO | NO |
| C98N | −79.3 | −76.1 | NO | NO |
| C98D | −111.5 | −113.7 | NO | NO |
| C98C | +0.0 | −0.3 | YES | YES |
| C98Q | −48.2 | −54.3 | NO | NO |
| C98E | −55.7 | −99.4 | NO | NO |
| C98G | +1.3 | −2.0 | YES | YES |
| C98H | −14.9 | −16.8 | YES | YES |
| C98I | +6.5 | +10.0 | YES | YES |
| C98L | −2.7 | −11.3 | YES | YES |
| C98K | +11.7 | −25.5 | YES | YES |
| C98M | +0.7 | +2.0 | YES | YES |
| C98F | +10.1 | +23.9 | YES | YES |
| C98S | +3.0 | +9.3 | YES | NO |
| C98T | −13.3 | −11.8 | YES | YES |
| C98W | +17.7 | +23.6 | YES | YES |
| C98Y | +9.9 | +2.2 | YES | YES |
| C98V | +2.0 | −0.3 | YES | YES |
| C144A | +1.2 | −0.9 | YES | YES |
| C144R | −218.0 | −243.8 | NO | NO |
| C144N | −64.9 | −73.5 | NO | NO |
| C144D | −70.6 | −111.9 | NO | NO |
| C144C | +0.4 | +0.0 | YES | YES |
| C144Q | −45.9 | −52.4 | NO | NO |
| C144E | −60.2 | −71.4 | NO | NO |
| C144G | −3.2 | −1.5 | YES | YES |
| C144H | −14.0 | −16.0 | YES | YES |
| C144I | +9.9 | +7.3 | YES | YES |
| C144L | −12.9 | −11.4 | YES | YES |
| C144K | −11.9 | −25.6 | YES | YES |
| C144M | −2.6 | −2.5 | YES | YES |
| C144F | +16.0 | +8.5 | YES | YES |
| C144S | +7.1 | +7.6 | YES | YES |
| C144T | −12.9 | −9.2 | YES | YES |
| C144W | +14.2 | +9.2 | YES | YES |
| C144Y | +5.8 | −7.4 | YES | YES |
| C144V | +0.4 | +0.5 | YES | YES |
| C306A | +3.4 | +1.1 | YES | YES |
| C306R | −207.6 | −245.2 | NO | NO |
| C306N | −67.8 | −77.1 | NO | NO |
| C306D | −125.2 | −106.6 | NO | NO |
| C306C | +2.5 | +0.0 | YES | YES |
| C306Q | −49.8 | −51.7 | NO | NO |
| C306E | −66.6 | −108.9 | NO | NO |
| C306G | −5.1 | −3.3 | YES | YES |
| C306H | −12.6 | −18.0 | YES | NO |
| C306I | +11.0 | +7.4 | YES | YES |
| C306L | −7.3 | −13.5 | YES | YES |
| C306K | −25.1 | −21.4 | YES | YES |
| C306M | +0.5 | −4.4 | YES | YES |

-continued

| Mutation | deltaG (vacuo) | deltaG (water) | Converged (vacuo) | Converged (water) |
|---|---|---|---|---|
| C306F | +10.7 | +2.5 | YES | YES |
| C306S | +2.7 | +5.8 | YES | YES |
| C306T | −15.5 | −12.9 | NO | YES |
| C306W | +15.5 | +13.6 | YES | YES |
| C306Y | −6.8 | −15.7 | YES | YES |
| C306V | +1.9 | +4.0 | YES | YES |
| C330A | +2.5 | +1.6 | YES | YES |
| C330R | −219.2 | −241.1 | NO | NO |
| C330N | −77.1 | −65.8 | NO | NO |
| C330D | −62.2 | −101.9 | NO | NO |
| C330C | +2.1 | −0.1 | YES | YES |
| C330Q | −47.0 | −49.8 | NO | NO |
| C330E | −36.9 | −66.2 | NO | NO |
| C330G | −1.1 | −0.2 | YES | YES |
| C330H | −13.1 | −19.0 | YES | YES |
| C330I | +7.0 | +2.6 | YES | YES |
| C330L | −10.5 | −10.9 | YES | YES |
| C330K | −31.8 | −26.4 | YES | NO |
| C330M | −2.9 | −4.6 | YES | YES |
| C330F | +8.3 | +12.2 | YES | YES |
| C330S | +5.1 | +4.7 | YES | YES |
| C330T | −12.5 | −14.8 | YES | YES |
| C330W | +5.8 | +14.6 | YES | YES |
| C330Y | −1.8 | −2.2 | YES | YES |
| C330V | +5.3 | +1.3 | YES | YES |

It is clear from the tables above that the obvious mutation (Cys to Ser) at each of these sites is not predicted to be energetically favourable (positive predicted deltaG). The mutations which are predicted to stabilise the protein vary significantly, as a consequence of their different local environments.

It should be noted that, although we have both activity and expression data, this does not directly relate to the delta G values in these tables. The delta G values can be related to thermodynamic data (such as that obtained from DSC), providing it is assumed that the mutations do not change the protein folding pathway significantly (which in many applications of alchemical FEP in the literature, has been found to be applicable). There is no direct relationship between expression and delta G of mutation or activity.

Comparison of the crystal structures of the Klenow fragment of DNA polymerase I and EcoExo I [14] suggest indicate that the residues involved in protein catalysis and metal binding are Asp15, Glu17, Asp108, Asp186 and His181.

Residue types other than Cys can also be chemically modified, including Asp[1,2], Glu[1,2], Lys[3,4,5], Arg[6,7,8], His [9,10], Tyr[11,12], Trp[11,12] and Met[13]. Therefore mutating these residues, in order to allow directed chemical modifications of Exo I allows us to remove competing chemical reactions.

Experimental work (see below) shows that many of these mutations result in proteins that retain their activity and in some cases appear to enhance activity, either as single mutations or as combinations of mutants. Comparison of the *E. coli* Exo I sequence with other related Exo I protein sequences, and the construction of homology models of these sequences suggests that many of these Cys residues are conserved both in sequence and in structure. This suggests that the properties of the Cys mutants of *E. coli* Exo I may be applicable to similar mutants of related Exo I enzymes.

A sequence alignment of all the Exo I enzymes in the Swissprot database shows that C51, C98, C144 and C306 are conserved.

2.2.2 Identification of 5 Cysteine Residues

Exonuclease I (SEQ ID NO: 6) contains 5 naturally occurring cysteine residues (FIG. 1). Some of the cysteine residues are conserved within other homologues of *E. coli* Exonuclease I (EcoExo I) (see below). None of the cysteine residues within Exonuclease I form internal disulphide bonds.

2.2.3 Removal of all 5 Cysteines by Mutation to Serine

The serine (Ser) amino acid is the most similar in structure to cysteine (Cys), with the S atom being replaced by an O. The most obvious mutation to make is therefore a Cys (C) to Ser (S). To test the activity of this mutant, all 5 cysteine residues were mutated to serine and protein expression was attempted.

Expression of ONLD0217 (Exo I C51S/C98S/C144S/C306S/C330S) resulted in reduced yields, poor expression and unstable protein. The protein was not able to be purified. This demonstrates that when all the Cys are replaced with Ser, the protein is not stable. Further investigation of the protein structure was required to engineer a cysteine free EcoExo I. This was guided in part by computer modeling.

2.2.4 Replacement of Individual Cysteines by Mutation to Serine

To identify cysteine positions that would tolerate substitution individual cysteine residues were replaced in turn with a serine residue.

Constructs ONLD0233 (C51S), ONLD0234 (C98S), ONLD0235 (C144S), ONLD0236 (C306S), ONLD0237 (C330S) were expressed. The mutant C98S expressed to sufficient levels, after a few attempts sufficient levels of C306S were also achieved. However expression levels of all the other position were much reduced.

Figure 2:
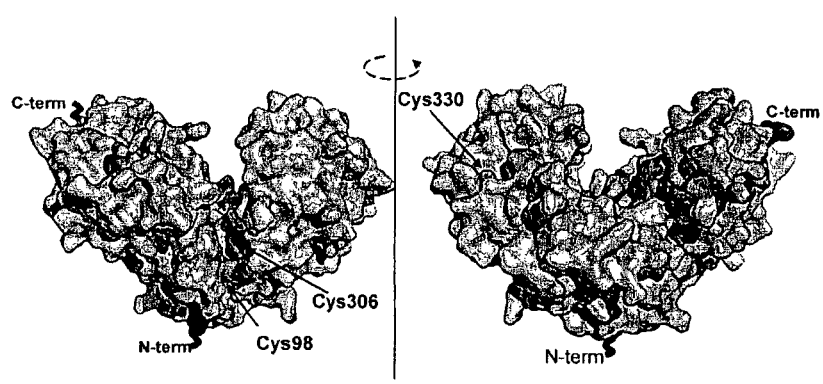
FIG. 2 shows a surface diagram of EcoExo I showing the position of accessible cysteines (obtained from crystal structure).

Alternative mutations were therefore considered to produce sufficient expression levels so that the mutants could be tested for exonuclease activity. The cysteines were grouped into highly accessible positions (C98, C306, C330; FIG. 2) and more buried residues (C51, C144).

2.2.5 Replacement of C306 and C330 with Alternatives to Serine

Replacement of cysteine residues at positions 306 and 330 were investigated by examination of the following mutants.

Exo I C306→D, M, N, S, T
Exo I C330→D, M, N, T, Y, H, L, M, Q

Expression levels of ONLD0335 (C306T) were highest. Other mutations that were tolerated in this position were S, D and N.

Expression levels of ONLD0342 (C330T) were highest. Other mutations that were tolerated in this position were H, Q and M and to a lesser extent D, N, L and Y.

2.2.6 Combining C98S with C3065 and C330T

In case double and triple mutations adversely affected each other the following combinations were investigated.

| ONLD Number | EcoExo I Mutant | Expression |
|---|---|---|
| ONLD0366 | C98S/C306S/C330T (SST) | High |
| ONLD0368 | C98S/C306T/C330T (STT) | High |
| ONLD0367 | C98S/C306T/C330H (STH) | Low |
| ONLD0364 | C98S/C306D/C330T (SDT) | Low |
| ONLD0365 | C98S/C306S/C330H (SSH) | Failed |
| ONLD0363 | C98S/C306D/C330H (SDH) | Failed |

The combination ONLD0366 gave highest expression followed by ONLD0368. The combinations ONLD0365 and ONLD0363 failed to express. Lower yields were obtained from ONLD0367, ONLD0364.

Figure 3:
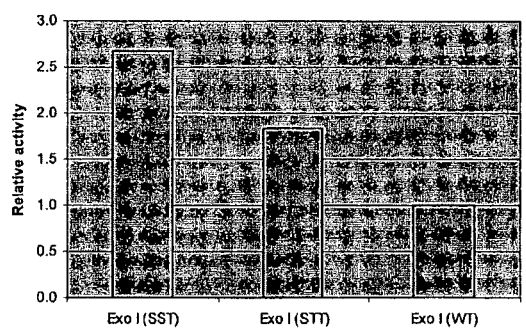
FIG. 3 shows the relative activity of Exo I mutants compared to the wild type.

Activity assays (see Methods) showed that the relative activity of the Exo I mutants was higher than the wild type (FIG. 3).

2.2.7 Introduction of Cysteine Attachment Points

Figure 4:
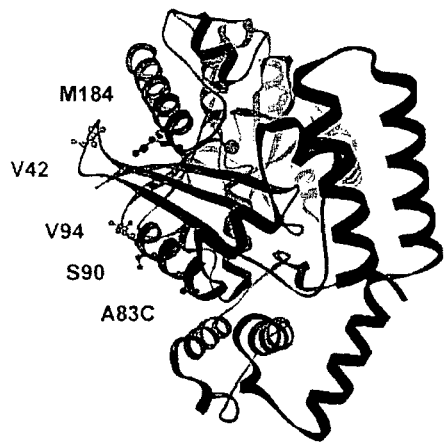
FIG. 4 shows a diagram of EcoExo I showing the positions at which a single cysteine could be introduced for coupling to a protein nanopore

Attachment points were designed to form a covalent bond from α-HL direct to the corresponding cysteine of Exonuclease I or via a linker. The attachment positions (V42C, A83C, S90C, V94C, M184C) predicted via modeling are shown in FIG. 4.

Introduction of the above cysteines to the mutant Exo I C98S, C306S, C330T gave the following constructs:

| ONLD Number | EcoExo I Mutant | Cysteine Position |
|---|---|---|
| ONLD0379 | C98S/C306S/C330T/M184C | 184 |
| ONLD0372 | C98S/C306S/C330T/V42C | 42 |
| ONLD0373 | C98S/C306S/C330T/S90C | 90 |
| ONLD0378 | C98S/C306S/C330T/A83C | 83 |
| ONLD0374 | C98S/C306S/C330T/V94C | 84 |

The activity of the cysteines was assessed by reacting with malemide-PEG which acts as a gel-shift reagent. The resultant gels showed that each protein had three reactive cysteines. This data showed that the cysteines at C144 and C51 were more accessible than previously assumed and were also reacting with the malemide-PEG. Further rounds of mutagenesis were carried out to replace C144 and C51 to ensure that the protein only react at one position.

2.2.8 Replacement of Residue C144 with Alternatives to Serine

Possible mutations were assessed from a total of 18 using molecular modeling (A, E, G, I, L, N, R, T, W, D, F, H, K, M, Q, S, V, Y). The six most stable mutants at residue 144 predicted from the modeling were made:

Exo I C98S, C306S, C330S, C144→A, G, L, T, H, M

From the 6 mutations tested (ONLD0403) Exo I C98S/C306S/C330T/C144M and (ONLD0404) Exo I C98S/C306S/C330T/C144T expressed well. Expression levels were reduced in the other mutants.

2.2.9 Replacement of Residue C51 with Alternatives to Serine

Possible mutations were assessed from a total of 17 using molecular modeling (A, D, E, F, G, H, I, K, L, M, N, R, S, T, V, W, Y). The eight most stable mutants at residue 51 predicted from the modeling were made:

Exo I C98S, C306S, C330S, C51→A, G, H, K, L, M, T, W

From the 8 mutations tested only (ONLD0393) Exo I C98S/C306S/C330T/C51A expressed.

2.2.10 Combination of 5 Cysteine Replacements and Addition of Attachment Point

The following combinations were assessed. These included all 5 cysteine replacements and addition of a cysteine attachment point. Attachment could also be made to a cysteine added to the N or C-termini.

| ONLD Number | EcoExo I Mutant | Expression |
|---|---|---|
| ONLD0416 | C51A/C98S/C144T/C306S/C330T/V42C | Excellent |
| ONLD0418 | C51A/C98S/C144T/C306S/C330T/M184C | Excellent |
| ONLD0415 | C51A/C98S/C144M/C306S/C330T/V42C | Good |
| ONLD0417 | C51A/C98S/C144M/C306S/C330T/M184C | Good |
| ONLD0413 | C51A/C98S/C144M/C306S/C330T/n-term C | Failed |
| ONLD0414 | C51A/C98S/C144T/C306S/C330T/n-term C | Failed |
| ONLD0425 | C51A/C98S/C144T/C306S/C330T/V94C | v. Poor/failed* |
| ONLD0422 | C51A/C98S/C144T/C306S/C330T/S90C | Poor |
| ONLD0421 | C51A/C98S/C144T/C306S/C330T/A83C | Good |

*ONLD0425 did not express well - not enough to measure the concentration but enough to just confirm activity.

Figure 5A:
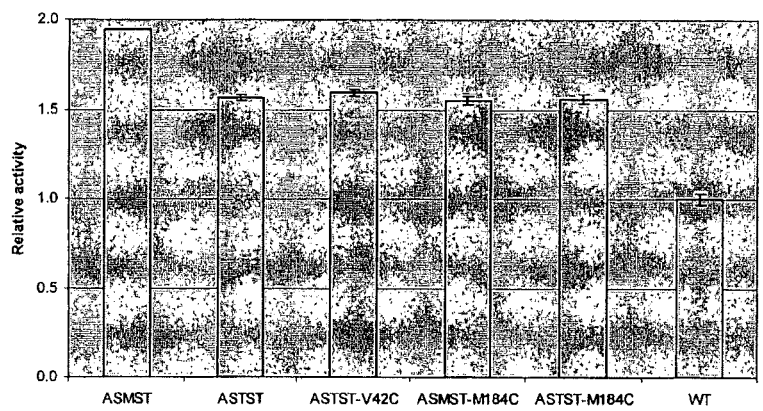
FIGS. 5a and 5b show the relative activity of Exo I mutants compared to the wild type.
Figure 5B:
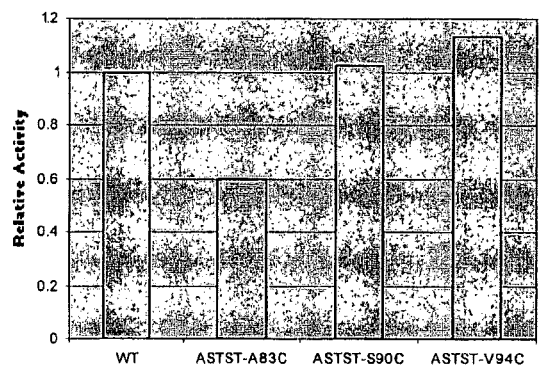

The two mutants with N-terminal cysteine residues (OND0413, ONLD0414) failed to express. All other combinations expressed and were active exonucleases. Combinations ONLD0415 and ONLD0417 expressed less well than ONLD0416 and ONLD0418. The activity results are shown in FIG. 5.

The following combinations were also assessed.

| | Position 98 and 306 | |
|---|---|---|
| ONLD Number | EcoExo I Mutant | Expression |
| ONLD0411 | C51A/C98S/C144T/C306S/C330T | High |
| ONLD0432 | C51A/C98T/C144T/C306S/C330T | High |
| ONLD0433 | C51A/C98T/C144T/C306T/C330T | High |

| | Position 98 | |
|---|---|---|
| ONLD Number | EcoExo I Mutant | Expression |
| ONLD0411 | C51A/C98S/C144T/C306S/C330T | Excellent |
| ONLD0432 | C51A/C98T/C144T/C306S/C330T | Excellent |
| ONLD0453 | C51A/C98G/C144T/C306S/C330T | Good |
| ONLD0454 | C51A/C98K/C144T/C306S/C330T | Good |
| ONLD0455 | C51A/C98L/C144T/C306S/C330T | Failed |
| ONLD0456 | C51A/C98V/C144T/C306S/C330T | Excellent |

| | Position 306 | |
|---|---|---|
| ONLD Number | EcoExo I Mutant | Expression |
| ONLD0433 | C51A/C98T/C144T/C306T/C330T | Good |
| ONLD0477 | C51A/C98T/C144T/C306M/C330T | Good |
| ONLD0478 | C51A/C98T/C144T/C306N/C330T | Good |
| ONLD0479 | C51A/C98T/C144T/C306D/C330T | Poor |
| ONLD0480 | C51A/C98T/C144T/C306A/C330T | Poor |

2.2.11 DSC Analysis of Proteins

Differential scanning calorimetry (DSC) is a technique that allows measurement of thermal transitions within a sample. Its primary use is measuring the thermal stability of a biomolecule as a transition mid-point. The transition mid-point is used as a marker of thermal stability.

The earliest mutant analysed with all 5 cysteines replaced (Exo-ASTST) was found to be quite unstable with a high loss of activity over time. The Tm was determined to be 35° C., compared to wildtype at 49° C.

Following further rounds of mutant screening the enzyme Exo-ATTTT was identified with a Tm of 40° C. and greatly improved stability over time. Other combinations eg Exo-ATTMT and Exo-AVTAT had a similar but not improved Tm of 40° C.

The mutant AVTMT was found to have slightly higher Tm, however was found more prone to aggregation under some conditions.

Addition of the preferred non-native cysteine (A83C) added for attachment purposes does not appear to have a detrimental effect on stability.

| Sample | ONLD | Tm (melting point) C. | | | | | | | | | |
|---|---|---|---|---|---|---|---|---|---|---|---|
| ASTST | ONLD0411 | 35.5 C. | 35.8 C. | | | | | | | | |
| ATTTT | ONLD0433 | 40.5 C. | 40.3 C. | 39.8 C. | 39.8 C. | 39.8 | 39.6 | 39.6 | 39.3 | 39.7 | 39.9 |
| WT | ONLD0267 | 49 | 48.9 | | | | | | | | |
| ATTST | ONLD0432 | 39.8 C. | 39.9 | 40 | 40.1 | | | | | | |
| CSCST | ONLD0366 | 41.7 | 41.8 | | | | | | | | |
| AVTST | ONLD0456 | | | 39.7 C. | 39.9 C. | | | | | | |
| AGTST | ONLD0453 | | | 36 C.* | 36 C.* | | | | | | |
| AKTST | ONLD0454 | | | nd | nd | | | | | | |
| ATTMT | ONLD0477 | | | | | 40.8 | 40.7 | | | | |
| ATTNT | ONLD0478 | | | | | 39.6 | 39.5 | | | | |
| ATTDT | ONLD0479 | | | | | 37.5* | 37.4* | | | | |
| ATTAT | ONLD0480 | | | | | 38.6* | 38.5* | | | | |
| AVTTT | ONLD0476 | | | | | | | 40.3 | 40.2 | | |
| AVTMT | ONLD0492 | | | | | | | 42.13 | 42.3 | | |
| AVTNT | ONLD0493 | | | | | | | 40.15 | 40.18 | | |
| AVTDT | ONLD0494 | | | | | | | 38.4 | 38.3 | | |
| AVTAT | ONLD0495 | | | | | | | 40.1 | 40.1 | | |
| NTTTT | ONLD0497 | | | | | | | | | x | x |
| NVTMT | ONLD0510 | | | | | | | | | 40.0 | 39.9 |
| NVTNT | ONLD0511 | | | | | | | | | 37.7 | 37.8 |
| NVTAD | ONLD0514 | | | | | | | | | nd | nd |
| NVTTT | ONLD0496 | | | | | | | | | 37.7 | 37.7 |
| ADTST | ONLD0491 | | | | | | | | | x | x |

DSC results

| Sample | ONLD | Tm Exp 1a | Tm Exp 1b |
|---|---|---|---|
| Exo-ATTTT-A83C-Strep-Strep | ONLD0540 | 40.68 | 40.94 |

2.2.12 Other mutations of Interest: C144I and C330I

C144 is adjacent to both the DNA binding site and the catalytic site of Exo-I. Residue C144 and C330 have not been mutated as much as other cysteine residues to find the best combination. Based upon the analysis of protein sequence and previous modelling work, models of the following 2 proteins (ATTTT and ATITI) were constructed.

Modeling work comparing ATTTT with ATITI suggest that T330 side chain causes little disruption of the protein secondary structure. T144 however is packed with the hydrophobic core which appears to be disrupted when the T144 side chain flips, causing significant disruption to the core. The ATITI model simulation does not show the same degree of disruption around T144.

2.2.13 Enzyme Activity

Figure 8:
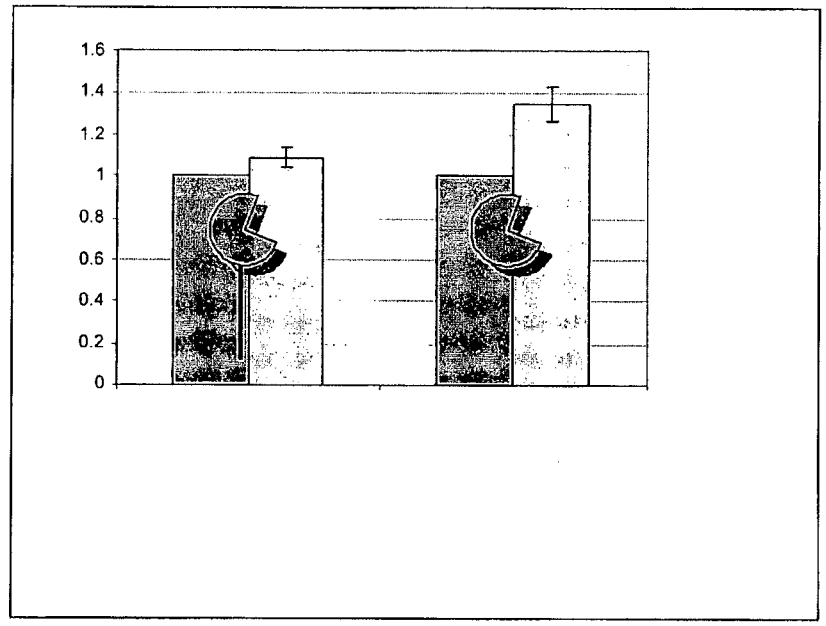
FIG. 8 shows that the attachment of a linker to Exo-ATTTT-A83C does not affect enzyme activity. The Y-axis is relative activity. The left-hand pair of columns is ONLP1403 and the right-hand pair of columns is ONLP1405. In each pair, the left-hand (darker) column is the enzyme with linker and the right-hand (lighter column) is enzyme without linker.
Figure 9:
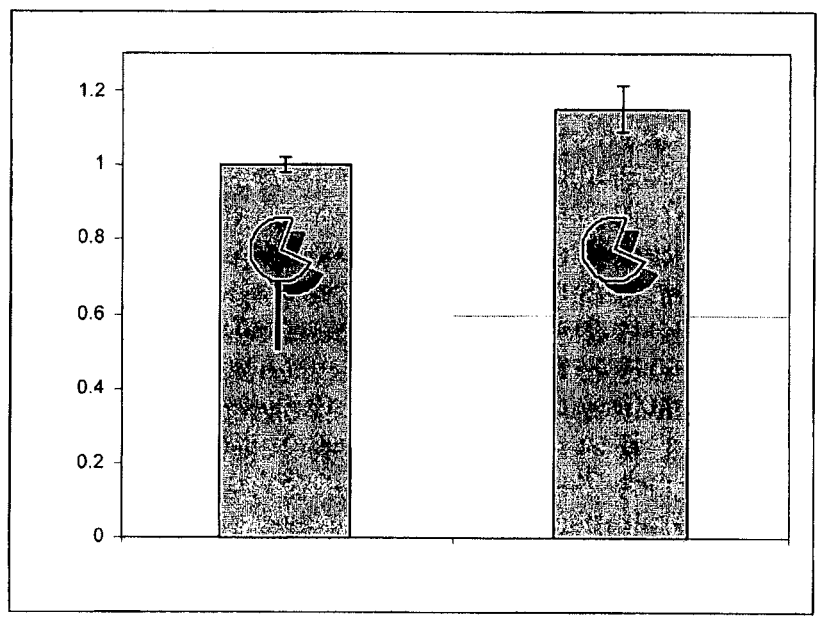
FIG. 9 shows that the attachment of PNA to Exo-ATTTT-A83C does not affect enzyme activity. The Y-axis is relative activity. The left-hand column is ONLP1498 and the right-hand column is ONLP1499.
Figure 10:
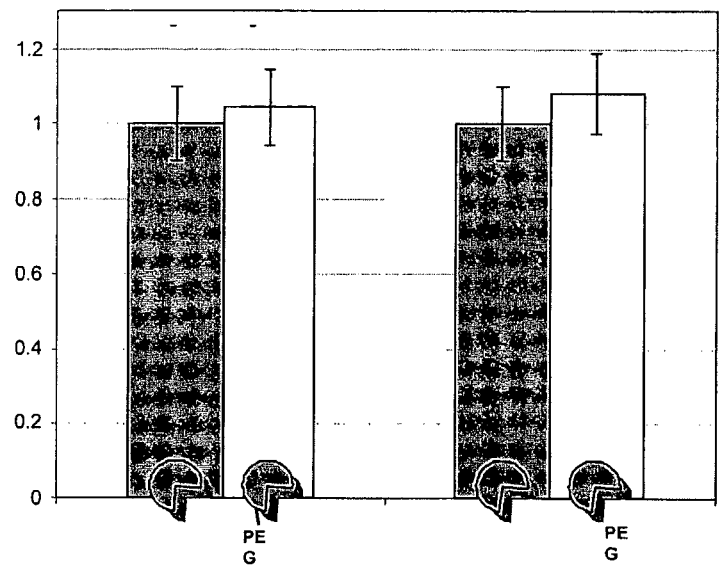
FIG. 10 shows that the attachment of a PEG linker to Exo-ATTTT or Exo-ATTTT-M184C does not affect enzyme activity. The Y-axis is relative activity. The left-hand pair of columns is Exo-ATTTT and the right-hand pair of columns is Exo-ATTTT-M184C. In each pair, the left-hand (darker) column is the enzyme with linker and the right-hand (lighter column) is enzyme without linker.

The construct examined was Exo-ATTTT-A83C. The linker used in these examples is a ssDNA linker with the 5' end free and the 3' end attached to the enzyme. The activity of Exo-ATTTT-A83C was measured with ssDNA linker attached and then the linker was removed by addition of DTT and activity remeasured. No change in activity was observed confirming the presence of the linker does not have a detrimental impact on activity (FIG. 8). In this examples activity of Exo-ATTTT-A83C was compared of free enzyme and PNA modified enzyme. No loss of activity was observed by addition of the PNA linker (FIG. 9). Exo ATTTT-M184C (with PEG). Controls were Exo ATTTT in the presence of PEG. No loss of activity was observed by addition of the PEG linker (FIG. 10).

2.3 Conclusion

We have created a range of mutants of EcoExo I where all the native cysteines have been removed. In addition, a single cysteine has been introduced to control the attachment chemistry of the ExoEco I. Somewhat surprisingly, the activity of some of the mutants is higher than the wild type.

The invention claimed is:

1. A method of covalently coupling two or more proteins, the method comprising:
   a) providing a first protein having covalently attached thereto (i) at least one first linker comprising a first hybridizable region and (ii) at least one first group capable of forming a covalent bond wherein the first group is covalently attached to the first protein via the first linker;
   b) providing a second protein having covalently attached thereto (i) at least one second linker comprising a second hybridizable region capable of hybridizing to the first hybridizable region and (ii) at least one second group capable of forming a covalent bond with the first group wherein the second group is covalently attached to the second protein via the second linker;
   c) contacting the first and second proteins under conditions that allow the first and second hybridizable regions to hybridize and link the proteins; and
   d) exposing the linked proteins to conditions that allow the formation of a covalent bond between the first and second groups.

2. A method according to claim 1, wherein the first protein has 2, 3 or 4 first linkers covalently attached thereto and the second protein has the corresponding number of second linkers attached thereto and wherein the linkers form one or more pairs of first and second linkers in which the hybridizable regions in each pair specifically hybridize to each other but do not hybridize to any of the hybridizable regions in the other pairs.

3. A method according to claim 2, wherein the method comprises:
   (a) providing a first protein having covalently attached thereto (i) a first linker comprising a first hybridizable region, (ii) a first group capable of forming a covalent bond, (iii) a third linker comprising a third hybridizable region and (iv) a third group capable of forming a covalent bond;
   (b) providing a second protein having covalently attached thereto (i) a second linker comprising a second hybridizable region capable of hybridizing to the first hybridizable region, (ii) a second group capable of forming a covalent bond with the first group, (iii) a fourth linker comprising a fourth hybridizable region capable of hybridizing to the third hybridizable region and (iv) a fourth group capable of forming a covalent bond with the third group;
   (c) contacting the first and second proteins under conditions that allow the first and second hybridizable regions to hybridize and allow the third and fourth hybridizable regions to hybridize and link the proteins; and
   (d) exposing the linked proteins to conditions that allow the formation of a covalent bond between the first and second groups and the third and fourth groups.

4. A method according to claim 1, wherein the first protein has covalently attached thereto (i) a first linker comprising a first hybridizable region, (ii) a first group capable of forming a covalent bond, (iii) a third linker comprising a third hybridizable region and (iv) a third group capable of forming a covalent bond and the second protein has covalently attached thereto (i) a second linker comprising a second hybridizable region capable of hybridizing to the first hybridizable region and a fourth hybridizable region capable of hybridizing to the third hybridizable region, (ii) a second group capable of forming a covalent bond with the first group and (iii) a fourth group capable of forming a covalent bond with the third group.

5. A method according to claim 1, wherein the method comprises coupling 3, 4 or 5 proteins and wherein each protein has covalently attached thereto (i) at least one linker which comprises a hybridizable region capable of hybridizing to the hybridizable region of a linker on a different protein and (ii) at least one group capable of forming a covalent bond with the group on a different protein.

6. A method according to claim 5, wherein the method comprises:
a) providing a first protein having covalently attached thereto (i) a first linker comprising a first hybridizable region and (ii) a first group capable of forming a covalent bond;
b) providing a second protein having covalently attached thereto (i) a second linker comprising a second hybridizable region capable of hybridizing to the first hybridizable region and (ii) a second group capable of forming a covalent bond with the first group, (ii) a third linker comprising a third hybridizable region and (iv) a third group capable of forming a covalent bond;
c) providing a third protein having covalently attached thereto (i) a fourth linker comprising a fourth hybridizable region capable of hybridizing to the third hybridizable region, (ii) a fourth group capable of forming a covalent bond with the third group;
d) contacting the first, second and third proteins under conditions that allow the hybridizable regions to hybridize and link the proteins; and
e) exposing the linked proteins to conditions that allow the formation of a covalent bond between the groups.

7. A method according to claim 1, wherein none of the groups react with themselves.

8. A method according to claim 1, wherein:
(a) the first protein is a nucleic acid binding protein and the second protein is a transmembrane protein pore;
(b) the first protein is a nucleic acid binding protein and the nucleic acid binding protein is derived from an exonuclease, a nuclease, a polymerase, a helicase or a topoisomerase;
(c) the first protein is a nucleic acid binding protein derived from an exonuclease and the exonuclease comprises the sequence shown in any one of SEQ ID NOs: 6 or a variant thereof;
(d) the first protein is a nucleic acid binding protein derived from an exonuclease and the exonuclease comprises the sequence shown in any one of SEQ ID NOs: 6, 52, 54 and 56 or a variant thereof;
(e) the first protein is a transmembrane protein pore and the transmembrane protein pore is α-hemolysin (α-HL);
(f) the first protein is a α-hemolysin and the pore comprises the sequence shown SEQ ID NO: 2 or 4 or a variant thereof;
(g) the first protein is a nucleic acid binding protein and the second protein is a transmembrane protein pore and the first and second groups is from 0.05 nm and 10 nm from their respective proteins; or
(h) the first protein is a nucleic acid binding protein and the second protein is a transmembrane protein pore and the distance between the coupled first and second proteins is from 0.1 nm and 500 nm.

9. A method according to claim 1, wherein the first and second hybridizable regions comprise a nucleic acid.

10. A method according to claim 9, wherein the nucleic acid is 6 to 15 nucleotides in length.

11. A method according to claim 1, wherein:
(a) the first and second hybridizable regions have an affinity of from 0.1 fM to 0.1 μM at a concentration from 1 pM to 1 mM;
(b) the first hybridizable region corresponds to the first 15, 25 or 35 nucleotides from the 5' end of SEQ ID NO: 57; or
(c) the first and second hybridizable regions comprise the following sequences respectively:
(i) the nucleotide sequences shown in SEQ ID NOs: 58 and 61;
(ii) the nucleotide sequences shown in SEQ ID NOs: 59 and 62;
(iii) the nucleotide sequences shown in SEQ ID NOs: 60 and 63;
(iv) the nucleotide sequences shown in SEQ ID NOs: 64 and 65;
(v) the nucleotide sequences shown in SEQ ID NOs: 66 and 68;
(vi) the nucleotide sequences shown in SEQ ID NOs: 67 and 69;
(vii) the nucleotide sequences shown in SEQ ID NOs: 70 and 73;
(viii) the nucleotide sequences shown in SEQ ID NOs: 71 and 74;
(ix) the nucleotide sequences shown in SEQ ID NOs: 72 and 75;
(x) the nucleotide sequences shown in SEQ ID NOs: 76 and 77; or
(xi) the nucleotide sequences shown in SEQ ID NOs: 78 and 67.

12. A method according to claim 1, wherein the first and second groups form a covalent bond by click chemistry.

13. A method according to claim 12, wherein the first group is an azide group and the second group is an alkyne group.

14. A method according to claim 1, wherein the first and second groups form a disulphide bond, an iodo acetamide bond or a bond via a metathesis reaction.

* * * * *